(12) United States Patent
Crowley et al.

(10) Patent No.: US 11,666,511 B2
(45) Date of Patent: *Jun. 6, 2023

(54) SYSTEMS AND METHODS FOR PORTABLE PILL DISPENSERS WITH VARIOUS DISPENSING MECHANISMS

(71) Applicant: INTENT SOLUTIONS, INC., Atlanta, GA (US)

(72) Inventors: Chris Crowley, Golden, CO (US); Tyler McCrary, Atlanta, GA (US); Ward Broom, Atlanta, GA (US); John Kidd, Atlanta, GA (US); Ashley B. Hancock, Atlanta, GA (US); Michael Ingoldby, Superior, CO (US); Roscoe Conkling Nelson, IV, Arvada, CO (US)

(73) Assignee: INTENT SOLUTIONS, INC., Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/646,888

(22) Filed: Jan. 4, 2022

(65) Prior Publication Data

US 2022/0125684 A1   Apr. 28, 2022

Related U.S. Application Data

(63) Continuation of application No. 16/958,404, filed as application No. PCT/US2018/066640 on Dec. 20, 2018, now Pat. No. 11,241,365.

(Continued)

(51) Int. Cl.
*A61J 7/00*    (2006.01)
*G16H 20/13*  (2018.01)

(Continued)

(52) U.S. Cl.
CPC .............. *A61J 7/0076* (2013.01); *A61J 1/03* (2013.01); *G06F 21/32* (2013.01); *G16H 20/13* (2018.01);

(Continued)

(58) Field of Classification Search
CPC .......... A61J 7/0076; A61J 1/03; G06F 21/32; G16H 20/13; G06K 9/00087; G06K 9/00617; G06V 40/197; G06V 40/1365
See application file for complete search history.

(56) References Cited

U.S. PATENT DOCUMENTS 3,833,147 A   9/1974  Borsum et al.
4,572,403 A   2/1986  Benaroya (Continued)

FOREIGN PATENT DOCUMENTS

CA   1258832 A    8/1989
CA   2152785 A1   7/1994

(Continued)

OTHER PUBLICATIONS

Communication from the European Patent Office dated Jul. 20, 2022.

(Continued)

*Primary Examiner* — Michael Collins
(74) *Attorney, Agent, or Firm* — Eversheds Sutherland (US) LLP

(57) ABSTRACT

Portable pill dispensers are disclosed herein. The portable pill dispenser may include a container configured to house at least one pill therein, a housing attachable to the container, and a dispensing mechanism disposed within the housing. In one configuration, the dispensing mechanism includes an oscillating member configured to dispense the at least one pill from the container.

16 Claims, 54 Drawing Sheets

Related U.S. Application Data

(60) Provisional application No. 62/610,634, filed on Dec. 27, 2017.

(51) Int. Cl.
  *A61J 1/03* (2023.01)
  *G06F 21/32* (2013.01)
  *G06V 40/18* (2022.01)
  *G06V 40/12* (2022.01)

(52) U.S. Cl.
  CPC ........ *G06V 40/1365* (2022.01); *G06V 40/197* (2022.01)

(56) References Cited

U.S. PATENT DOCUMENTS

| | | | |
|---|---|---|---|
| 4,653,668 A | 3/1987 | Gibilisco et al. | |
| 4,744,492 A * | 5/1988 | Hackmann | B65D 83/0409 221/204 |
| 4,785,969 A | 11/1988 | McLaughlin | |
| 4,834,263 A | 5/1989 | Becze | |
| 4,911,327 A | 3/1990 | Shepherd et al. | |
| 5,522,525 A | 6/1996 | McLaughlin et al. | |
| 5,657,901 A | 8/1997 | Farside | |
| 5,816,441 A | 10/1998 | Farside | |
| 6,216,910 B1 | 4/2001 | Numerick | |
| 6,237,804 B1 | 5/2001 | Peery et al. | |
| 6,324,123 B1 | 11/2001 | Durso | |
| 6,439,422 B1 | 8/2002 | Papp et al. | |
| 6,561,377 B1 | 5/2003 | Pearson et al. | |
| 6,601,729 B1 | 8/2003 | Papp | |
| 6,611,733 B1 | 8/2003 | De La Huerga | |
| 6,625,518 B2 | 9/2003 | Depeursinge | |
| 6,705,487 B2 | 3/2004 | Kim | |
| 6,732,884 B2 | 5/2004 | Toplife et al. | |
| 6,766,219 B1 | 7/2004 | Hasey | |
| 6,865,444 B2 | 3/2005 | Howard | |
| 7,073,685 B1 * | 7/2006 | Giraud | B65D 83/0409 221/64 |
| 7,108,153 B2 | 9/2006 | Wood | |
| 7,137,528 B1 | 11/2006 | Yates et al. | |
| 7,170,823 B2 | 1/2007 | Fabricius et al. | |
| 7,359,765 B2 | 4/2008 | Varvarelis et al. | |
| 7,440,817 B2 | 10/2008 | Fu | |
| 7,555,362 B2 * | 6/2009 | Broussard | A61J 7/02 221/12 |
| 7,715,277 B2 | 5/2010 | De La Huerga | |
| 7,747,347 B2 | 6/2010 | Park, IV | |
| 7,896,192 B2 | 3/2011 | Conley et al. | |
| 7,918,365 B2 * | 4/2011 | White | G07F 11/10 221/312 R |
| 7,944,342 B2 | 5/2011 | Sekura | |
| 7,963,201 B2 | 6/2011 | Willoughby et al. | |
| 7,978,564 B2 | 7/2011 | De La Huerga | |
| 7,988,016 B2 * | 8/2011 | Klein | B65D 50/062 221/160 |
| 8,027,748 B2 | 9/2011 | Handfield et al. | |
| 8,135,497 B2 | 3/2012 | Joslyn | |
| 8,335,697 B2 | 12/2012 | Siegel | |
| 8,362,914 B2 | 1/2013 | Hyde et al. | |
| 8,636,172 B2 | 1/2014 | Dunn | |
| 8,905,964 B2 | 12/2014 | Poutiatine et al. | |
| 9,492,357 B2 | 11/2016 | MacVittie et al. | |
| 9,501,626 B2 | 11/2016 | Zhang et al. | |
| 9,636,279 B2 | 5/2017 | Song et al. | |
| 9,730,860 B2 | 8/2017 | Hamilton | |
| 10,160,588 B2 * | 12/2018 | Akdogan | A61J 7/0076 |
| 10,792,224 B2 * | 10/2020 | Hancock | A61J 7/0076 |
| 10,940,092 B2 | 3/2021 | Song et al. | |
| 11,241,365 B2 * | 2/2022 | Crowley | G06F 21/32 |
| 2003/0183642 A1 | 10/2003 | Kempker | |
| 2004/0122554 A1 | 6/2004 | Howard | |
| 2004/0129716 A1 | 7/2004 | Naufel et al. | |
| 2005/0205598 A1 | 9/2005 | Gelardi | |
| 2006/0071011 A1 | 4/2006 | Varvarelis et al. | |
| 2006/0157491 A1 | 7/2006 | Whittle et al. | |
| 2008/0027579 A1 | 1/2008 | van der Hoop | |
| 2008/0251530 A1 | 10/2008 | Holloway et al. | |
| 2008/0300719 A1 | 12/2008 | Duke | |
| 2009/0105876 A1 | 4/2009 | Simpson et al. | |
| 2009/0218363 A1 | 9/2009 | Terzini | |
| 2009/0223994 A1 | 9/2009 | Getz | |
| 2009/0281657 A1 | 11/2009 | Gak et al. | |
| 2010/0318218 A1 | 12/2010 | Muncy, Jr. et al. | |
| 2011/0060457 A1 * | 3/2011 | De Vrught | A61J 7/0418 700/231 |
| 2011/0270442 A1 | 11/2011 | Conley et al. | |
| 2012/0003928 A1 | 1/2012 | Geboers et al. | |
| 2012/0316897 A1 | 12/2012 | Hanina et al. | |
| 2013/0187774 A1 | 7/2013 | Muecke et al. | |
| 2013/0200033 A1 * | 8/2013 | Zonana | A61J 7/0076 215/231 |
| 2014/0074283 A1 | 3/2014 | Blackbum | |
| 2014/0305963 A1 | 10/2014 | Zonana et al. | |
| 2015/0061867 A1 | 3/2015 | Engelhard et al. | |
| 2015/0379234 A1 | 12/2015 | Baig | |
| 2016/0022543 A1 | 1/2016 | Deeter | |
| 2016/0158107 A1 | 6/2016 | Dvorak et al. | |
| 2016/0287480 A1 * | 10/2016 | Hancock | A61J 7/02 |
| 2017/0079887 A1 | 3/2017 | Song et al. | |
| 2017/0231870 A1 | 8/2017 | Stachler et al. | |
| 2017/0296107 A1 | 10/2017 | Reid et al. | |
| 2017/0326033 A1 | 11/2017 | Kraft et al. | |
| 2017/0326034 A1 | 11/2017 | Lewis | |
| 2017/0333283 A1 | 11/2017 | Park | |

FOREIGN PATENT DOCUMENTS

| | | |
|---|---|---|
| CA | 2130252 A1 | 2/1996 |
| CA | 2217220 A1 | 6/1998 |
| CA | 2605237 A1 | 9/2006 |
| CN | 200998419 Y | 1/2008 |
| WO | 02/17850 A1 | 3/2002 |
| WO | 2012/148976 A1 | 11/2012 |
| WO | 2016/205609 A1 | 12/2016 |

OTHER PUBLICATIONS

"Facts on Nasper: National Drug Control Policy and Prevention of Prescription Drug Abuse Reauthorization Act of 2010", ASIPP, 2010 (3 pages).

International Search Report and Written Opinion for International Application No. PCT/US2014/030211, dated Jul. 15, 2014 (9 pages).

PCT International Search Report and Written Opinion dated Jun. 17, 2016 for International Application No. PCT/US2016/024435.

PCT International Search Report and Written Opinion dated May 23, 2019 for International Application No. PCT/US2018/066640.

* cited by examiner

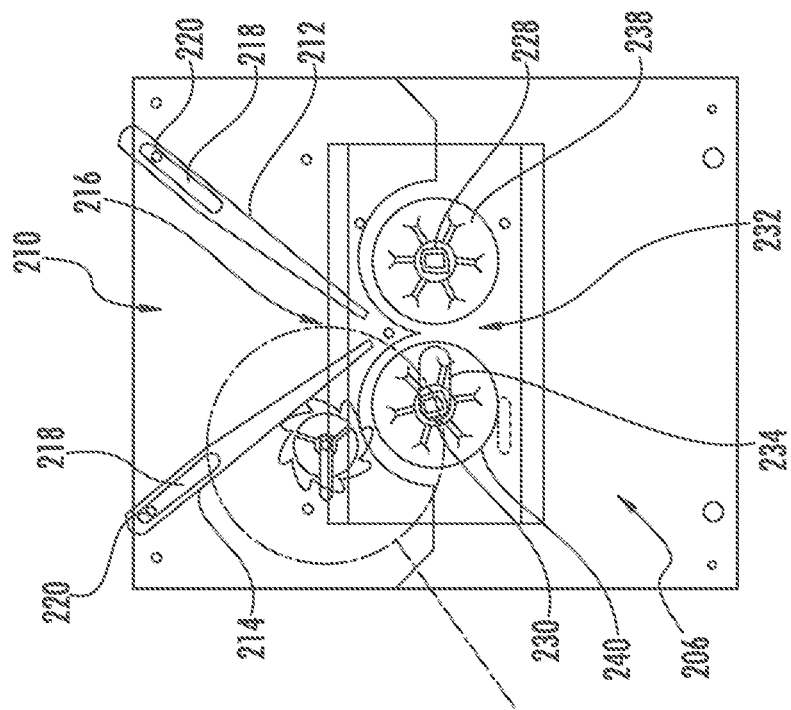
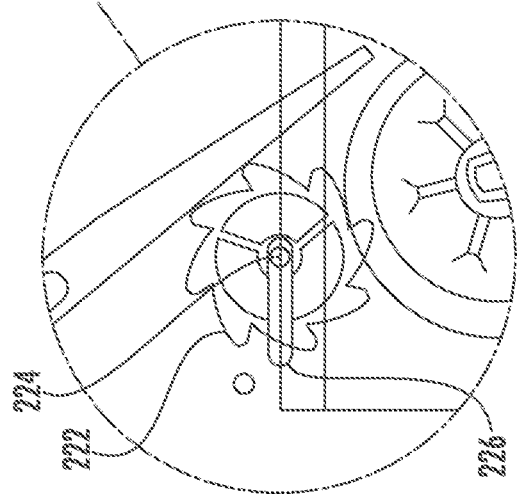
FIG. 18

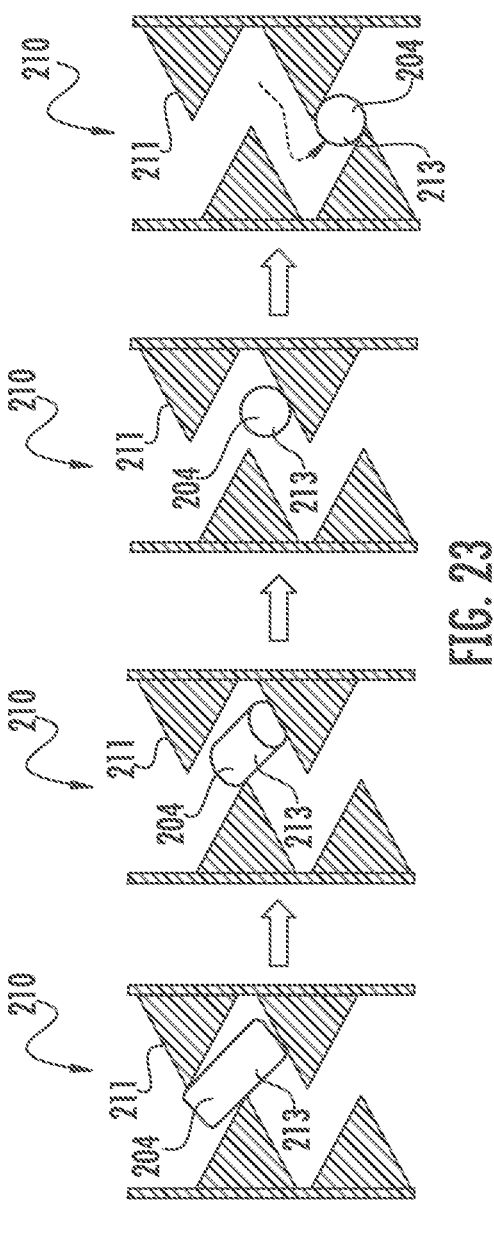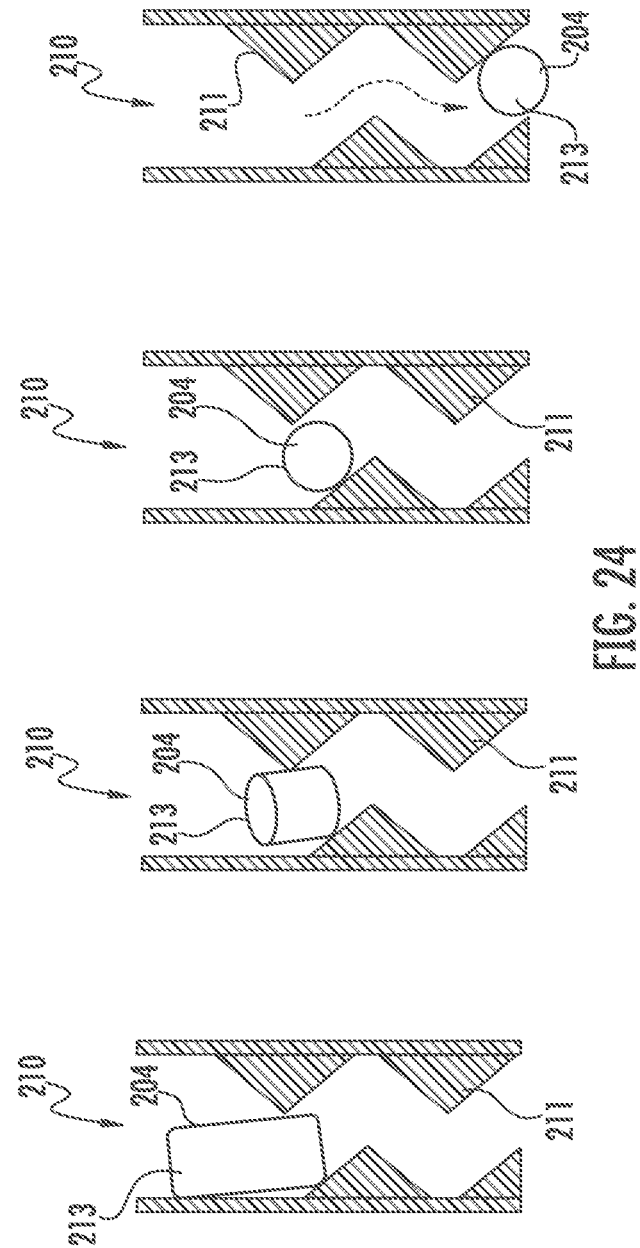

SYSTEMS AND METHODS FOR PORTABLE PILL DISPENSERS WITH VARIOUS DISPENSING MECHANISMS

CROSS-REFERENCE TO RELATED APPLICATIONS

This application claims priority to, the benefit of, and is a continuation of U.S. non-provisional application Ser. No. 16/958,404, filed Jun. 26, 2020, which claims priority to and the benefit of international application No. PCT/US2018/066640, filed Dec. 20, 2018, which claims priority to and the benefit of U.S. provisional patent application No. 62/610,634, filed Dec. 27, 2017, which are all hereby incorporated by reference herein in their entirety.

FIELD OF THE DISCLOSURE

The disclosure generally relates to pill dispensing and more particularly relates to systems and methods for dispensing pills by way of portable pill dispensers with various dispensing mechanisms.

BACKGROUND

It is desirable to prevent the misuse of medications by intended users and also to ensure correct dispensing of prescription medications. It is also desirable to monitor and record the dispensing of prescription medications to intended users. In this manner, it would be useful to provide a portable pill dispenser and monitoring system to verify that medications stored therein are not taken in excess (i.e., abused) and are only taken at the prescribed interval and dose. It also would be useful to provide a portable pill dispenser and monitoring system to verify that medications stored therein are removed only by the patient or another authorized person in order to prevent drug abuse, diversion, and/or mistake. In addition, it would be useful to provide a portable pill dispenser that is capable of dispensing one pill at a time.

BRIEF DESCRIPTION

A portable pill dispenser is disclosed herein. The portable pill dispenser includes a container configured to house at least one pill therein, a housing attachable to the container, and a dispensing mechanism disposed within the housing. In one embodiment, the dispensing mechanism comprises an oscillating member configured to dispense the at least one pill from the container. Other new dispensing mechanisms are also disclosed.

BRIEF DESCRIPTION OF THE DRAWINGS

The detailed description is set forth with reference to the accompanying drawings. The use of the same reference numerals may indicate similar or identical items. Various embodiments may utilize elements and/or components other than those illustrated in the drawings, and some elements and/or components may not be present in various embodiments. Elements and/or components in the figures are not necessarily drawn to scale. Throughout this disclosure, depending on the context, singular and plural terminology may be used interchangeably.

FIG. 18 depicts a dispensing mechanism of a portable pill dispenser in accordance with one or more embodiments of the disclosure.

FIG. 23 depicts a dispensing sequence in accordance with one or more embodiments of the disclosure.

FIG. 24 depicts a dispensing sequence in accordance with one or more embodiments of the disclosure.

DETAILED DESCRIPTION

Figure 1:
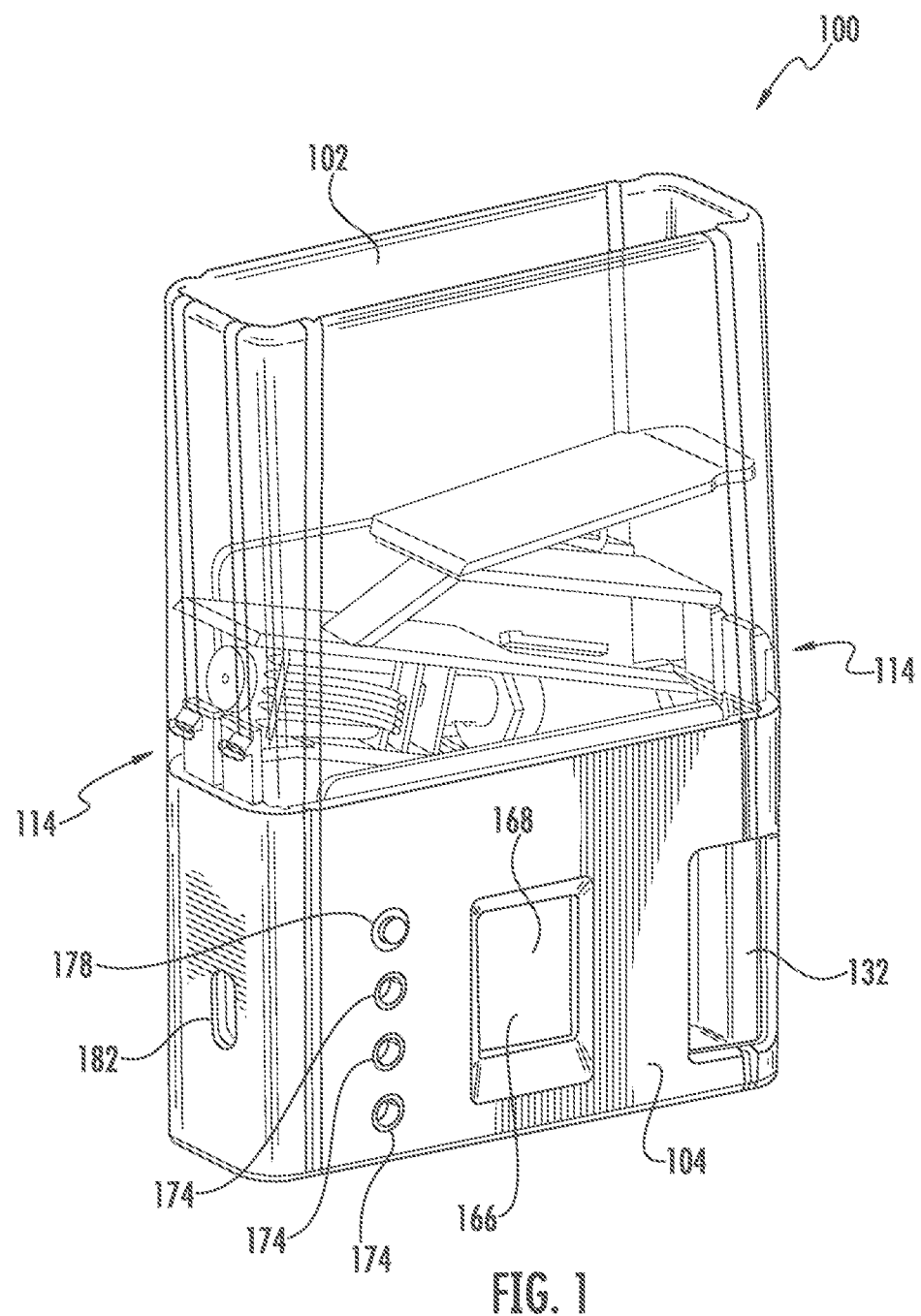
FIG. 1 depicts a portable pill dispenser in accordance with one or more embodiments of the disclosure.

Described below are embodiments of portable pill dispensers (as well as individual components of the portable pill dispensers). As used herein, the term "pills" refers to tablets, capsules, gel caps, and other dosage units known in the art for administering pharmaceutical agents (or placebos of the same). Typically, the pill is a solid oral dosage form known in the art. Methods of manufacturing and using the portable pill dispensers are also disclosed. In some instances, the portable pill dispensers may be used in clinical trials. For example, one or more of the participants (patients) in the client trial each may be provided with a portable pill dispenser. Information from the portable pill dispenser may be monitored, recorded, and provided to the operator of the clinical trial. The information provided by the portable pill dispensers may help ensure the integrity of the clinical trial. The information provided by the portable pill dispensers may be highly useful information, such as when the patient takes the pills, information which may be far more accurate than relying of the patient's own recollection and independent recordkeeping. Moreover, the operator of the clinical trial may remotely monitor, record, control, modify, and/or adjust the dispensing capabilities of the portable pill dispensers as necessary in order to carry out the clinical trial as efficiently and cost-effectively as possible. In other embodiments, the portable pill dispensers are used by patients not in a clinical trial, such as in dispensing any approved drug to a patient as prescribed by his or her physician. The portable pill dispenser may be used in any setting to monitor, record, and/or adjust the dispensing of a drug.

The portable pill dispensers may prevent the misuse of medications by intended users and also ensure correct dispensing of prescription medications. For example, the portable pill dispensers may monitor and record the dispensing of prescription medications to intended users and verify that medications stored therein are not taken in excess (e.g., abused) and are taken only at the prescribed intervals and doses. In addition, the portable pill dispensers may verify that medications stored therein are removed only by the patient or another authorized person in order to deter drug abuse, diversion, and/or mistake. The portable pill dispensers can aid the patient to take (e.g., ingest) his or her medication as directed (as prescribed) by his or her physician. The portable pill dispensers also may determine if a dose was missed.

The term "portable" refers to a pill dispenser that may be easily carried by a user, such as in one of his or her hands, or within a pocket of his or her clothing. In this manner, the size and shape of the portable pill dispenser may enable a user to carry the portable pill dispenser on his or her person in essentially the same way that a current model mobile phone or smart phone is typically carried by a person. That is, the overall dimensions of the portable pill dispenser are such that a user can easily hold it in one hand, or can readily carry it, for example, in a pocket of his or her jacket, pants, shirt, shorts, or overcoat, or in a handbag or backpack. In this manner, a user may keep the portable pill dispenser on their person, e.g., in a concealed manner, throughout the day. In some instances, the user may operate the portable pill dispenser with one hand. In other instances, the user may hold the portable pill dispenser in one hand and operate it with the other hand. In other instances, all of the dispensing mechanism described herein may be used in association with a stationary, non-portable pill dispensing device, such as in a pharmacy or high volume pill manufacturing facility.

FIG. 1 schematically depicts a portable pill dispenser 100. The portable pill dispenser 100 includes a container 102. The container 102 is configured to house at least one pill therein. In some instances, a number of pills (e.g., 2 to 100 or more pills) are stored within the container 102. The container 102 may be transparent or opaque. The container 102 may be disposable or reusable. The container 102 may be any suitable size, shape, or configuration. The container 102 may include a container label on an exterior surface thereof. For example, the container 102 may include a prescription label thereon. The prescription label may identify the pills therein, provide instructions to the patient, provide a medication dosage regimen, provide patient information, provide doctor information, provide warnings, and/or provide emergency instructions, or the like. The information may be in the form of text, a barcode, and/or a data chip. Any information may be included on the container label and/or on the container 102 itself.

Figure 2:
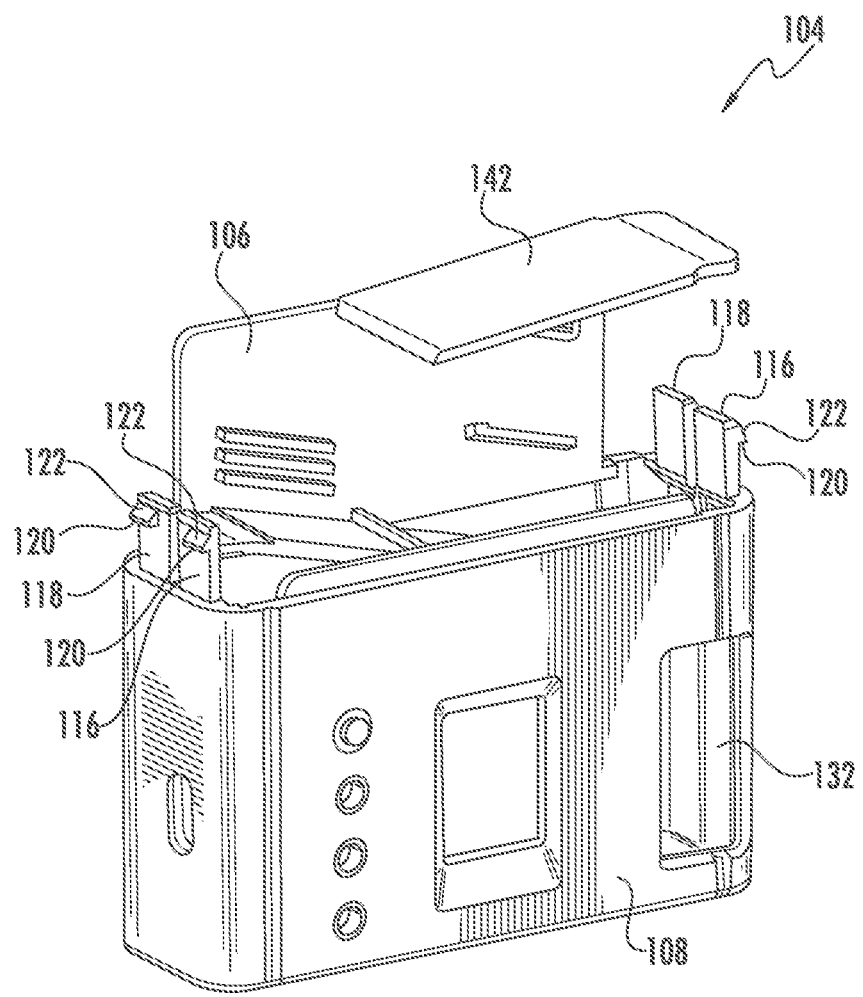
FIG. 2 depicts a housing of a portable pill dispenser in accordance with one or more embodiments of the disclosure.
Figure 3:
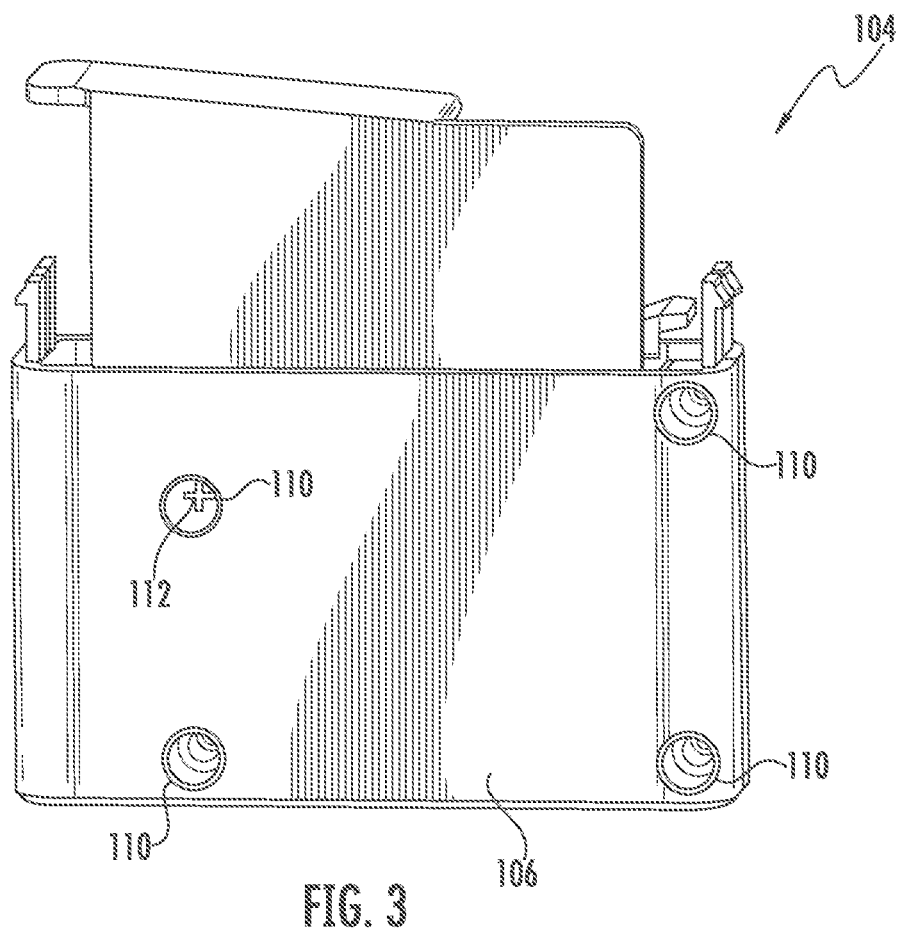
FIG. 3 depicts a housing of a portable pill dispenser in accordance with one or more embodiments of the disclosure.

The container 102 is attachable to a housing 104. As depicted in FIGS. 1-3, the housing 104 may include a rear portion 106 that is attached to a front portion 108. The front portion 108 and the rear portion 106 may be screwed, welded, or the like. In certain embodiments, the front portion 108 and the rear portion 106 may be a single unitary body. In some instances, the rear portion 106 and the front portion 108 are screwed together. For example, the front portion 108 and the rear portion 106 may include one or more bores 110 and corresponding screws 112. The rear portion 106 and the front portion 108 may include one or more internal platforms, frames, lips, walls, attachment points or the like for attaching, aligning, securing, and/or positioning the various components disposed within the housing 104. The housing 104 may be any suitable size, shape, or configuration.

Figure 4:
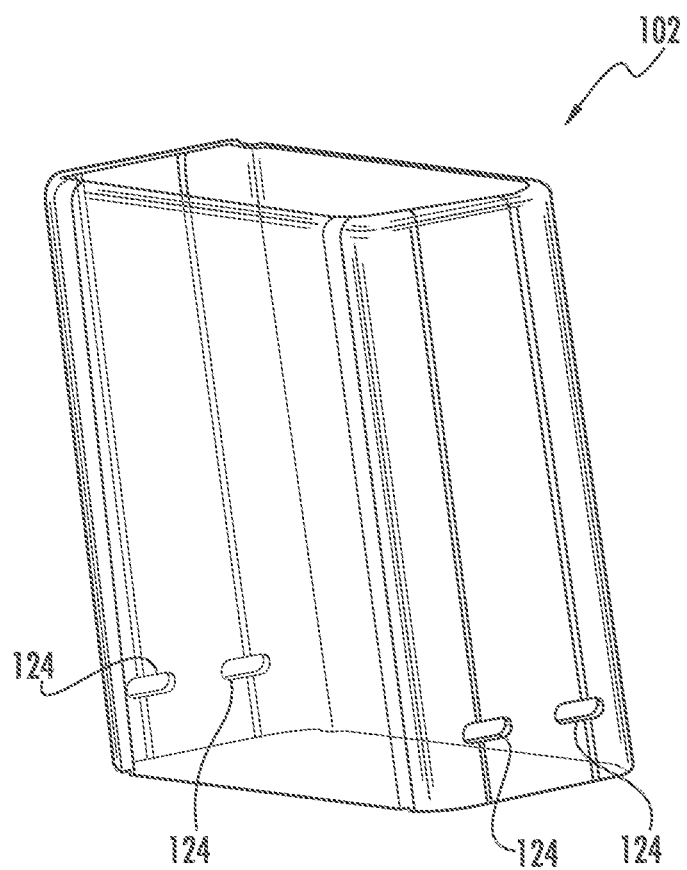
FIG. 4 depicts a container of a portable pill dispenser in accordance with one or more embodiments of the disclosure.

In certain embodiments, the portable pill dispenser 100 includes an attachment mechanism 114 configured to releasably or reversibly secure the container 102 to the housing 104. As depicted in FIG. 2, the attachment mechanism 114 comprises a pair of first resilient tabs 116 extending from the front portion 108 on each side thereof. The attachment mechanism 114 also comprises a pair of second resilient tabs 118 extending from the rear portion 106 on each side thereof. In some instances, the first and second resilient tabs include lips 120. The lips 120 are formed by a triangular protrusion 122 projecting outward from a distal tip of the first and second resilient tabs 116, 118. The lips 120 are configured to mate with apertures 124, as depicted in FIG. 4, in the side of the container 102 to secure the container 102 to the housing 104. The shape of the triangular protrusions 122 causes the first and second tabs 116, 118 to flex inward as the container 102 is pressed together with the housing 104. Once the triangular protrusions 122 are aligned with the apertures 124, the first and second resilient tabs 116, 118 snap back into their repose position, which causes the lips 120 to engage an edge of the apertures 124 to secure the container 102 to the housing 104. In some instances, tamper stickers may be placed over the apertures 124 to prevent the container 102 from being removed from the housing 104 without breaking the stickers, evidencing that unauthorized access to the container contents has occurred. In some instances, a tamper sensor may be disposed about the container and the housing to detect when the container is separated from the housing.

Figure 5:
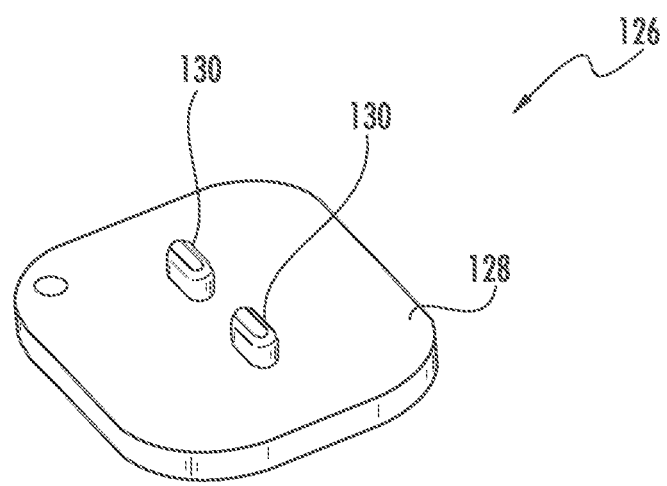
FIG. 5 depicts a tool in accordance with one or more embodiments of the disclosure.

FIG. 5 depicts a tool 126 for removing the container 102 from the housing 104. The tool 126 includes a main body 128 with a pair of protrusions 130 extending therefrom. The protrusions 130 are sized and shaped to correspond to the apertures 124 so as to press against the triangular protrusions 122 to bend the first and second resilient tabs inward 116, 118, thereby disengaging the lips 120 from the apertures 124, which enables the container 102 to be removed from the housing 104. In some instances, only an authorized person (such as a pharmacist, physician, or clinical trial operator) may have access to the tool 126. Any type of tamper resistance attachment mechanism may be used herein. In some instances, for additional security, a removable tamper resistant housing may encase the portable pill dispenser 100. The tamper resistant housing may be smash proof. For example, the tamper resistant housing may form a metal jacket about the portable pill dispenser. The tamper resistant housing may be used when transporting certain narcotics or the like, e.g., Schedule II or III drugs.

Figure 6:
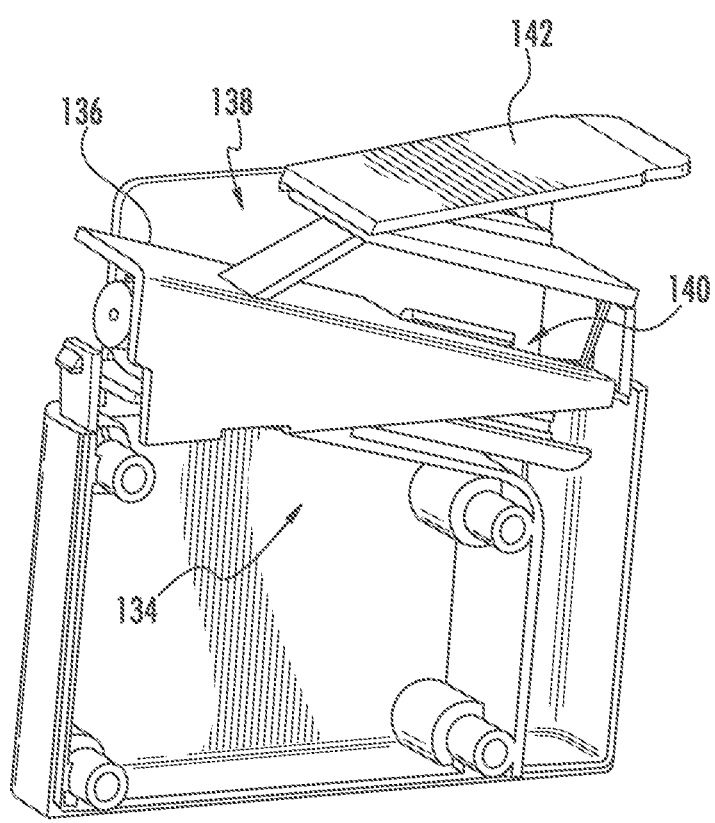
FIG. 6 depicts a housing of a portable pill dispenser with a ramp in accordance with one or more embodiments of the disclosure.
Figure 7:
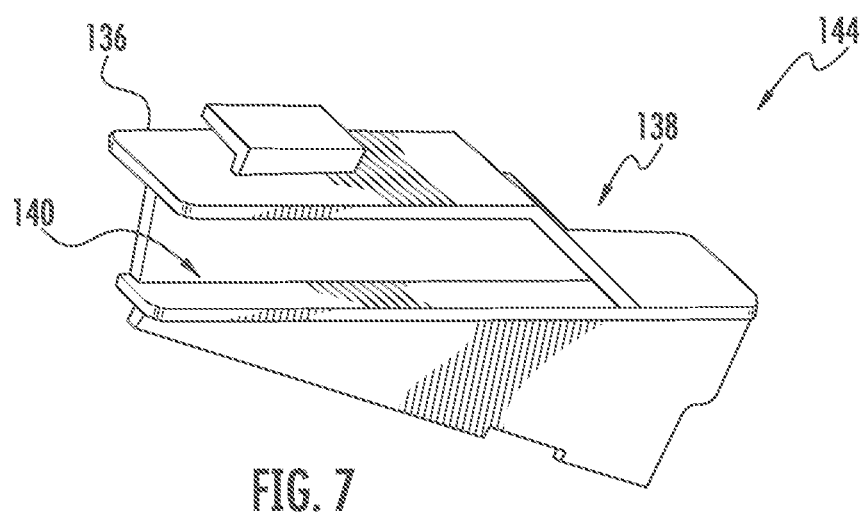
FIG. 7 depicts a ramp in accordance with one or more embodiments of the disclosure.
Figure 8:
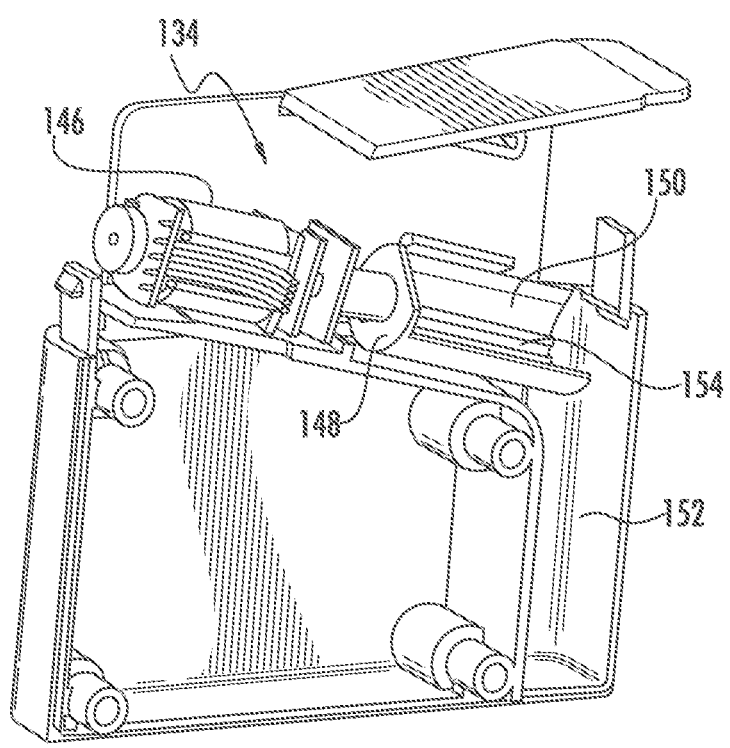
FIG. 8 depicts a dispensing mechanism of a portable pill dispenser in accordance with one or more embodiments of the disclosure.

The portable pill dispenser 100 is configured to dispense pills. For example, as depicted in FIG. 1, the front portion 108 includes a dispensing opening 132. In addition, as depicted in FIGS. 6-8, a dispensing mechanism 134 and a ramp 136 are disposed within the housing 104 and may extend into the container 102. The ramp 136 is configured to guide the pills from the container 102 to the dispensing mechanism 134. In some instances, the ramp 136 guides one pill at a time to the dispensing mechanism 134. That is, the ramp 136 is sized and shaped to align one pill into the dispensing mechanism 134 at a time. In this manner, the ramp 136 includes an inlet 138 facing the container 102 and an outlet 140 facing the dispensing mechanism 134. The size and shape of the inlet 138 and the outlet 140 may vary depending on the pills being dispensed. The ramp 136 may include one or more angled portions so as to use gravity to cause the pills to slide into the dispensing mechanism 134. For example, the ramp 136 functions as a funnel directing one pill at a time to the dispensing mechanism 134. In some instances, the ramp 136 is at least partially formed by a ledge 142 extending from the rear portion 106. The ledge 142 may direct pills to the inlet 138 of the ramp 136. In other instances, the ledge 142 may be omitted. The ramp 136 may be any size, shape, or configuration.

Figure 35:
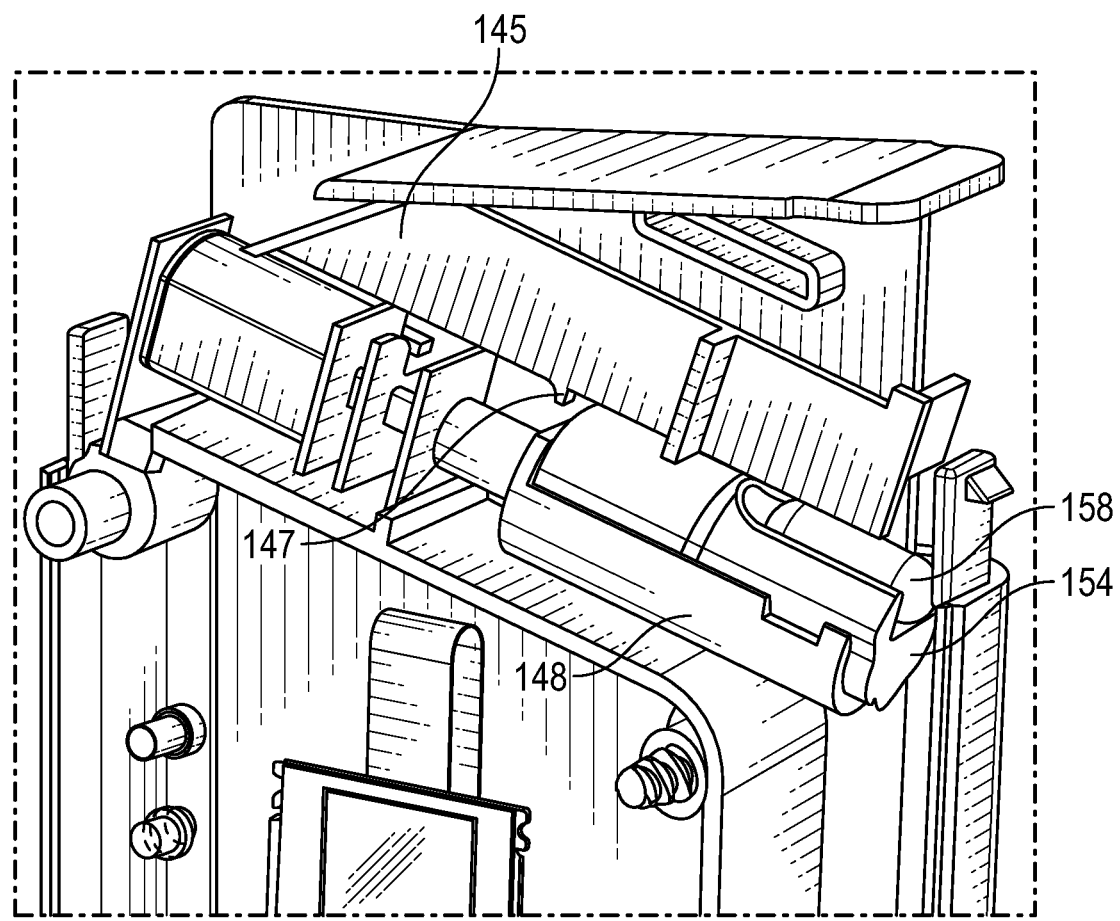
FIG. 35 depicts a removable insert of a portable pill dispenser in accordance with one or more embodiments of the disclosure.
Figure 36:
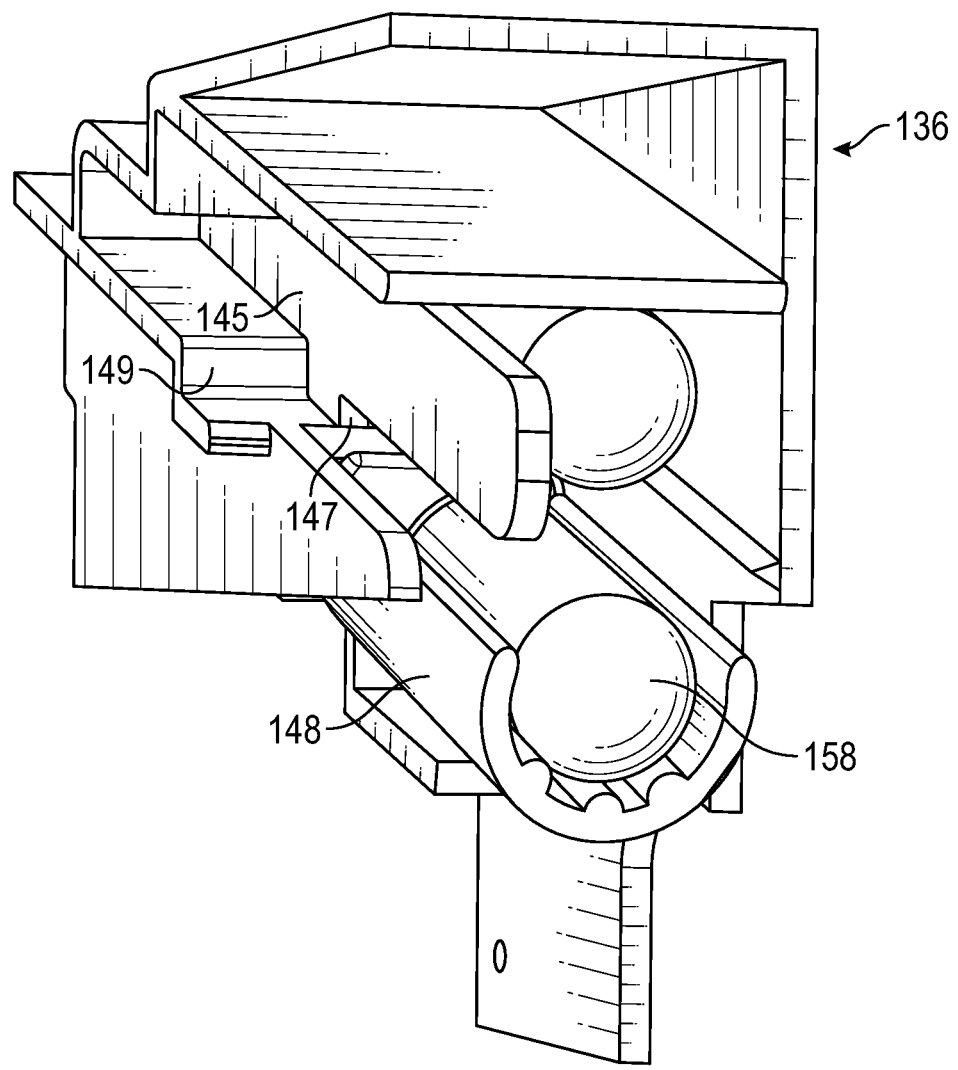
FIG. 36 depicts a movable wall of a portable pill dispenser in accordance with one or more embodiments of the disclosure.
Figure 37:
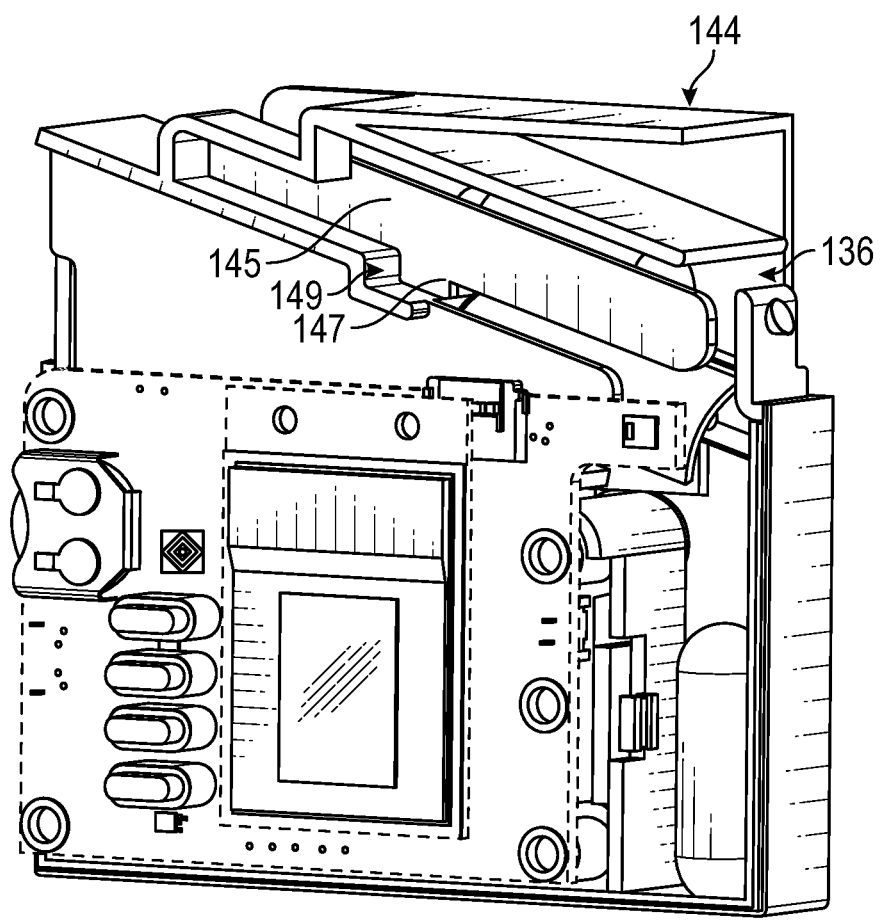
FIG. 37 depicts a movable wall of a portable pill dispenser in accordance with one or more embodiments of the disclosure.

In some instances, as depicted in FIGS. 35-37, the ramp 136 includes a movable wall 145 configured to adjust the size of the ramp 136. For example, the movable wall 145 includes a notch 147 configured to slide along channel 149 formed in the ramp 136. In this manner, the movable wall 145 may slide laterally from side-to-side in order to adjust the size (width) of the ramp 136 to accommodate different sized and shaped pills.

In some instances, the ramp 136 comprises a removable ramp insert 144. The removable ramp insert 144 may be removed and replaced with a ramp having a different size, shape, or configuration to accommodate pills of varying sizes and/or shapes. For example, the removable ramp insert 144 is removably attached to the rear portion 106. In this manner, the portable pill dispenser 100 may be customized for pills of different shapes and sizes. The movable wall 145 may be incorporated into the removable ramp insert 144.

The dispensing mechanism 134 is configured to dispense the pills from the container to the dispensing opening 132. In some instance, the dispensing mechanism 134 comprises a motor 146 (e.g., an electric motor) in mechanical communication with a rotating barrel 148. The motor 146 may be in direct or indirect (e.g., via one or more gears) mechanical communication with the rotating barrel 148. The motor 146 and the rotating barrel 148 may be positioned beneath the ramp 136. In this manner, the rotating barrel 148 is positioned about the outlet 140 of the ramp 136. The rotating barrel 148 may be angled downward to facilitate dispensing of the pills. The rotating barrel 148 comprises a cavity 150 configured to receive the pill therein. The cavity 150 may be sized and shaped to accommodate one pill at a time. In some instances, the rotating barrel 148 includes a number of cavities. In this manner, rotation of the rotating barrel 148 dispenses the pill within the cavity 150 to a passageway 152, which leads to the dispensing opening 132. In certain embodiments, once all of the pills have been dispensed, the container 102 may be removed from the housing 102 and a new container 102 may be attached thereto. In other instances, the container 102 may be refilled.

Figure 33:
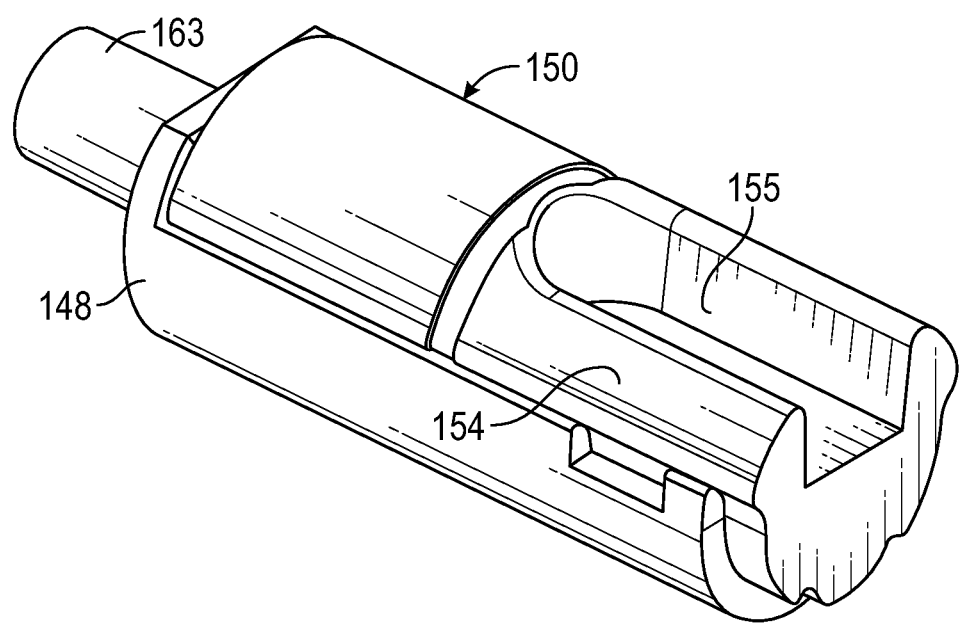
FIG. 33 depicts a removable insert of a portable pill dispenser in accordance with one or more embodiments of the disclosure.
Figure 34:
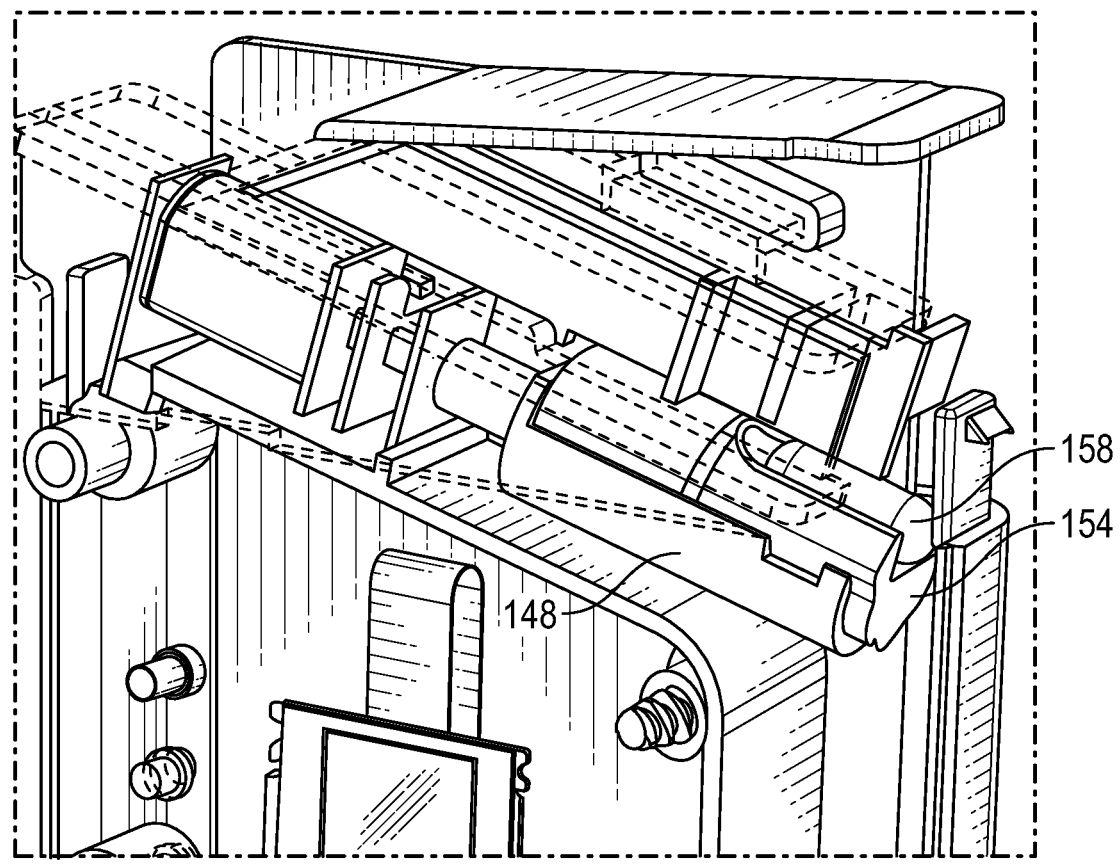
FIG. 34 depicts a removable insert of a portable pill dispenser in accordance with one or more embodiments of the disclosure.

In order to accommodate pills of varying sizes and/or shapes, a removable insert 154 may be disposed within the cavity 150. The removable insert 154 may adjust the size and/or shape of the cavity 150. In this manner, depending of the pills being dispensed, different sized and/or shaped removable inserts 154 may be disposed within the cavity 150 to adjust the portable pill dispenser 100 to accommodate a variety of pills. The removable insert 154 may be any size, shape, or configuration. In this manner, the portable pill dispenser 100 may be customized for different pills. For example, as depicted in FIGS. 32-35, the removable insert 154 is disposed within the cavity of the rotating barrel 148. In some instances, removable insert 154 includes a smaller cavity 155 for accommodating smaller pills than the cavity 150. The smaller cavity 155 may be any suitable size, shape, or configuration. In some instances, the smaller cavity 155 is open ended, as depicted in FIG. 33.

Figure 9:
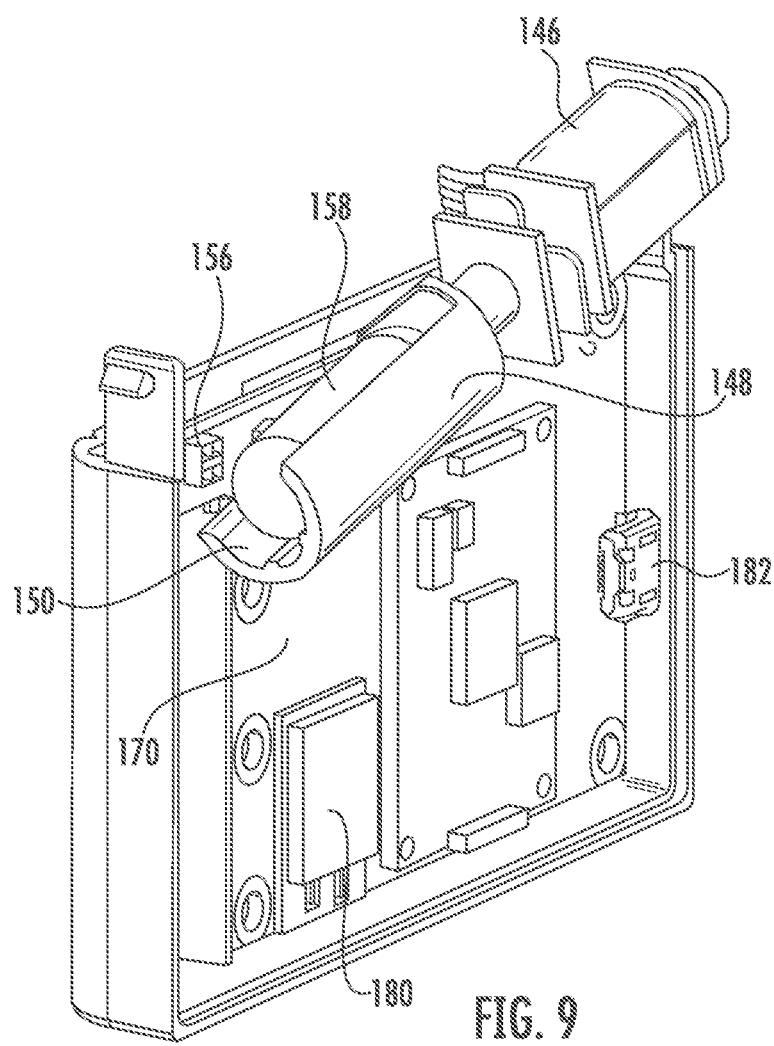
FIG. 9 depicts a dispensing mechanism and a control panel of a portable pill dispenser in accordance with one or more embodiments of the disclosure.

As depicted in FIG. 9, the portable pill dispenser 100 also may include a pill sensor 156 disposed within the housing 104. The pill sensor 156 may be located anywhere within the housing 104. For example, the pill sensor 156 is disposed within or adjacent to the cavity 150, within or adjacent to the passageway 152, and/or within or adjacent to the dispensing opening 132. The pill sensor 156 is configured to detect the pill 158 being dispensed to the dispensing opening 132. In some instances, the pill sensor 156 detects the pill 158 within the cavity 150, passing from the cavity 150 to the passageway 152, and/or from the passageway 152 to the dispensing opening 132. Any type of pill sensor 156 may be used. In one embodiment, the pill sensor 156 is a photo reflective sensor, which may detect the pill 158 based on light reflection from the pill 158 compared to light reflection from the rotating barrel 148. The wavelength of light is chosen to maximize the signal difference between the pill 158 and the rotating barrel 148. By way of example, the dispensing mechanism 134 can be optimized to maximally reflect the chosen wavelengths of light while the pill 158 maximally absorbs the chosen wavelengths of light. Various mechanisms that can be used to maximize the differences in absorption or reflection of light can include reflection, refraction, light scatter, light diffusion, surface textures, dispenser color, dispenser material choice, dispenser coatings, material fluorescence, or the like. In other instances, the pill sensor 156 is a limit switch or the like. Moreover, any number of pill sensors 156 may be used. For example, multiple pill sensors 156 can detect the movement of the pill 158 at each stage from the container 102 to the dispensing opening 132.

Figure 10:
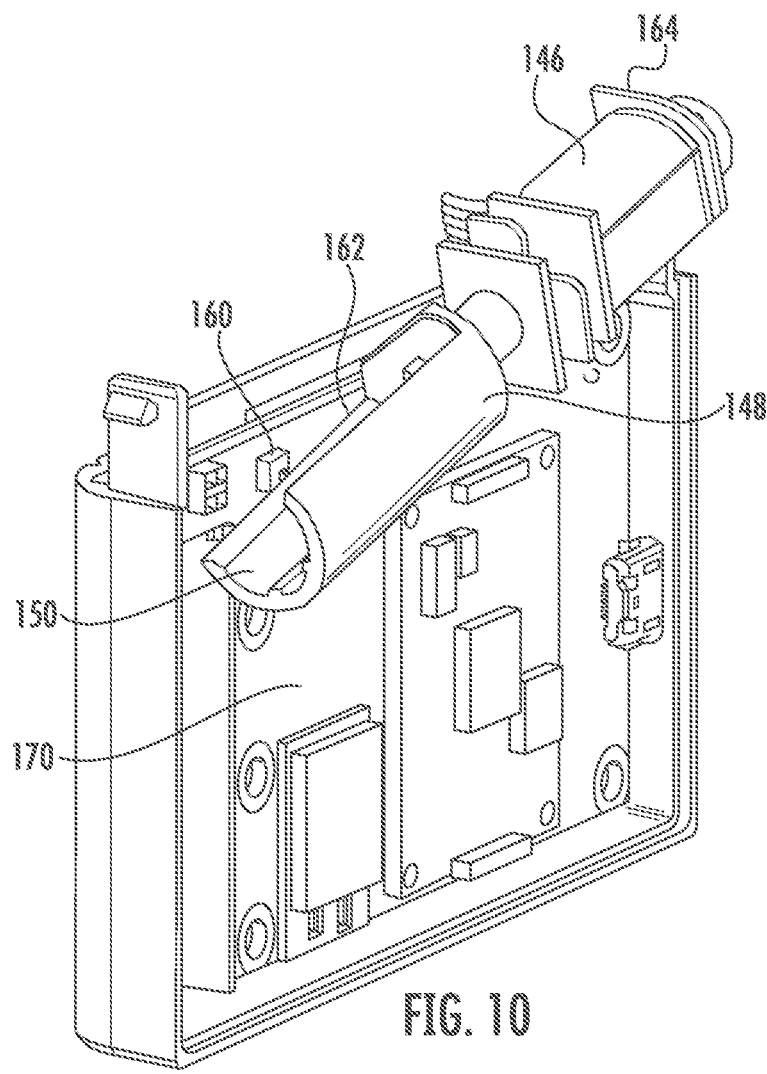
FIG. 10 depicts a dispensing mechanism and a control panel of a portable pill dispenser in accordance with one or more embodiments of the disclosure.
Figure 11:
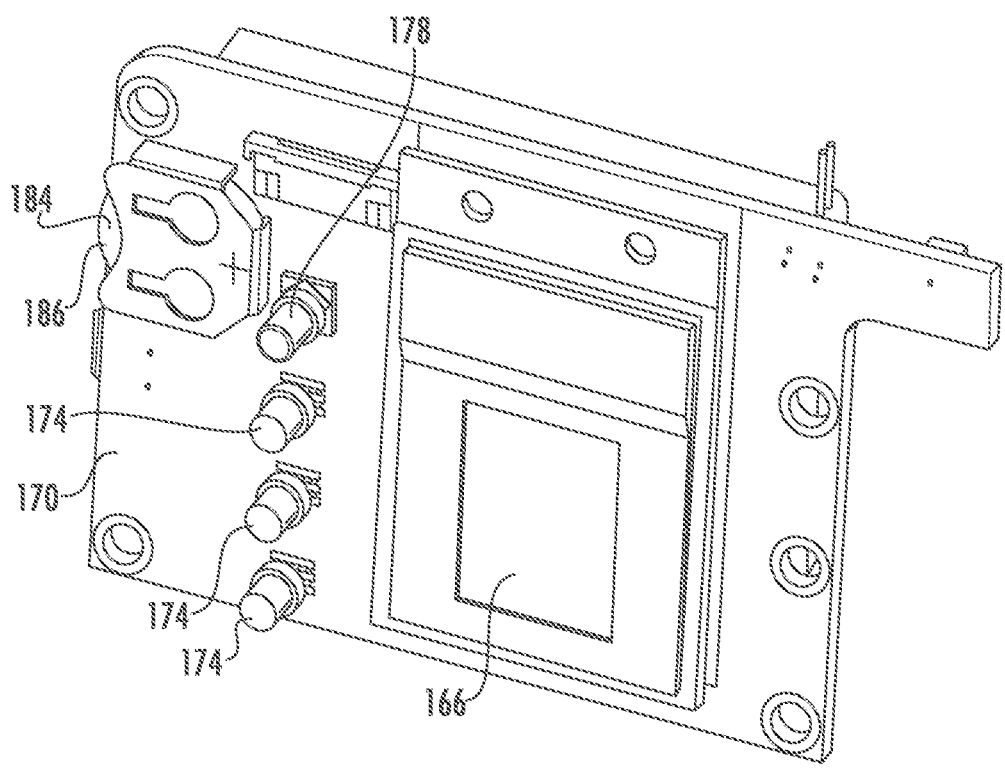
FIG. 11 depicts a control panel of a portable pill dispenser in accordance with one or more embodiments of the disclosure.
Figure 12:
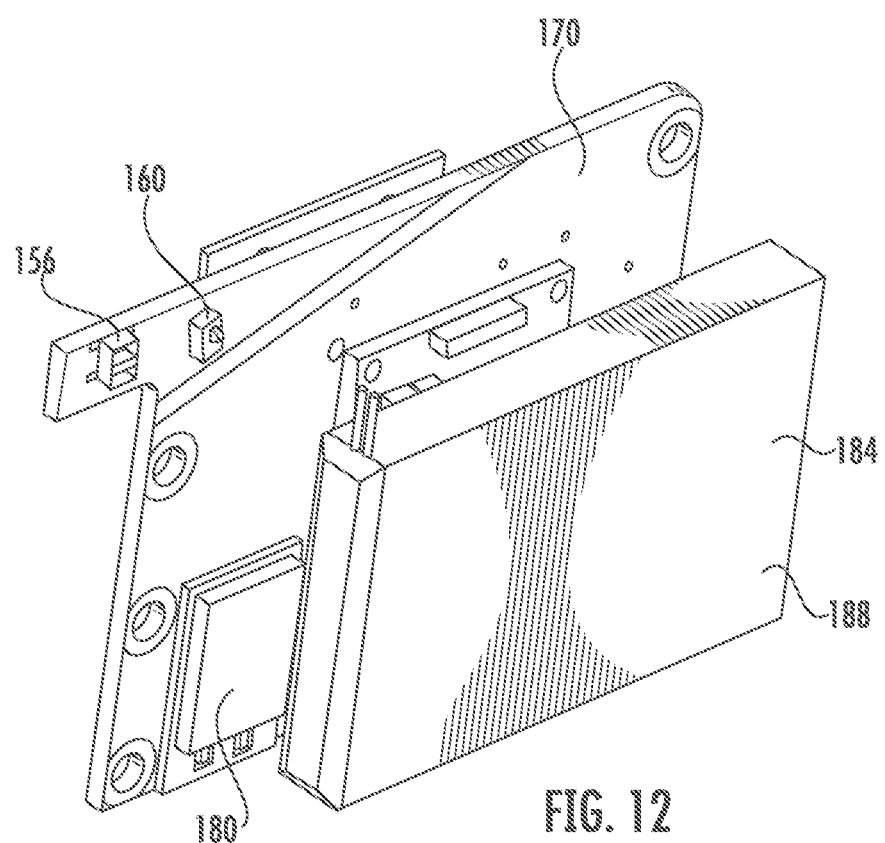
FIG. 12 depicts a control panel and battery of a portable pill dispenser in accordance with one or more embodiments of the disclosure.

In some instances, as depicted in FIG. 10, a rotation sensor 160 is disposed within the housing 104 about the rotating barrel 148. The rotation sensor 160 is configured to detect the annular position of the rotating barrel 148. The rotation sensor 160 may be particularly useful in determining the location of the cavity 150. In some instances, the rotation sensor 160 is a trigger sensor (e.g., limit switch) that engages an edge 162 of the rotating barrel 148 as it rotates. Other types of rotation sensors 160 may be used, including, but not limited to, a magnetic sensor or a photo reflector sensor configured to detect a sticker or other indicia on the rotating barrel 148. Moreover, a tachometer 164 may be disposed about the motor 146. The rotation sensor 160 and the tachometer 164 may collectively determine the annular position of the rotating barrel 148. In some instances, a tachometer, a limit switch, a photo reflective sensor, and/or a motor current sensor may be used to detect a "jam" and take appropriate action. For instance, if the motor current is high such that the rotating barrel should be spinning, and the photo reflective sensor and/or limit switch do not sense the barrel rotating, the motor may be instructed to run in reverse or to run back-and-forth several times. In addition, an error message may be displayed or a wireless signal may be sent to a smartphone or other companion electronic device.

Figure 29:
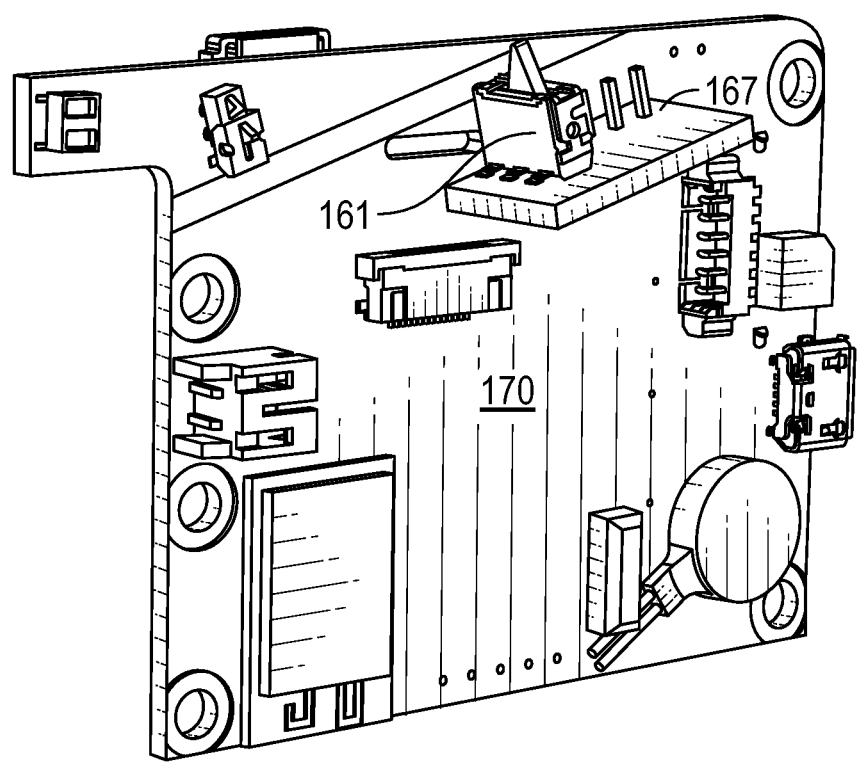
FIG. 29 depicts a control panel of a portable pill dispenser in accordance with one or more embodiments of the disclosure.
Figure 30:
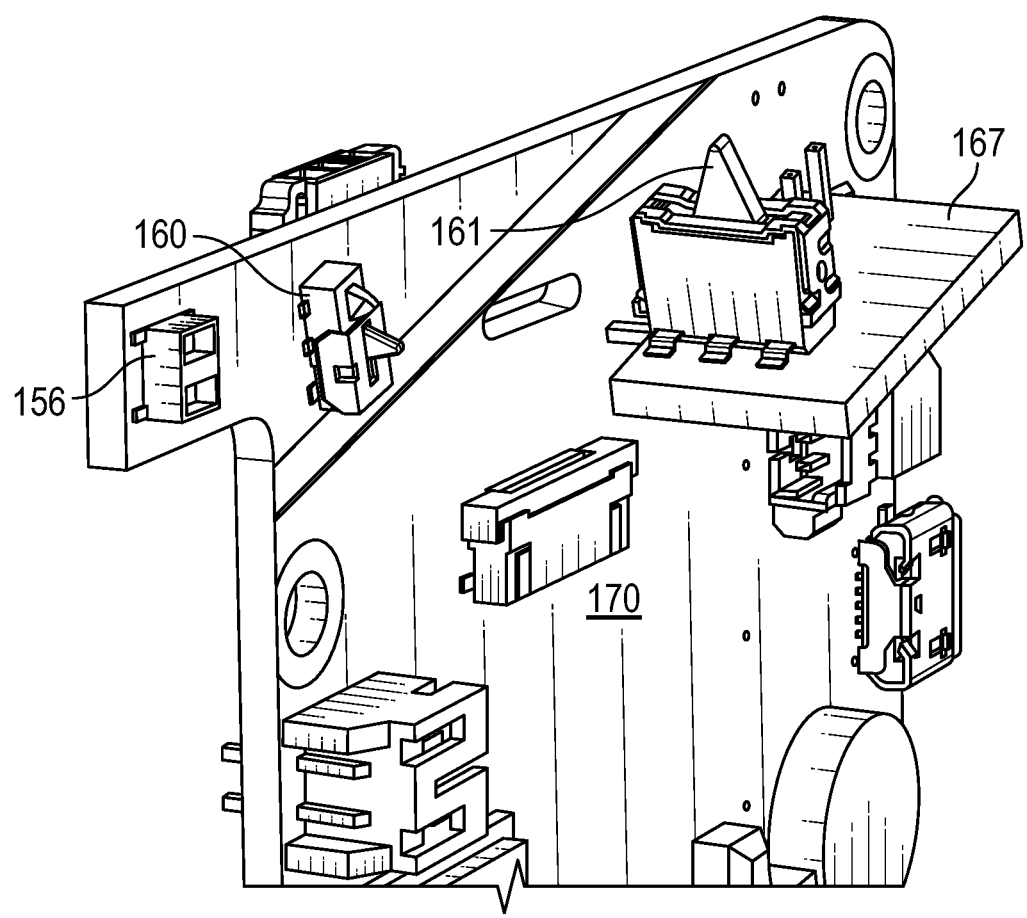
FIG. 30 depicts a control panel of a portable pill dispenser in accordance with one or more embodiments of the disclosure.
Figure 31:
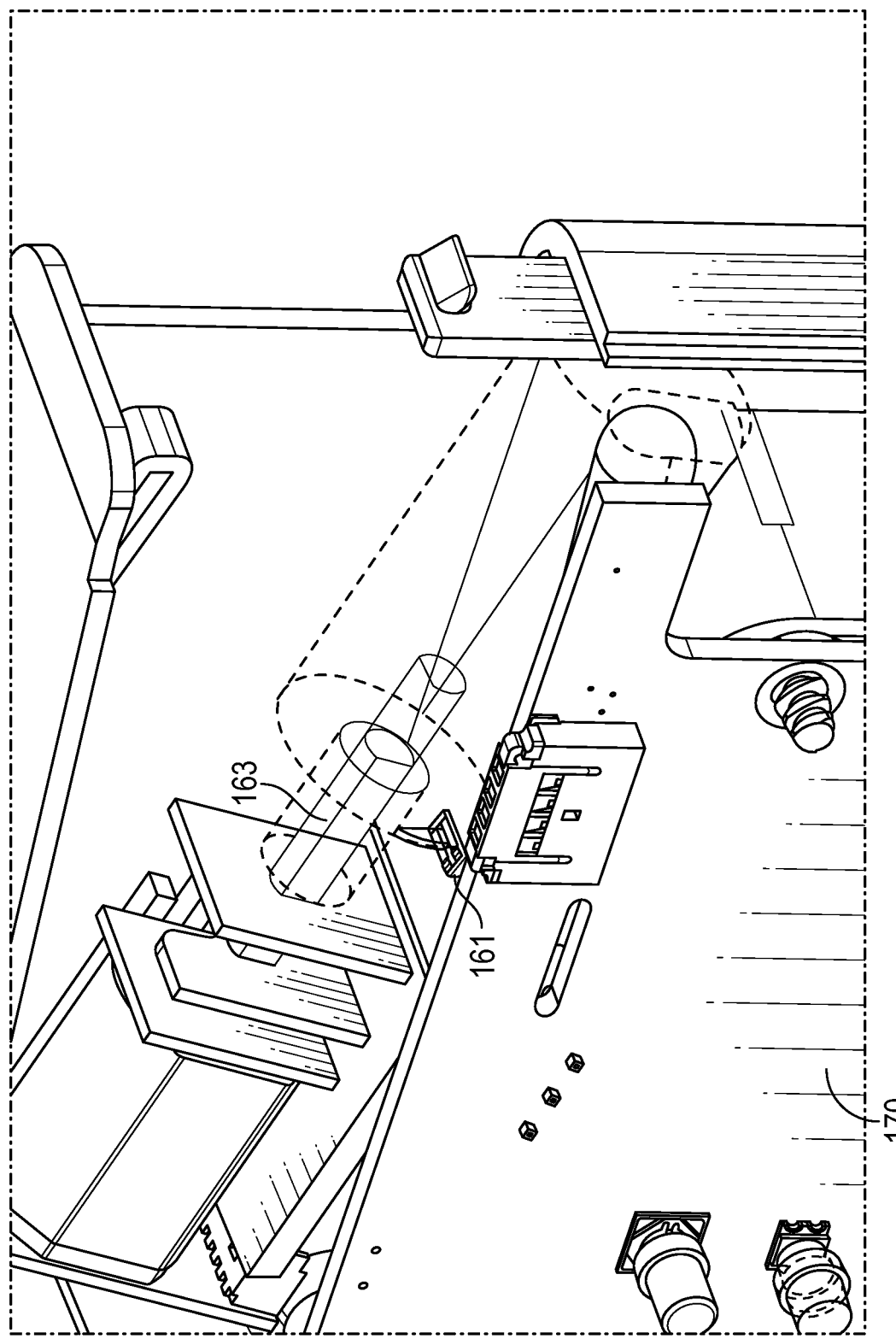
FIG. 31 depicts a portion of a portable pill dispenser in accordance with one or more embodiments of the disclosure.
Figure 32:
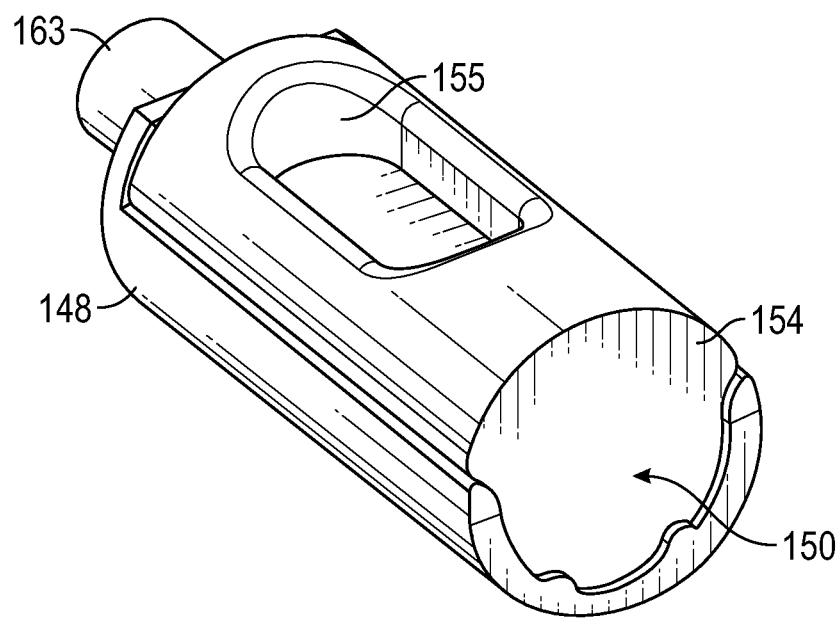
FIG. 32 depicts a removable insert of a portable pill dispenser in accordance with one or more embodiments of the disclosure.

In some instances, as depicted in FIGS. 29-31, a rotation sensor 161 is disposed within the housing 104 about a shaft 163 (or neck portion) of the rotating barrel 148. In one example, the rotation sensor 161 is attached to a ledge 167 extending from the control panel 170. The rotation sensor 161 is configured to detect the annular position of shaft 163 (or neck portion) of the rotating barrel 148. The rotation sensor 161 may be particularly useful in determining the location of the cavity 150. In some instances, the rotation sensor 161 is a trigger sensor (e.g., limit switch) that engages the shaft 163 (or neck portion) of the rotating barrel 148 as it rotates. Other types of rotation sensors 161 may be used, including, but not limited to, a magnetic sensor or a photo reflector sensor configured to detect a sticker or other indicia on the shaft 163 (or neck portion) of the rotating barrel 148. The rotation sensor 161 and the tachometer 164 may collectively determine the annular position of the shaft 163 (or neck portion) of the rotating barrel 148. In some instances, a tachometer, a limit switch, a photo reflective sensor, and/or a motor current sensor may be used to detect a "jam" and take appropriate action. For instance, if the motor current is high such that the rotating barrel should be spinning, and the photo reflective sensor and/or limit switch do not sense the barrel rotating, the motor may be instructed to run in reverse or to run back-and-forth several times. In addition, an error message may be displayed or a wireless signal may be sent to a smartphone or other companion electronic device.

Referring back to FIG. 1, the portable pill dispensing 100 includes a verification mechanism 166. The verification mechanism 166 is configured to activate, or permit activation of, the dispensing mechanism 134 upon verification of the identity of the user. In certain embodiments, the verification mechanism 166 comprises a biometric sensor 168. For example, the verification mechanism 166 may be a fingerprint reader, a retina reader, or the like. The biometric sensor 168 is disposed on the front portion 108 and includes a finger print reader. In other instances, the verification mechanism 166 may include a touch pad that a user enters a code (pin) or swipes a pattern. Any type of verification mechanism 166 may be used to limit and/or verify dispensing of the pills. In a preferred embodiment, the verification mechanism 166 will only enable the dispensing mechanism 134 to dispense a pill upon verifying the identity of the user. The verification information, e.g., pin, biometrics, etc., may be stored on the device or over a network. The portable pill dispensing 100 also may be in communication (wireless or hardwired) with a personal computing device, such as an app on a smart phone or the like, in which the user enters the verification information. In such instances, the verification mechanism 166 will only enable the dispensing mechanism 134 to dispense a pill upon verifying the identity of the user on the personal computing device. In some instances, the user can be anonymous for the purpose of the biometric verification (i.e. the biometric information stored on the device is not comparted to any known information about a particular person, and therefore, the identity of the user may be unknown other than the user is the owner of the biometric registered on the device.

As depicted in FIGS. 1 and 9-12, a control panel 170 is disposed within the housing 104. The control panel 170 comprises a printed circuit board having one or more electrical components thereon or in communication therewith. The control panel 170 includes a memory, circuitry, and at least one processor to execute the various functions described herein. In some instances, the electrical components of the control panel 170 are incorporated into the control panel 170 and/or are in electrical communication with the control panel 170. For example, the verification mechanism 166 and dispensing mechanism 134 are in electrical communication with the control panel 170. In addition, an accelerometer 172, one or more light indicators 174, a speaker 176, a mute button 178, a wireless communication module 180, an electrical connection port 182, one or more batteries 184, a battery charging connection port, an onboard internal clock, a vibration motor, and/or a geoposition transceiver (e.g., GPS transceiver) may also be in electrical communication with the control panel 170. The various electrical components may be disposed within the housing 104 and/or be accessible from outside of the housing 104.

The accelerometer 172 may determine the orientation of the portable pill dispenser 100. For example, in order to ensure the proper dispensing of the pills, the control panel 170 may not activate the dispensing mechanism 134 unless the portable pill dispenser 100 is in a substantially upright position as determined by the accelerometer 172. The speaker 176 (or other audible device) may provide alerts to the user, such as when to take their medication. The speaker 176 may provide any type of alert, including, but not limited to power alerts, verification alerts, unauthorized access alerts, dispensing alerts (including alerting the user that it is time to take their medication), incoming messages alerts, connectivity alerts, and/or change in medication regimen alerts, etc. The vibration motor also may similarly provide alerts to the user by vibrating the portable pill dispenser 100 when activated. The mute button 178 may enable to user to temporarily (or permanently) turn off (or mute) the alerts. The mute bottom 178 also may deactivate the vibration motor. The light indicators 174 may provide various alerts to the user, such as but not limited to, power alerts, verification alerts, unauthorized access alerts, dispensing alerts, incoming messages alerts, connectivity alerts, and/or change in medication regimen alters, etc. The light indicators 174 may be multi-colored LED lights. In some instances, the device may include a digital display, such as an LCD/LED display, on which textual or graphical information may be conveyed to the user. The batteries 184 may power the various electrical components. For example, a secondary battery 186 may power an internal clock associated with the control panel 170, while a primary battery 188 may power all of the other electrical components. In some instances, the internal clock ensures that the dose information is properly timestamped. The geoposition transceiver may enable tracking of the portable pill dispenser in cases of theft or loss. In addition, the geoposition transceiver may track the location where pills are being dispensed. The electrical connection port 182 and/or battery charging port may enable the portable pill dispenser 100 to be charged and/or connected to other devices or networks. In some instances, the electrical connection port 182 is a USB port or the like. Similarly, the wireless communication module 180 may enable the portable pill dispenser 100 to be connected to other devices or networks. In some instances, the wireless communication module may include Bluetooth capabilities, WIFI capabilities, satellite capabilities, a transmitter, or the like. The wireless communication module 180 may use any wireless communication protocol. The electrical connection port 182 and/or the wireless communication module 180 may enable the portable pill dispenser 100 to be connected to other devices for programming, troubleshooting, and/or data download.

Figure 13:
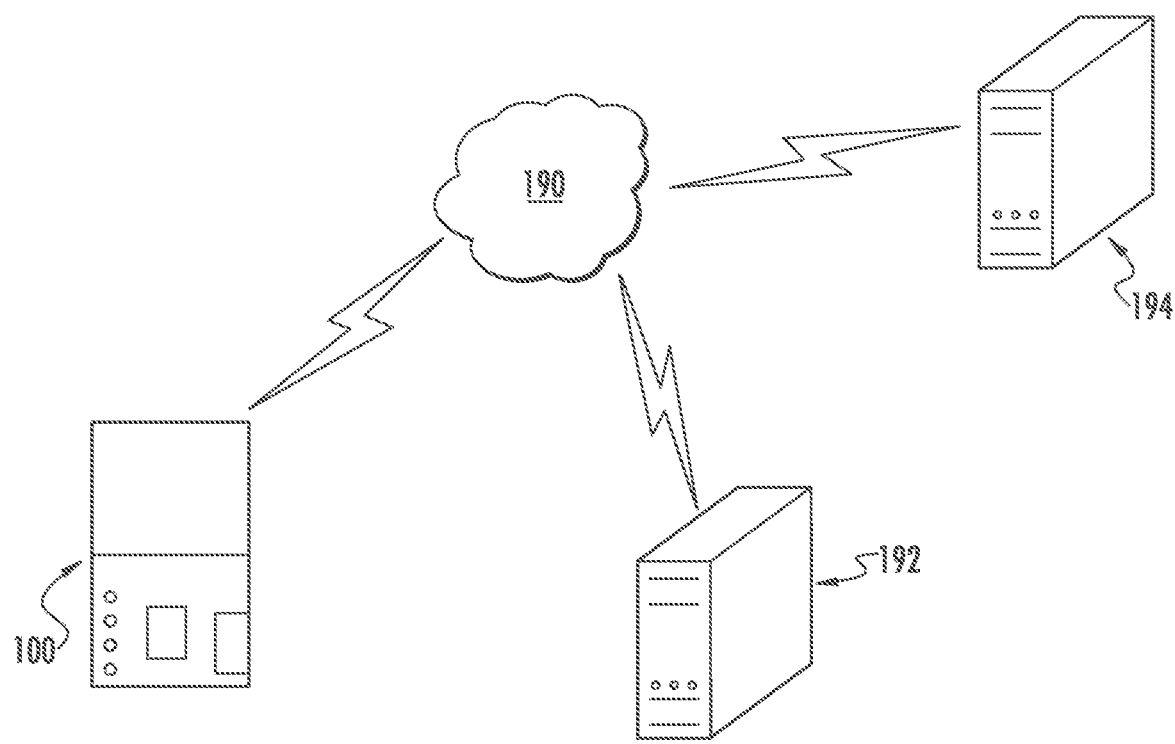
FIG. 13 depicts a communication network in accordance with one or more embodiments of the disclosure.
Figure 14:
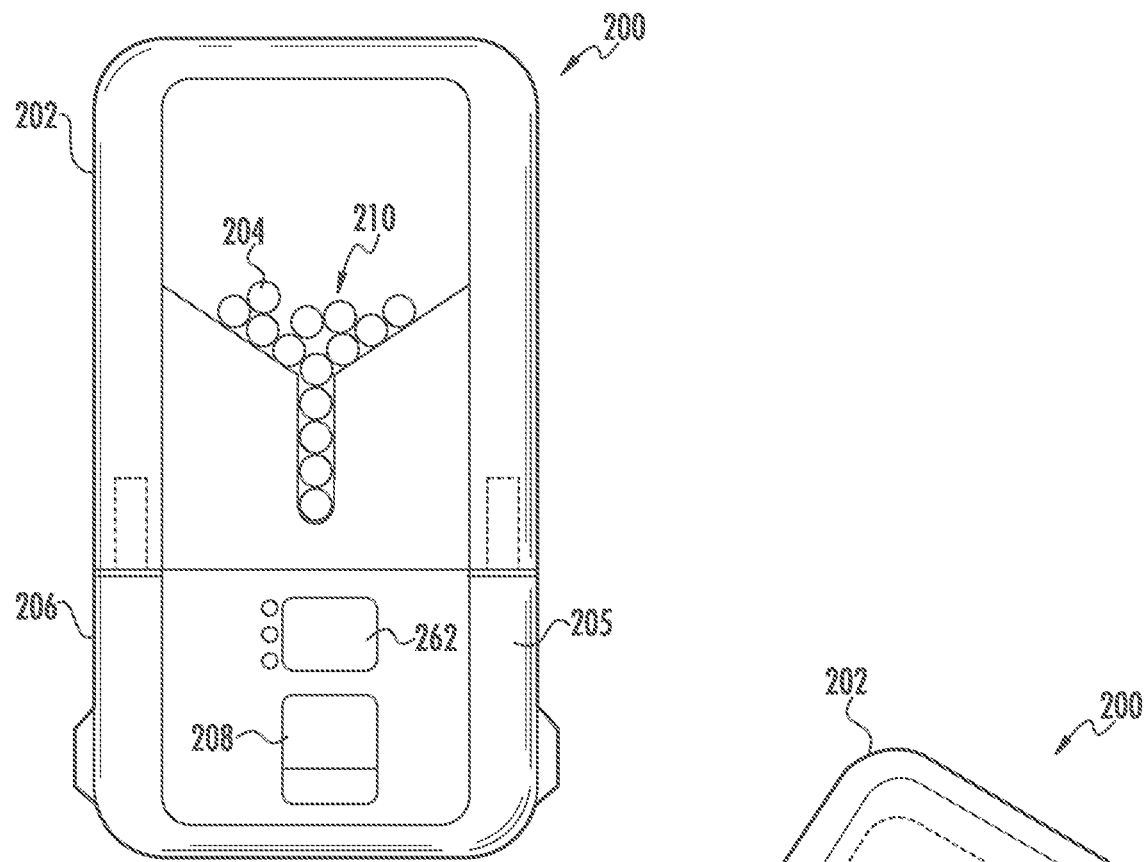
FIG. 14 depicts a portable pill dispenser in accordance with one or more embodiments of the disclosure.
Figure 15:
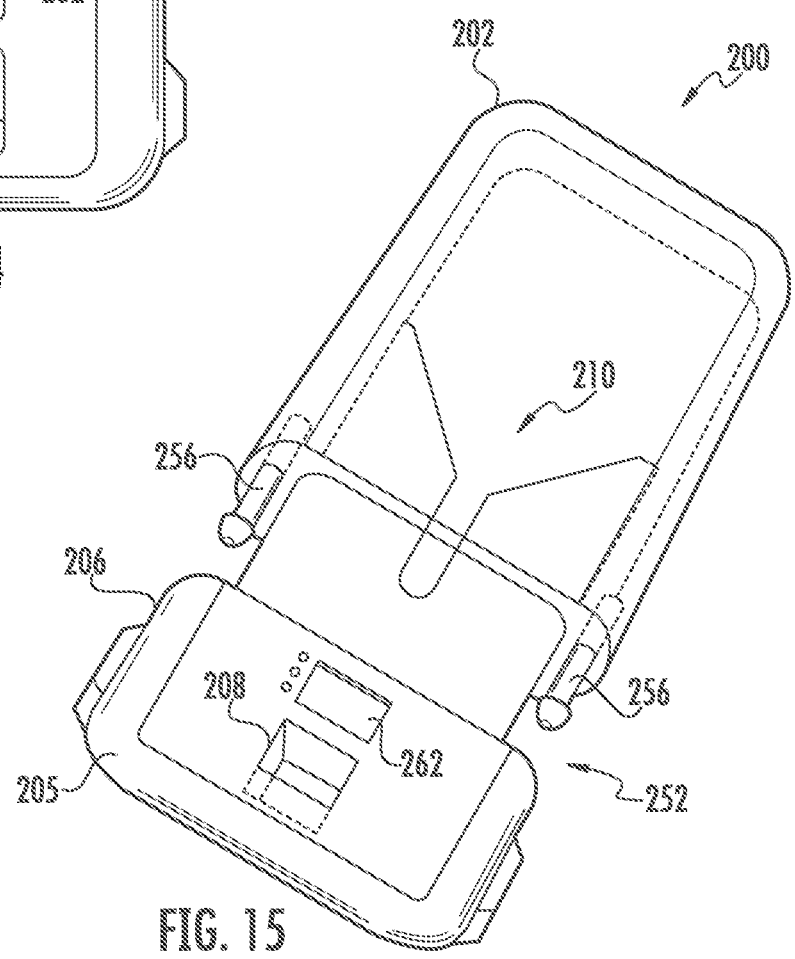
FIG. 15 depicts a portable pill dispenser in accordance with one or more embodiments of the disclosure.

FIG. 13 depicts the portable pill dispenser 100 communicating over a network 190. The portable pill dispenser 100 may include wireless capabilities. For example, the portable pill dispenser 100 may communicate over the network 190 with other devices by way of the wireless communication module 180. In other instances, the portable pill dispenser 100 may communicate over the network with other devices through a hard connection by way of the electrical communication port 182. The portable pill dispenser 100 may communicate with one or more computing devices 192 associated with a doctor's office, a hospital, a pharmacist, a caretaker, a clinical trial operator, etc. The portable pill dispenser 100 may communication with any suitable device or persons associated therewith. In addition, one or more third party computing devices 194 may monitor the portable pill dispenser 100 and/or collect information associated with the portable pill dispenser 100 over the network 190. In this manner, a medication regimen may be tracked to determine if it is being properly followed. Moreover, the medication regimen may be modified remotely. That is, the ability of the portable pill dispenser 100 to dispense pills may be adjusted remotely by a pharmacist, a caretaker, or a clinical trial operator, etc. In some instances, the portable pill dispenser 100 may communicate directly with a user device—such as a smart phone or the like associated with the user. The user device may then communicate the information from the portable pill dispenser 100 over the network 190.

FIGS. 14-24 depict additional embodiments of a portable pill dispenser 200. The embodiments described in FIGS. 14-24 may be incorporated into any of the embodiments described in FIGS. 1-13 and vice versa. The portable pill dispenser 200 may include a container 202 configured to house one or more pills 204 therein. In some instances, the container 202 is reusable or disposable. The portable pill dispenser 200 also may include a housing 205 attachable to the container 202. The housing 205 may include a dispensing mechanism 206 therein. Any type of dispensing mechanism 206 may be used. The dispensing mechanism 206 may be configured to dispense at least one of the pills 204 from the container 202 to a dispensing opening 208. In some instances, the housing 205 is reusable. That is, once the pills 204 have been dispensed, the disposable container 202 may be removed from the housing 205 and a new disposable container 202 may be attached thereto.

The container 202 may include a container label. For example, the container 202 may include a prescription label thereon. The prescription label may identify the pills therein, provide instructions to the patient, provide a medication regimen, provide patient information, provide doctor information, provide warnings, and/or provide emergency instructions, or the like. The information may be in the form of text and/or a barcode. Any information may be included on the container and/or label.

In some instances, the container 202 may include a data chip (or other electronic storage device, such as a memory card or the like). The data chip may include any information included in the prescription label. The information associated with the data chip may be encrypted. In some instances, the container 202 and/or the housing 205 may include an electronic display, which may display information from the data chip. In addition, the data chip may provide information (such as pill type, a medication dosage regimen, etc.) to a controller associated with the dispensing mechanism 206 so as to control the dispensing of the pills 204. In this manner, the container 202 may communicate (wirelessly and/or by way of a direct connection) to the dispensing mechanism 206.

In certain embodiments, the container 202 and/or the housing 205 may include a radio with any suitable transceiver component(s) for transmitting or receiving radio frequency (RF) signals. In this manner, the portable pill dispenser 200 may include wireless capabilities. The portable pill dispenser 200 may be WIFI, cellular, satellite, or the like compatible. For example, the portable pill dispenser 200 may communicate over a network with other devices. For example, the portable pill dispenser 200 may communicate with one or more computing devices associated with a doctor's office, a hospital, a pharmacist, a caretaker, a clinical trial operator, etc. The portable pill dispenser 200 may communicate with any suitable device or persons associated therewith. In addition, third parties may monitor the portable pill dispenser 200 and/or collect information associated with the portable pill dispenser 200 over a network. For example, a medication regimen may be tracked to determine if it is being properly followed. The medication regimen also may be modified remotely.

A funnel 210 may be configured to direct at least one of the pills 204 to the dispensing mechanism 206. In certain embodiments, as depicted in FIG. 18, the funnel 210 includes a first arm 212 and a second arm 214. In some instances, the first arm 212, the second arm 214, or both are adjustable relative to each other in order to adjust a funnel opening 216 therebetween. In this manner, the funnel 210 may be adjusted to allow one pill 204 at a time through the funnel opening 216. For example, the first arm 212, the second arm 214, or both may comprise a respective funnel slot 218 slidably positioned about a respective funnel peg 220. In this manner, the first arm 212 and/or the second arm 214 may be adjusted by sliding the first arm 212 and/or the second arm 214 about the respective funnel peg 220. The first arm 212 and/or the second arm 214 may be adjusted to accommodate different pill sizes. In other instances, one or both of the funnel arms may be fixed. In yet other instances, the funnel 210 may be omitted.

In certain embodiments, as depicted in FIGS. 23 and 24, the funnel 210 may include a torturous path 211 to ensure that certain pills 204 are properly oriented for dispensing. For example, elongated pills 213 may not pass through the torturous path 211 unless oriented in a certain configuration, such as sideways. In some instances, the torturous path 211 may include a winding path with several switchbacks leading to the funnel opening 216. The winding path may only enable pills in a certain orientation to pass through the funnel 210 to the funnel opening 216. In some instances, a user may shake the portable pill dispenser 200 to jostle the pills 204 into the proper orientation so that they can pass down the torturous path 211. In some instances, the torturous path 211 may form the funnel 210. In other instances, the torturous path 211 may direct pills 204 to the funnel 210. In yet other instances, the funnel 210 may direct pills 204 to the torturous path 211.

Referring back to FIG. 18, the portable pill dispenser 200 may include an agitation device 222 in communication with at least one of the first arm 212, the second arm 214, or a combination thereof to impart motion thereto. For example, the agitation device 222 may be a ratchet gear that rotates to vibrate or otherwise move the first arm 212 and/or the second arm 214. The agitation device 222 may ensure the one or more pills 204 slide down the funnel 210. In some instances, the agitation device 222 is adjustable. For example, the agitation device 222 may include a hub 224 slidably positioned within an agitation slot 226. The agitation device 222 may be adjusted by sliding the hub 224 about the agitation slot 226. In this manner, the agitation device 222 may be adjusted to accommodate different pill sizes and/or funnel arrangements. In some instances, the agitation device 222 may be omitted.

In certain embodiments, the dispensing mechanism 206 comprises a first rotatable hub 228 and a second rotatable hub 230 positioned about the funnel opening 216. In some instances, the first rotatable hub 228, the second rotatable hub 230, or both are adjustable relative to each other in order to adjust a rotatable hub opening 232 therebetween. For example, the first rotatable hub 228 and/or the second rotatable hub 230 may be slidably positioned about a respective rotatable hub slot 234. In this manner, the first rotatable hub 228 and/or the second rotatable hub 230 may be adjusted by sliding the first rotatable hub 228 and/or the second rotatable hub 230 about the respective rotatable hub slot 234. The first rotatable hub 228 and/or the second rotatable hub 230 may be adjusted to accommodate different pill sizes. Rotation of the first rotatable hub 228 and the second rotatable hub 230 may move at least one of the one or more pills 204 from the funnel opening 216 to the dispensing opening 208. In some instances, the dispensing mechanism 206 dispenses one pill at a time.

Figure 17:
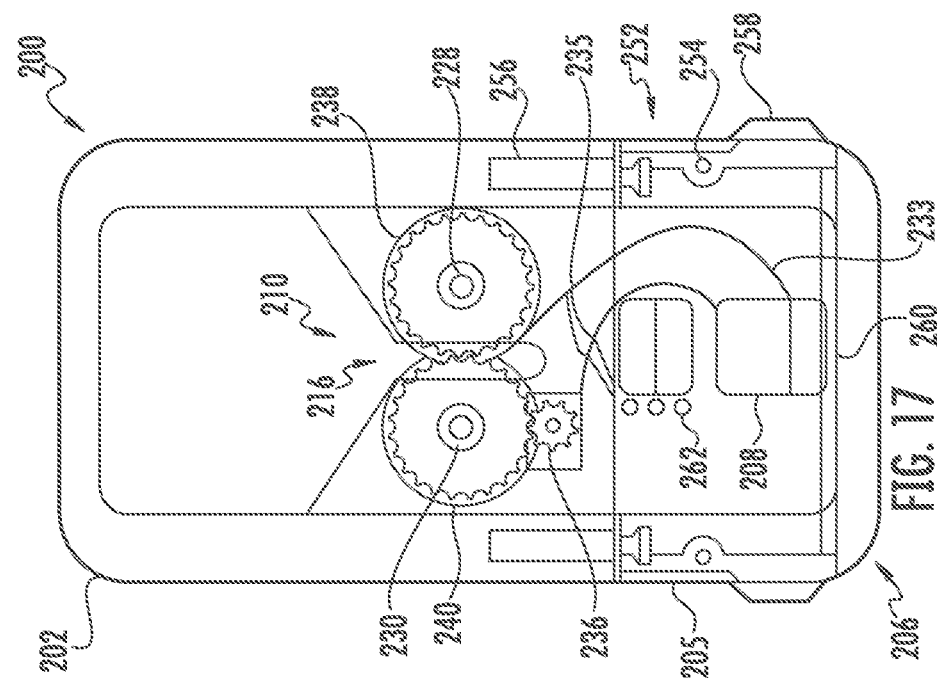
FIG. 17 depicts a portable pill dispenser in accordance with one or more embodiments of the disclosure.
Figure 16:
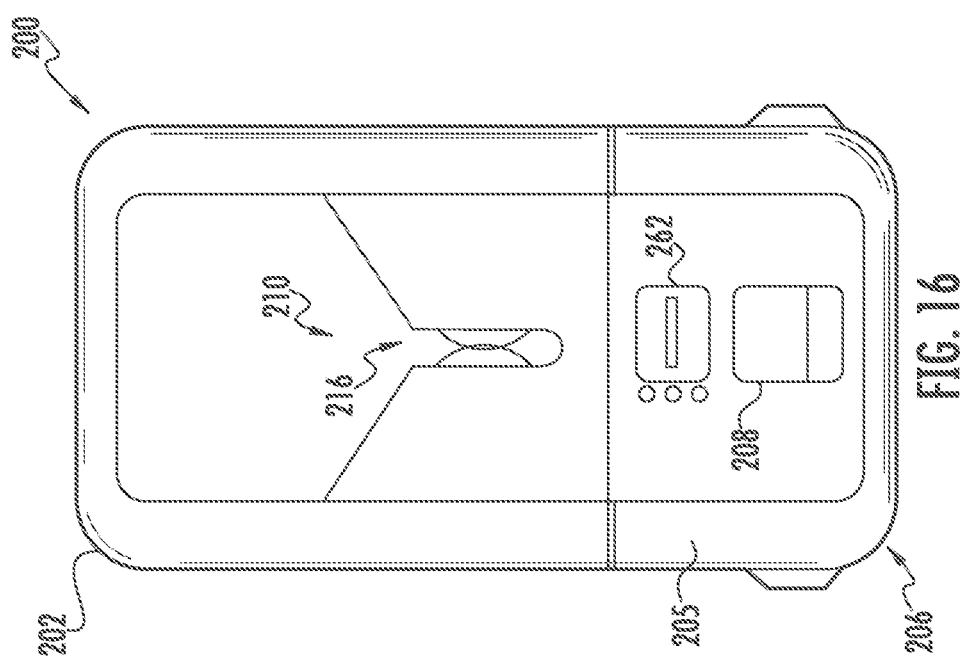
FIG. 16 depicts a portable pill dispenser in accordance with one or more embodiments of the disclosure.

As depicted in FIG. 17, a passageway 233 may be disposed between the first rotatable hub 228 and the second rotatable hub 230 and the dispensing opening 208. In this manner, the first rotatable hub 228 and the second rotatable hub 230 may move at least one of the one or more pills 204 from the funnel opening 216 to the passageway 233. For example, the dispensing mechanism 206 dispenses one pill at a time. In some instances, the passageway 233 includes a lever 235 that blocks pills from reaching the dispensing opening 208. As discussed below, the lever 235 may pivot to allow the pills to travel down the passageway 233 to the dispensing opening 208 once the user and/or medication regimen has been verified.

Referring back to FIG. 18, in some instances, the first rotatable hub 228, the second rotatable hub 230, or a combination thereof are in mechanical communication with the agitation device 222. In this manner, rotation of the first rotatable hub 228, the second rotatable hub 230, and/or the agitation device 222 may drive (e.g., rotate) the others or vice versa. Moreover, in certain embodiments, as depicted in FIG. 17, a drive wheel 236 is in mechanical communication with at least one of the first rotatable hub 228, the second rotatable hub 230, and/or the agitation device 222. In addition, the drive wheel 236 may be in mechanical communication with a motor or the like. The drive wheel 236 may impart motion (directly or indirectly) to the first rotatable hub 228, the second rotatable hub 230, and/or the agitation device 222. In other instances, the motor 225 may be attached directly to the first rotatable hub 228, the second rotatable hub 230, and/or the agitation device 222. In some instances, the motor may be an electric motor in communication with a battery. A controller may be in communication with the battery and/or the motor to control the dispensing process.

In some instances, as depicted in FIG. 18, a first foam wheel 238 is positioned about the first rotatable hub 228. Similarly, a second foam wheel 240 may be positioned about the second rotatable hub 230. The first foam wheel 238 and the second foam wheel 240 may facilitate dispensing of at least one of the one or more pills 204 by the first rotatable hub 228 and the second rotatable hub 230. For example, the foam wheels may be elastically deformable to encase a pill and transfer the pill through the interface of the two rotating wheels. In some instances, the dispensing mechanism 206 dispenses one pill at a time. The first foam wheel 238 and the second foam wheel 240 may be the same or different sizes. In some instances, the first foam wheel 238 and/or the second foam wheel 240 may be omitted.

Figure 19:
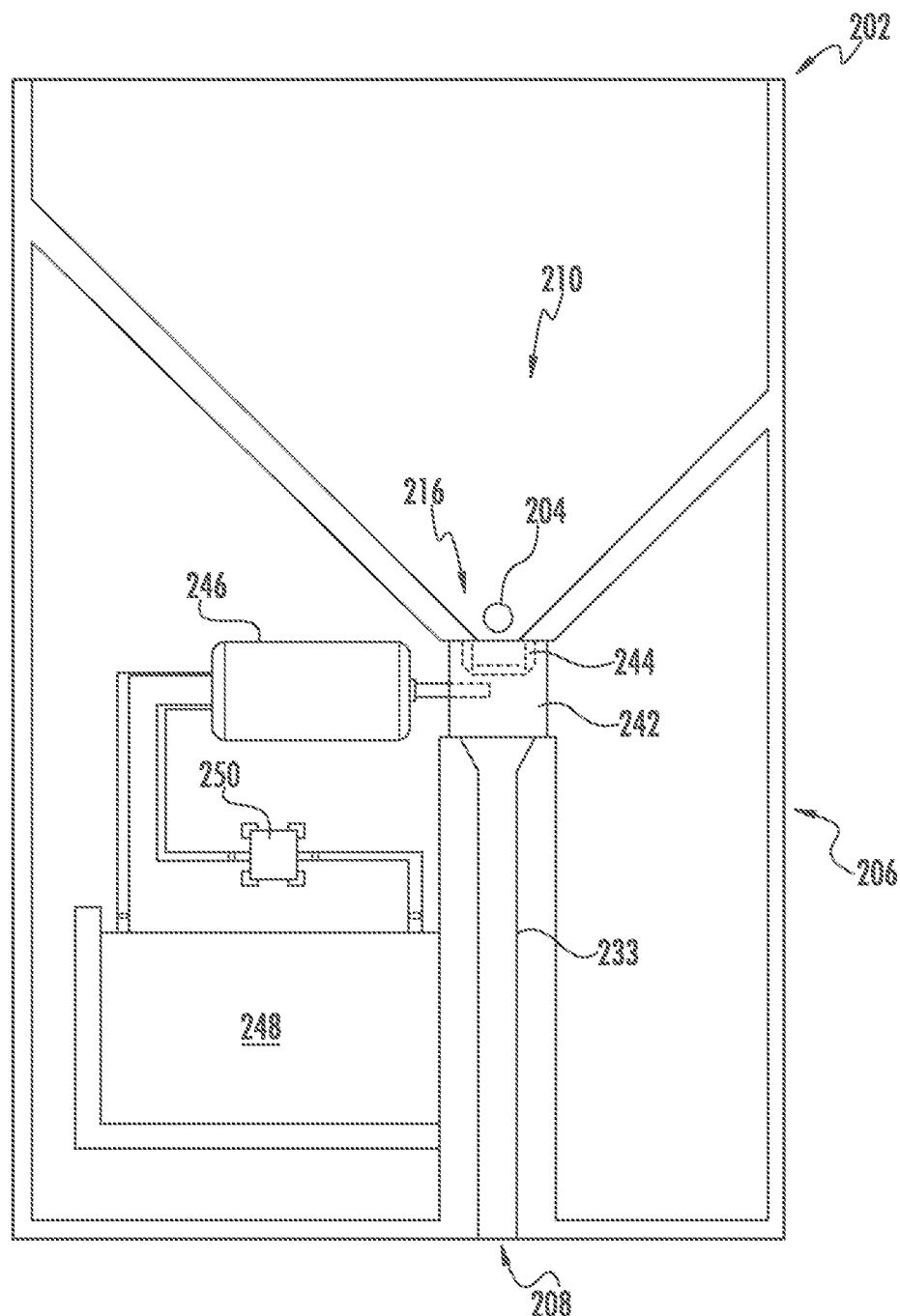
FIG. 19 depicts a dispensing mechanism of a portable pill dispenser in accordance with one or more embodiments of the disclosure.
Figure 20:
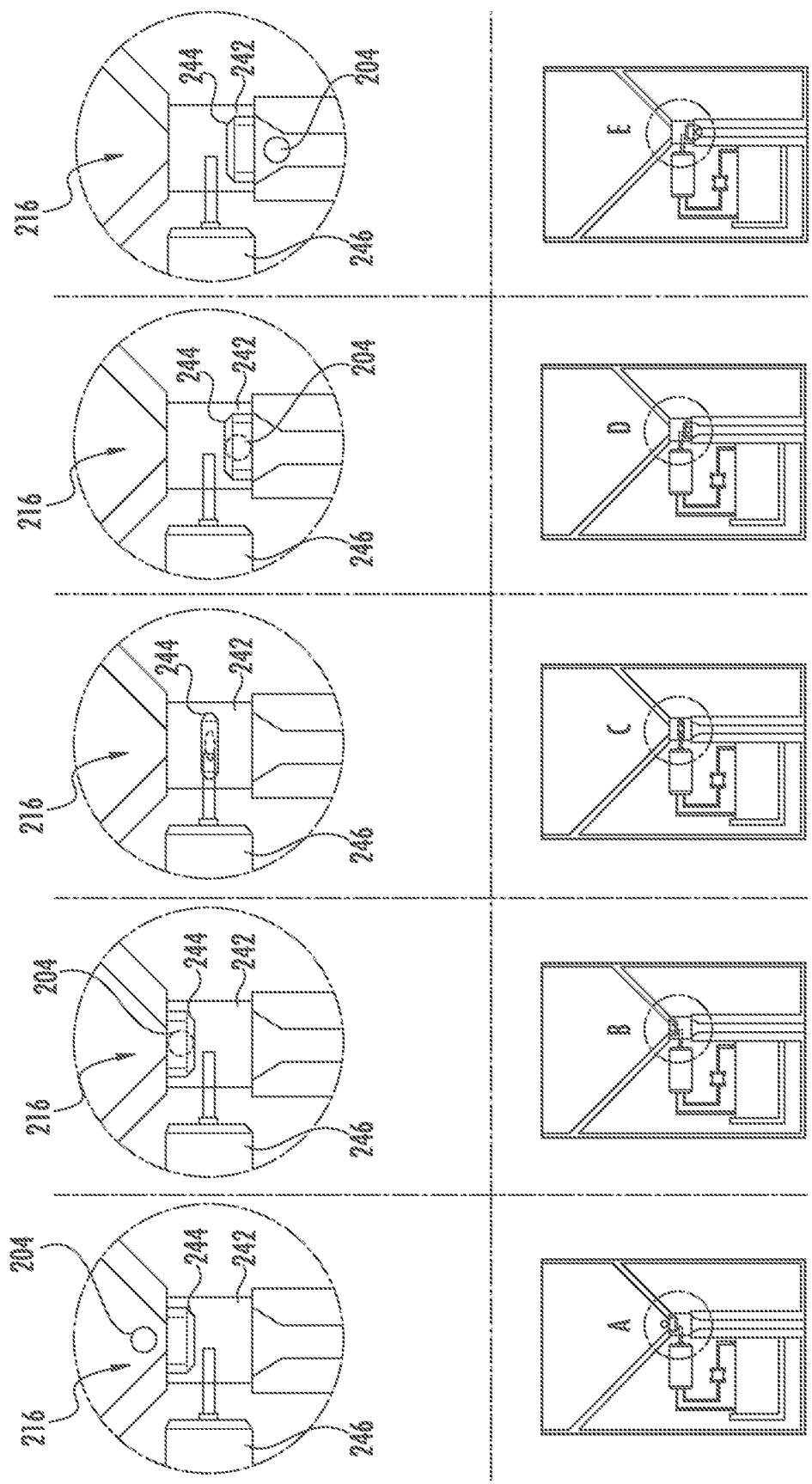
FIG. 20 depicts a dispensing sequence in accordance with one or more embodiments of the disclosure.
Figure 21:
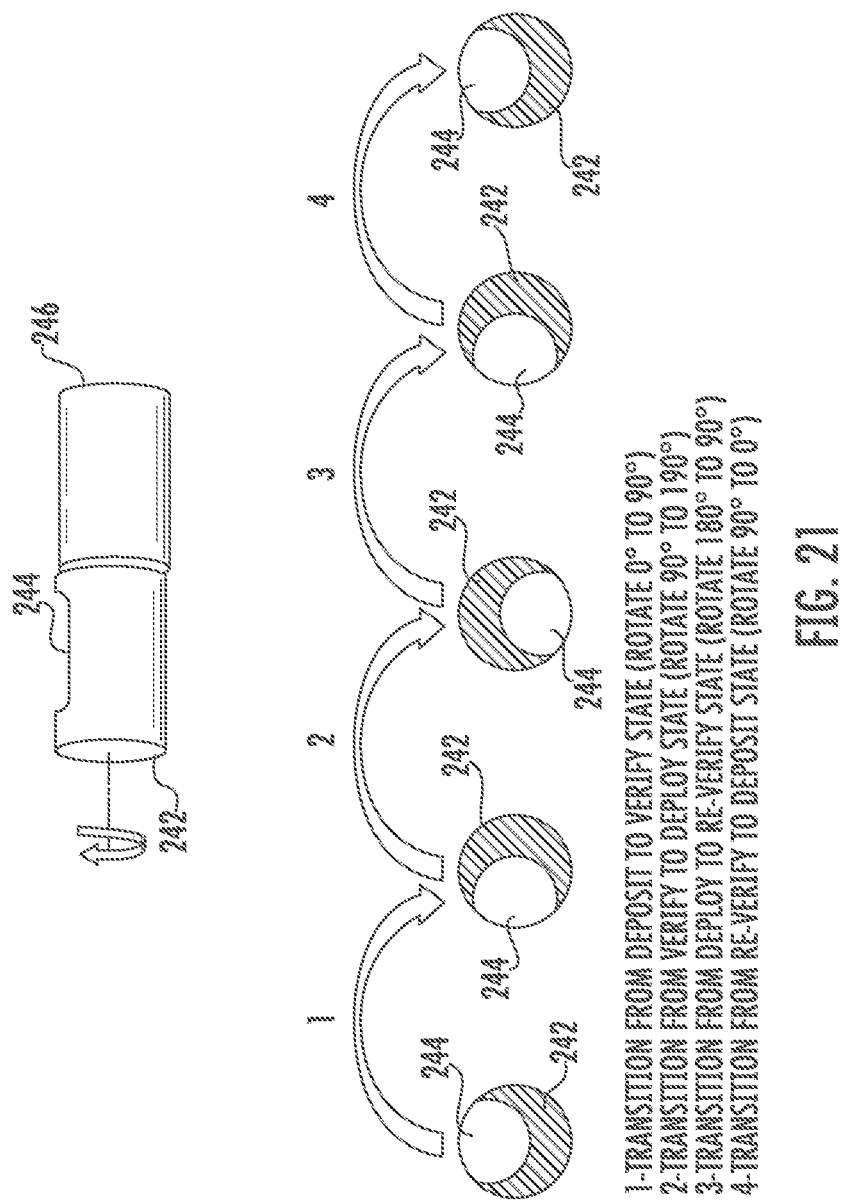
FIG. 21 depicts a dispensing sequence in accordance with one or more embodiments of the disclosure.

In another embodiment, as depicted in FIGS. 19-21, the dispensing mechanism 206 includes a rotating barrel 242 positioned about the funnel opening 216. The rotating barrel 242 may include at least one cavity 244 configured to receive at least one of the one or more pills 204 therein from the funnel opening 216. In some instances, a number of cavities 244 may be disposed within the rotating barrel 242. The at least one cavity may be sized to fit one pill therein. In this manner, the dispensing mechanism 206 may dispense one pill at a time. The rotating barrel 242 may rotate the at least one cavity 244 from the funnel opening 216 to the dispensing opening 208. In this manner, rotation of the barrel 242 may move at least one of the one or more pills 204 from the funnel opening 216 to the dispensing opening 208. As noted above, a torturous path 211 may be incorporated to ensure that the pills 204 are in the proper orientation for dispensing into the at least one cavity 244 in the rotating barrel 242. In some instances, a passageway 233 may be positioned between the rotating barrel 242 and the dispending opening 208. The dispensing mechanism 206 may include a motor 246 in direct or indirect (e.g., via one or more gears) mechanical communication with the rotating barrel 242. In some instances, the motor 246 may be an electric motor in communication with a battery 248. A controller 250 may be in communication with the battery 248 and/or the motor 246 to control the dispensing process. FIGS. 20 and 21 depict the rotating barrel 242 making a full rotation to dispense one of the pills 204.

Referring back to FIGS. 14-17, the portable pill dispenser 200 may include an attachment mechanism 252 configured to secure the container 202 to the housing 205. In some instances, the attachment mechanism 252 comprises at least one pivoting lever 254 positioned about the housing 205. The at least one pivoting lever 254 may be configured to mate with at least one pin 256, which may be disposed about the container 202. The at least one pivoting lever 254 may include a release bottom portion 258. In some instances, a tool may be required to detach the container 202 from the housing 205. For example, a lock pin shear bar 260 may prevent the container 202 from detaching from the housing 205. In this manner, only an authorized person (such as a pharmacist) may detach the container 202 from the housing 205. Any type of tamper resistance attachment mechanism may be used herein.

In addition, a verification mechanism 262 may be configured to verify access to the dispensing opening 208 and/or activate the dispensing mechanism 206. That is, the verification mechanism 262 may provide access to the dispensing opening 208 only to a verified user and/or may activate the dispensing mechanism 206 only upon verification of the user. In some instances, the verification mechanism 262 is a biometric locking mechanism. For example, the verification mechanism 262 may be a fingerprint reader, a retina reader, or the like. In other instances, the verification mechanism 262 may include a touch pad into which a user enters a code. Any type of verification mechanism may be used herein to limit and/or verify access to the dispensing opening 208.

The portable pill dispenser 200 may include one or more sensors disposed about the container 202, the housing 205, and/or the dispensing mechanism 206. For example, the one or more sensors may be disposed within the container 202 to detect the presence of the one or more pills 204. The one or more sensors also may be positioned adjacent to the dispensing mechanism 206 (on the funnel side and/or the dispensing opening side) to detect whether, and how many pills, have been dispensed. In addition, the one or more sensors may be disposed about the dispensing opening 208. The one or more sensors may be configured to detect the presence of at least one of the one or more pills at any of the stages of the dispensing process. In one embodiment, the detection mechanism is based on light reflection from the pill compared to light reflection from the dispensing mechanism (barrel). The wavelength of light is chosen to maximize the signal difference between the pill and the dispenser. By way of example, the dispenser can be optimized to maximally reflect the chosen wavelengths of light while the pill maximally absorbs the chosen wavelengths of light. Various mechanisms that can be used to maximize the differences in absorption or reflection of light can include reflection, refraction, light scatter, light diffusion, surface textures, dispenser color, dispenser material choice, dispenser coatings, material fluorescence, and the like.

Figure 22:
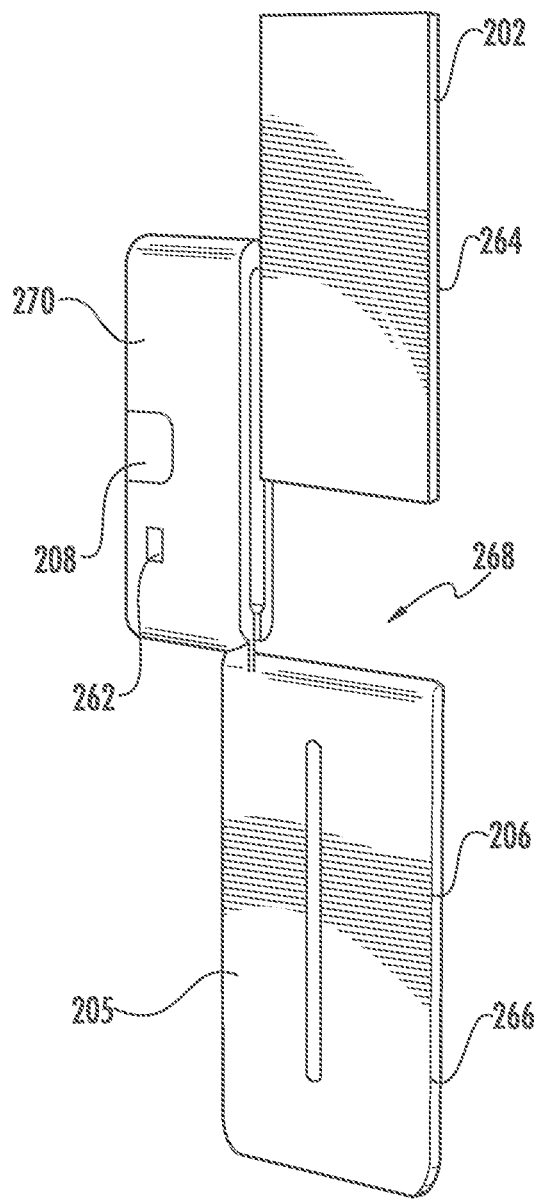
FIG. 22 depicts a portable pill dispenser in accordance with one or more embodiments of the disclosure.

In certain embodiments, as depicted in FIG. 22, the container 202 may be disposed within the housing 205. For example, the container 202 may take the form of a cartridge 264 that is disposed within the housing 205. For example, the housing 205 may include an outer shell 266 with an opening 268. The opening 268 may be covered by a pivoting lid 270. The cartridge 264 may be inserted into the opening 268 and the lid 270 may be pivoted shut. The lid 270 may be secured shut by any resistant proof attachment means. The container 202 and the housing 205 may be arrangement in any manner.

FIGS. 25-28 depict a dispensing mechanism 300 for a portable pill dispenser. The dispensing mechanism 300 may be incorporated into the embodiments described herein. In particular, the dispensing mechanism 300 may replace or work in conjunction with the dispensing mechanism 134 in FIGS. 1-13. In some instances, the container 303 and the housing 307 may be similar to those described in FIGS. 1-13. The dispensing mechanism 300 may be incorporated into any pill dispenser.

A ramp 302 is configured to guide the pills 304 from a container 303 to the dispensing mechanism 300. The dispensing mechanism 300 may dispense the pills 304 to a dispensing opening 305 in the housing 307. In some instances, the ramp 302 guides one pill at a time to the dispensing mechanism 300. That is, the ramp 302 is sized and shaped to align one pill into the dispensing mechanism 300 at a time. In other instances, the ramp 302 may permit a plurality of pills 304 into the dispensing mechanism 300 at once. The ramp 302 may be attached to the support wall 309, which may be attached to the housing 307. In other instances, the ramp 302 may be directly attached to the housing 307. The ramp 302 includes an inlet 306 facing the container and an outlet 308 downstream of the dispensing mechanism 300. The size and shape of the inlet 306 and the outlet 308 may vary depending on the pills being dispensed. The ramp 302 may include one or more angled portions so as to use gravity to cause the pills to slide into the dispensing mechanism 300. For example, the ramp 302 may function as a funnel directing one or more pills to the dispensing mechanism 300. The ramp 302 may be any suitable size, shape, or configuration.

The dispensing mechanism 300 is configured to dispense the pills 304 from the container 303. In some instance, the dispensing mechanism 300 comprises an oscillating member 310. The oscillating member 310 is configured to pivot about a pivot point 312. For example, the oscillating member 310 includes an elongated platform 314 pivoting about the pivot point 312. The elongated platform 314 may include a forward lip 316 and a rear lip 318. In some instances, the forward lip 316 and the rear lip 318 are disposed on opposite sides of the pivot point 312 at opposite ends of the elongated platform 314. The forward lip 316 and the rear lip 318 may be disposed on opposite sides of the pivot point 312 at any location about the elongated platform 314. The forward lip 316 and the rear lip 318 move up-and-down as the elongated platform 314 oscillates back-and-forth, i.e., as the elongated platform 314 rotates about the pivot point 312. That is, as the forward lip 316 rises, the rear lip 318 lowers, and vice versa.

The forward lip 316 may move up-and-down about the outlet 308, and the rear lip 318 may move up-and-down through an opening 320 in the ramp 302. In some instances, the distance between the forward lip 316 and the rear lip 318 may accommodate a single pill therebetween. In other instances, two or more pills may fit between the forward lip 316 and the rear lip 318. In order to accommodate pills of varying sizes and/or shapes, the size and shape of the oscillating member 310 may vary. For example, the width and distance between the forward lip 316 and the rear lip 318 may vary. In this manner, depending of the pills being dispensed, different sized and/or shaped oscillating members 310 may be used. In this manner, the dispensing mechanism 300 may be customized for different pills.

Figure 25:
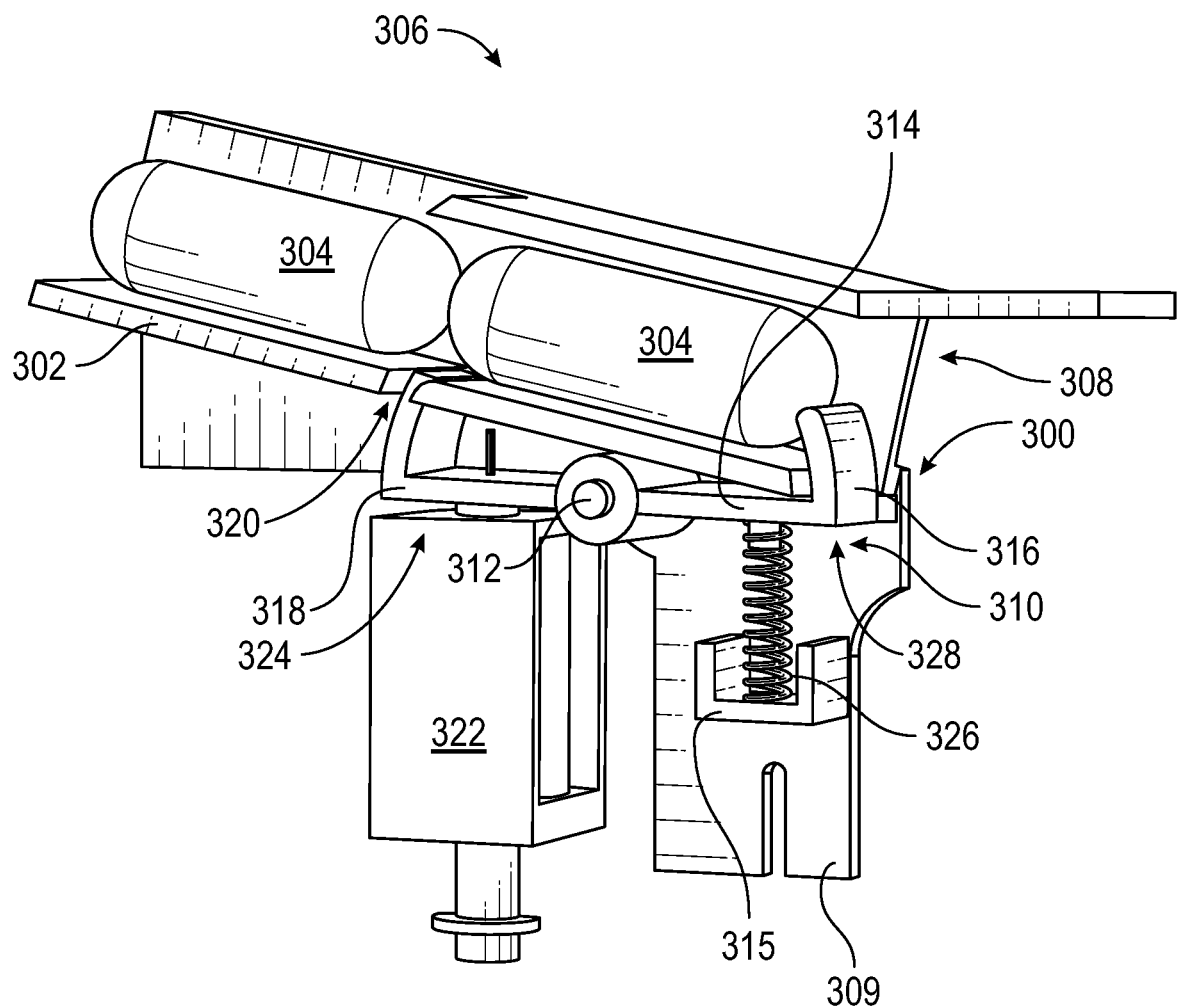
FIG. 25 depicts a dispensing mechanism comprising an oscillating member for a portable pill dispenser in accordance with one or more embodiments of the disclosure.
Figure 26:
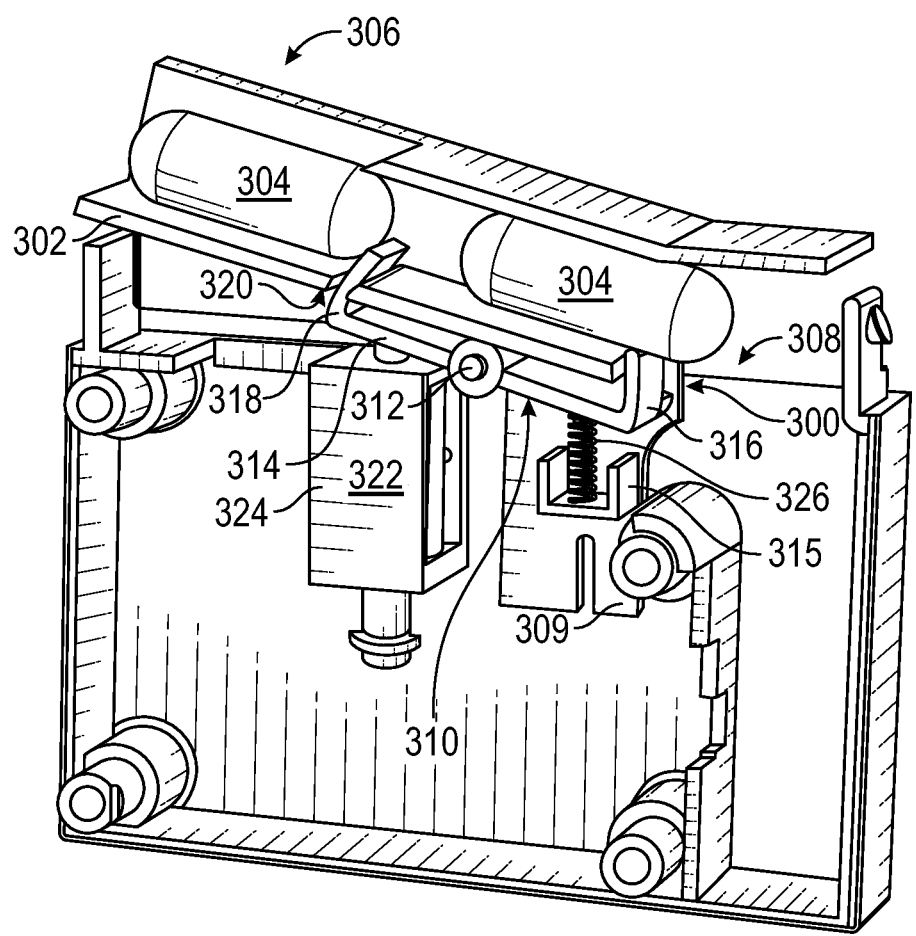
FIG. 26 depicts a dispensing mechanism comprising an oscillating member for a portable pill dispenser in accordance with one or more embodiments of the disclosure.
Figure 27:
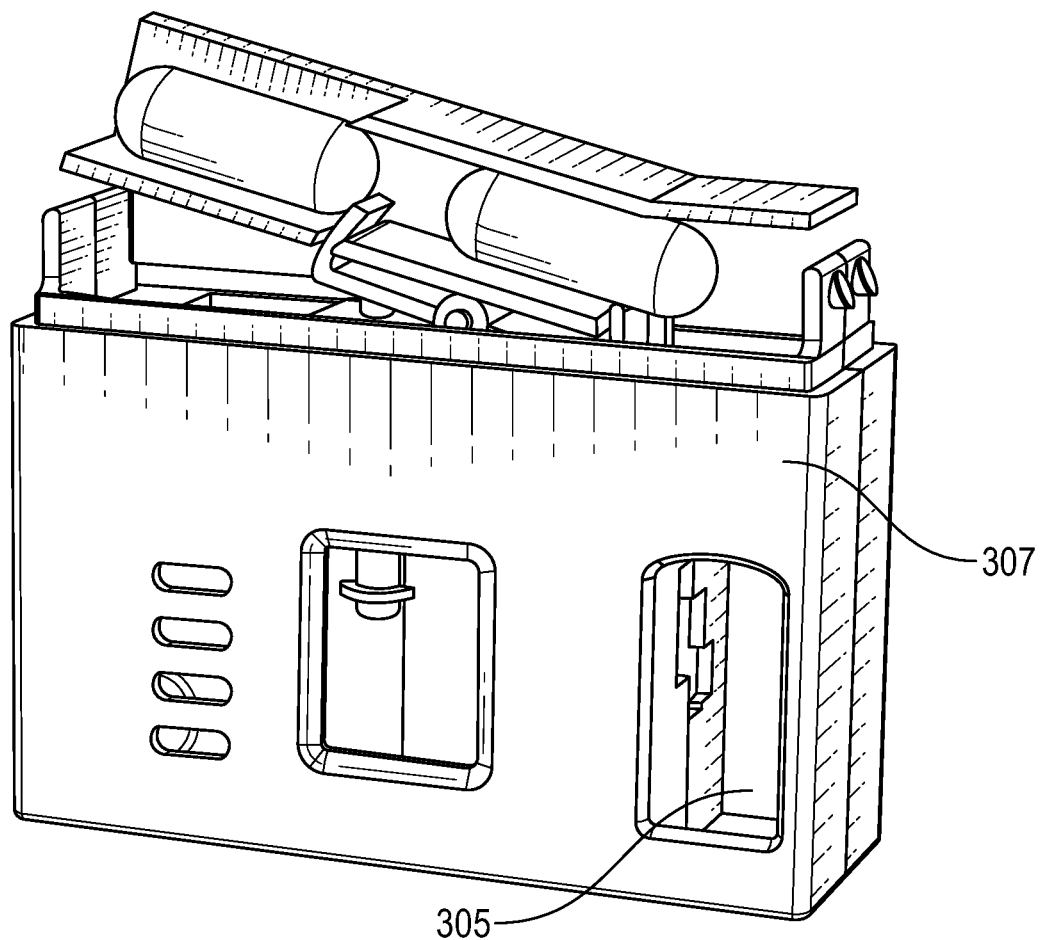
FIG. 27 depicts a dispensing mechanism comprising an oscillating member for a portable pill dispenser in accordance with one or more embodiments of the disclosure.
Figure 28:
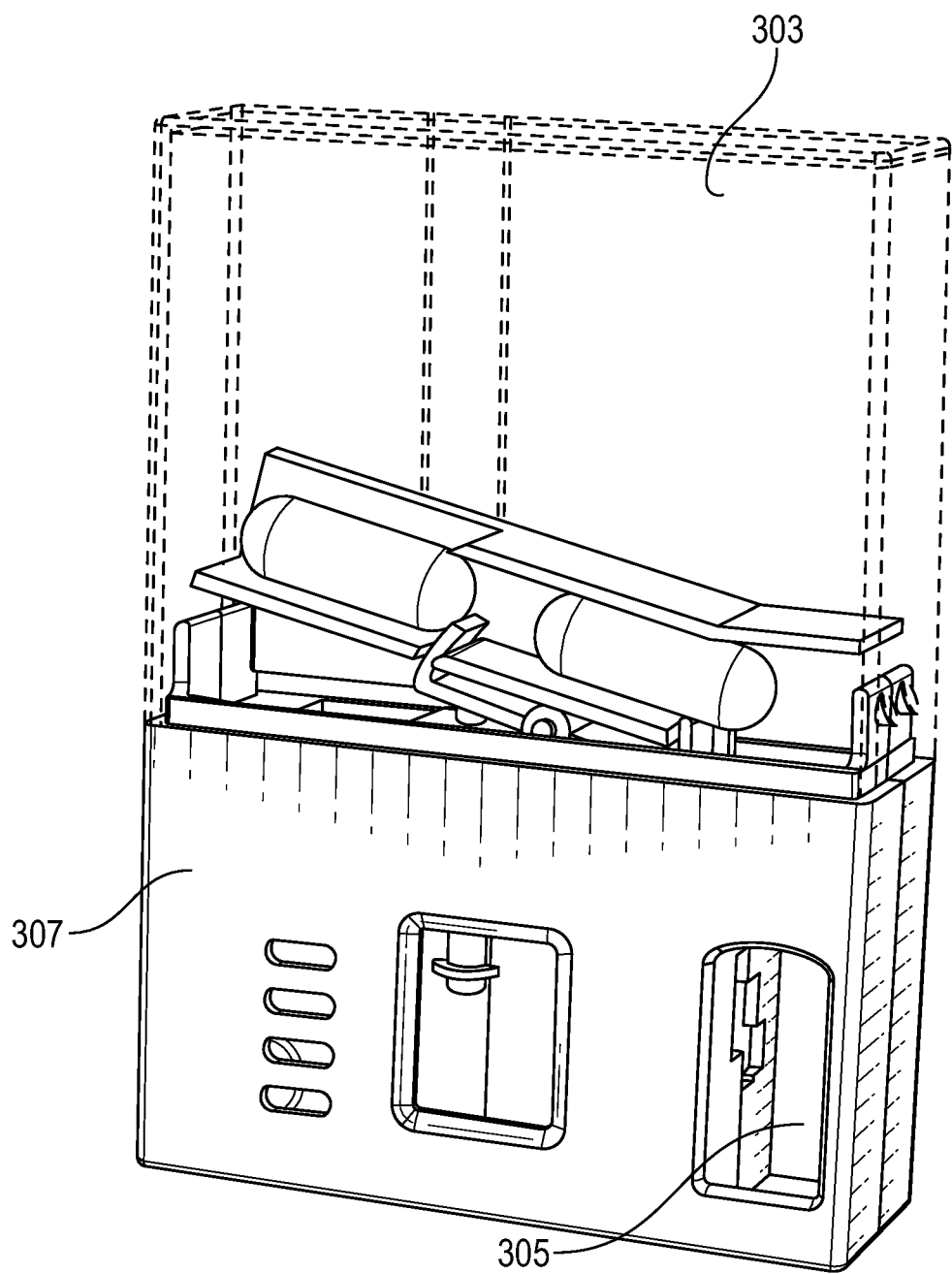
FIG. 28 depicts a dispensing mechanism comprising an oscillating member for a portable pill dispenser in accordance with one or more embodiments of the disclosure.

An actuator 322 may be in mechanical communication with the elongated platform 314 on a first side 324 of the pivot point 312 about the rear lip 318, and a spring 326 may be in mechanical communication with the elongated platform 314 on a second side 328 of the pivot point 312 about the forward lip 316. In some instances, the spring 326 may be supported by a ledge 315 extending from the support wall 309, which may be attached to the housing 307. As a result, as depicted in FIG. 25, the forward lip 316 is biased in the upward position to prevent the pills 304 from being dispensed. In order to lower the forward lip 316, as depicted in FIG. 26, the actuator 322 pivots the elongated platform 314 to overcome the resistance of the spring 326. The location of the actuator 322 and the spring 326 may be reversed. That is, the actuator 322 and the spring 326 may be switched. In some instances, the actuator 322 may be a linear actuator. Any suitable actuator may be used. The actuator 322 may be in direct or indirect (e.g., via one or more gears) mechanical communication with the oscillating member 310.

The actuator 322 and the oscillating member 310 may be positioned beneath the ramp 302. In this manner, the oscillating member 310 is positioned about the outlet 308 of the ramp 302. When the actuator 322 pivots the elongated platform 314 to overcome the resistance of the spring 326, as depicted in FIG. 26, the forward lip 316 is lowered, which enables one or more pills disposed between the rear lip 318 and the forward lip 316 to be dispensed. In addition, as the forward lip 316 is lowered, the rear lip 318 is pushed upward, which blocks additional pills from being dispensed. When the actuator 322 is deactivated, as depicted in FIG. 25, the spring 326 pivots the elongated platform 314 in the opposite direction, which forces the forward lip 316 upward to prevent the pills 304 from being dispensed. In addition, as the forward lip 316 is raised, the rear lip 318 is lowered to enable one or more pills 304 to slide between the forward lip 316 and the lower lip 318 for subsequent dispensing the next time the forward lip 316 is lowered.

Oscillating member 310 may move back-and-forth and up-and-down on demand. That is, the actuator 322 may be activated by a CPU upon verification of the identity of the user. The actuator 322 may move the oscillating member 310 at regular or irregular intervals or speeds. For example, depending on the number of pills being dispensed and the size and shape of the pills, the motion of the oscillating member 310 may be programmed to ensure that the pills are dispensed as desired. In this manner, the oscillating member 310 may move back-and-forth and up-and-down at constant or varying speeds, times, intervals, and/or angles of rotation.

FIGS. 38-42 depict a container 400 for a portable pill dispenser. The container 400 may be incorporated into any of the embodiments described herein. For example, the container may be attached to a housing and used in conjunction with any of the dispensing mechanisms disclosed herein. In some instances, the container and the housing may be similar to those described in FIGS. 1-13.

The container includes a delivery system for delivering pills (in a controlled manner) to the dispensing mechanism. The container may include a slide (or delivery ramp) formed as part of the container. That is, the container and the slide may be integrally formed. The container is configured to automatically align pills, which then slide down the slide towards the dispensing mechanism. One or more gates, e.g., rotating disks, may control the advancement of pills down the slide to the dispensing mechanism. Any metering device may be used in conjunction with the slide to control the movement of pills along the slide.

Figure 38:
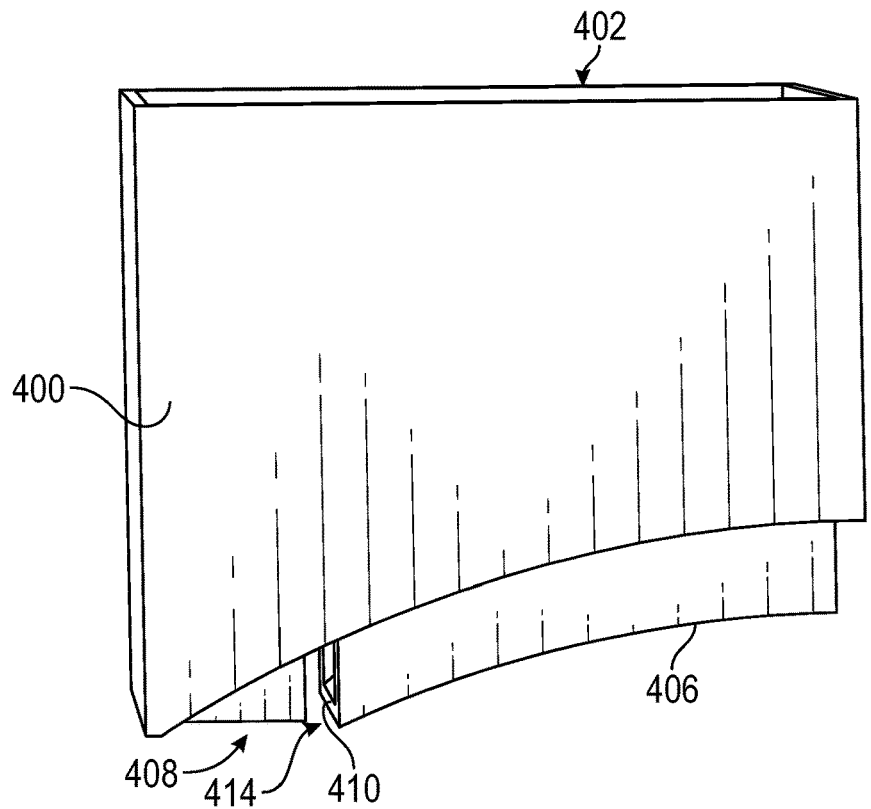
FIG. 38 depicts a container of a portable pill dispenser in accordance with one or more embodiments of the disclosure.

As depicted in FIG. 38, the container 400 includes an opening 402. In some instances, the opening 402 is disposed about the top of the container 400. A user may use the opening 402 to insert (i.e., fill) one or more pills into the container 400. A lid (not shown) may be attached to the container 400 to close the opening 402. The lid may be detachably attached or permanently attached to the container 400. In some instances, a special tool may be needed to remove the lid.

Figure 42:
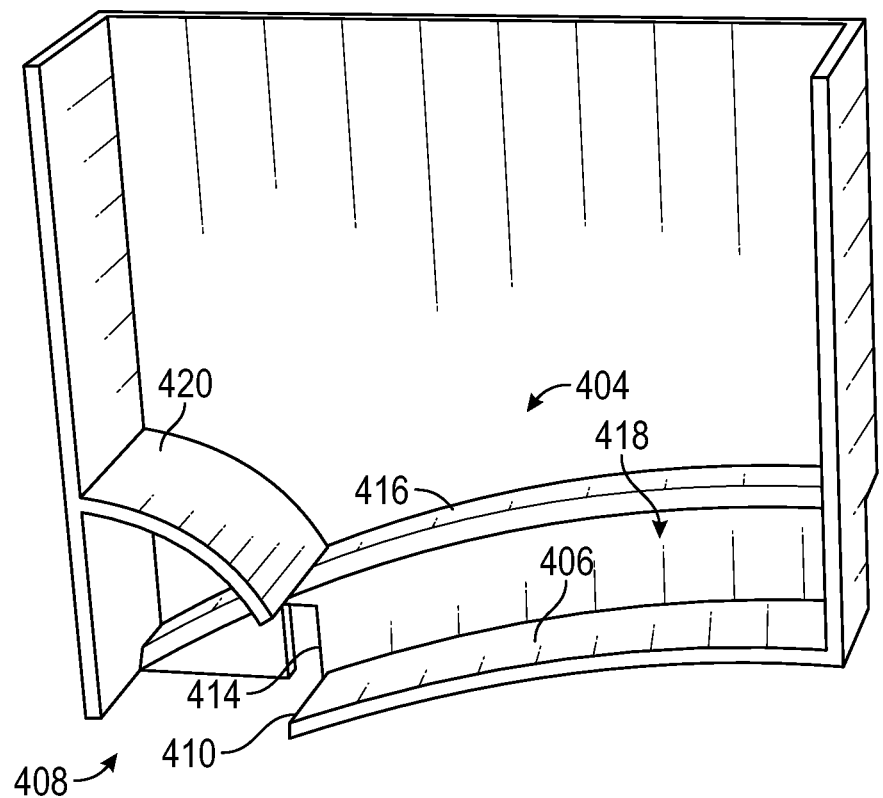
FIG. 42 depicts a container comprising a pill delivery system of a portable pill dispenser in accordance with one or more embodiments of the disclosure.

Referring to FIG. 42, the container 400 includes a pill delivery system 404. In certain embodiments, the pill delivery system 404 includes a slide 406. The slide 406 may be integrally formed within the container 400. For example, the slide 406 may form a bottom surface of the container 400. An exit opening 408 is disposed at an end 410 of the slide 406. The slide 406 may be any suitable size, shape, or configuration. In some instances, the slide 406 comprises an arched ramp descending to the exit opening 408. In other instances, the slide 406 is a slanted surface (or uniform ramp) which descends to the exit opening 408. The slide 406 may be any suitable size, shape, or configuration.

Figure 39:
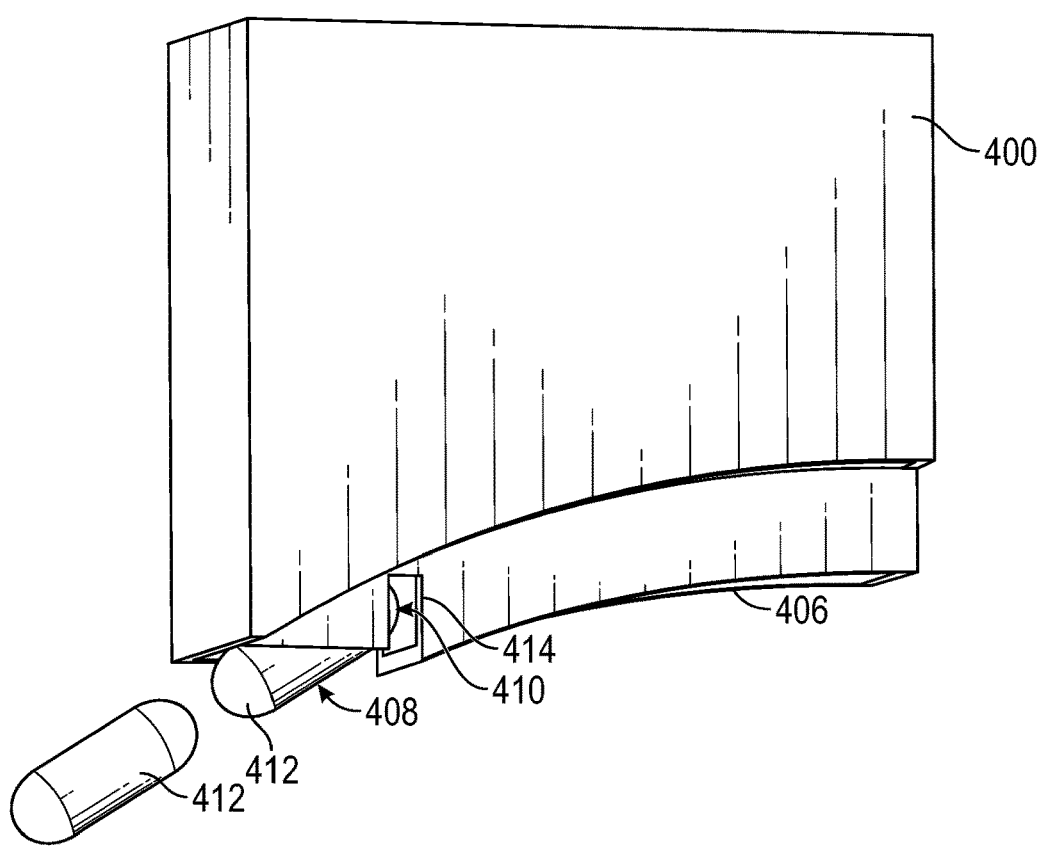
FIG. 39 depicts a container of a portable pill dispenser in accordance with one or more embodiments of the disclosure.

As depicted in FIG. 39, the exit opening 408 may be sized and shaped to enable at least one pill 412 to exit the container 400 at a time. In this manner, the pills 412 may slide down the slide 406 and exit the container 400 via the exit opening 408. The pills 412 may be directed from the exit opening 408 to a dispensing mechanism, such as the rotating barrel discussed herein. The pills 412 may exit the container 400 via the exit opening 408 to any of the dispensing mechanism discussed herein.

Referring back to FIG. 42, the container 400 may include a gate (discussed in greater detail below) disposed at the end 410 of the slide 406 in front of the exit opening 408. That is, the gate is disposed between the end 410 of the slide 406 and the exit opening 408. The gate is configured to meter the movement of the pills 412 from the slide 406 to the exit opening 408. In one example, the gate comprises two semicircular rotating disks spaced apart which meter the movement of the pills 412 from the slide 406 to the exit opening 408. For example, the semicircular rotating disk may rotate from a closed position, which may block (or prevent) the pills 412 from sliding from the slide 406 to the exit opening 408, to an open position, which may enable at least one pill 412 to move from the slide 406 to the exit opening 408. Other types of gates may be used herein, including oscillating doors or pins disposed between the slide 406 and the exit opening 408. Any suitable metering device may be used. In addition, in certain embodiments, the back side of the rotating barrel opposite the cavity of the dispending mechanism disclosed herein may prevent the pills from sliding down the slide to the exit opening.

To accommodate the gate, the container 400 may include at least one gate recess 414. In some instances, the gate recess 414 is a slot in the side of the container 400. The gate recess 414 may be located at the end 410 of the slide 406 between the slide 406 and the exit opening 408. In instances where the gate is one or more semicircular rotating disks, the semicircular rotating disks may at least partially sit within one or more gate recesses 414. In this manner, the gate may move in and out of the gate recess to open and block passage of the pills from the slide 406 to the exit opening 408.

Figure 40:
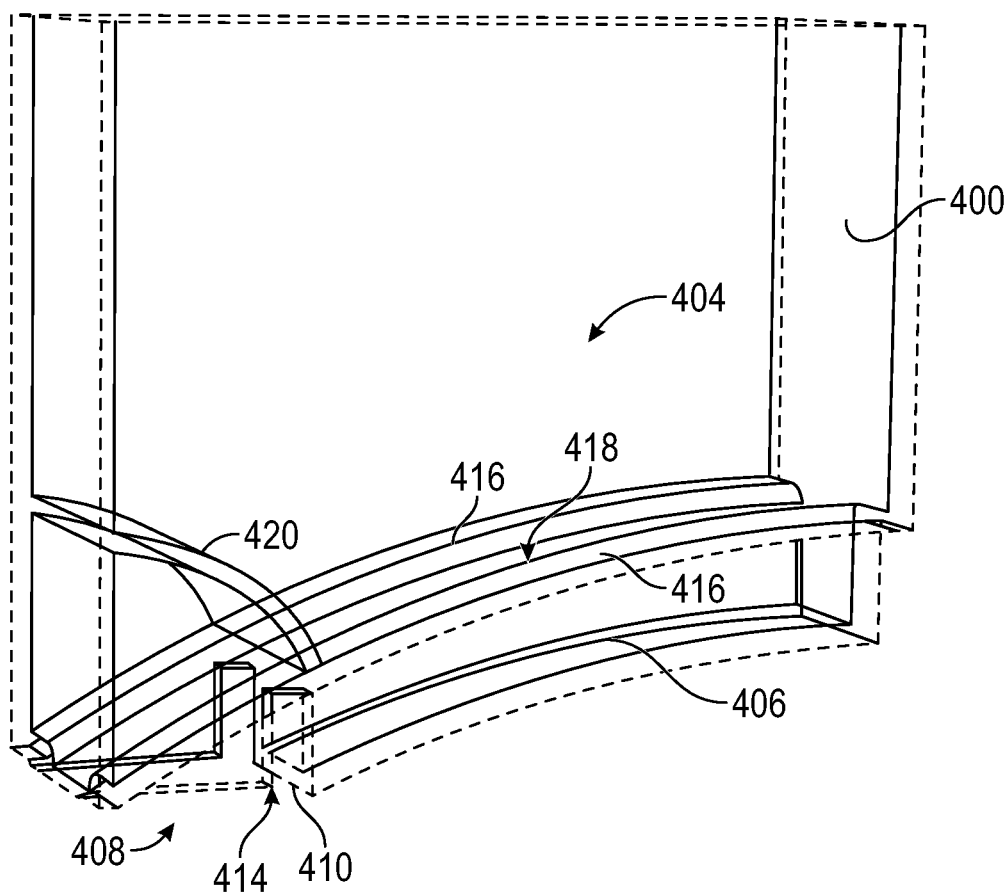
FIG. 40 depicts a container comprising a pill delivery system of a portable pill dispenser in accordance with one or more embodiments of the disclosure.
Figure 41:
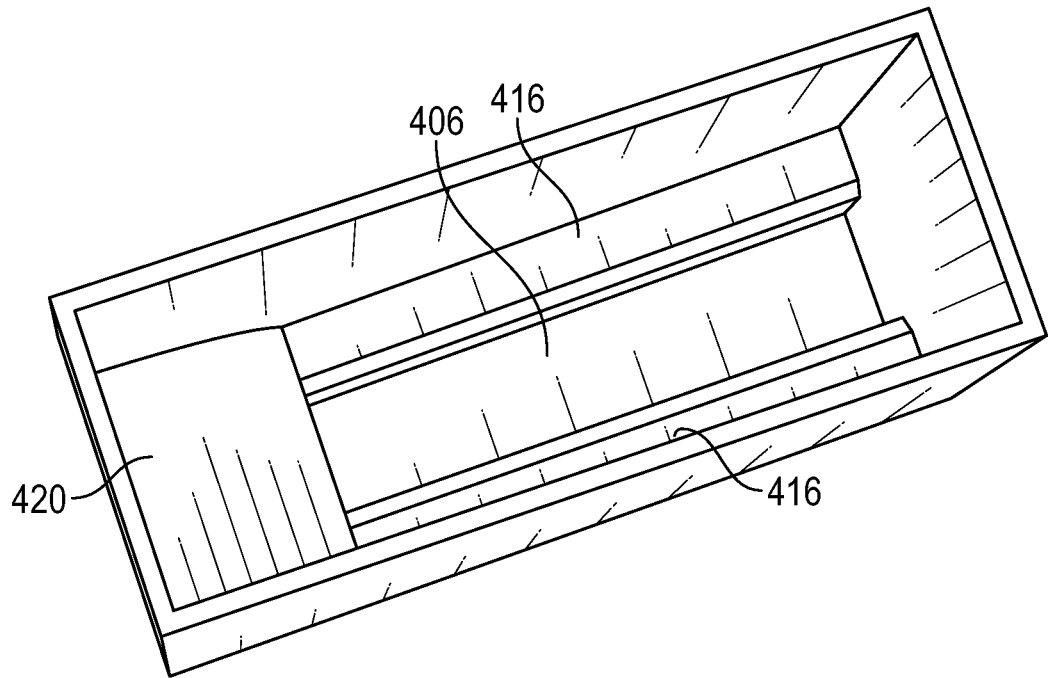
FIG. 41 depicts a container comprising a pill delivery system of a portable pill dispenser in accordance with one or more embodiments of the disclosure.

In order to align the pills 412 along the slide 406, the container 400 includes at least one ledge 416 extending from an internal wall. In some instances, as depicted in FIGS. 40 and 41, each internal side wall of the container 400 may include a ledge 416 extending therefrom and disposed above the slide 406. The ledges 416 may form a channel 418 about (above) the slide 406 surface. The channel 418 may be sized and shaped to align the pills 412 in single file along the slide 406. In this manner, a user may simply shake the container 400, which may cause the pills 412 to align within the channel 418 along the slide 406. The height of the channel 418 from the surface of the slide 406 to the ledge 416 may correspond to the thickness of the pills 412.

The container 400 further comprises a jam prevention wall 420 disposed above the exit opening 408. In some instances, the jam prevention wall 420 is an arched wall or a slanted surface (or uniform ramp). The jam prevention wall 420 extends from an internal side wall within the container 400 over top of the exit opening 408 to the ledges 416 above the gate. In this manner, the jam prevention wall 420 prevents pills 412 from jamming (or becoming stuck at the exit opening). The jam prevention wall 420 also directs pills 412 into the channel 418.

Figure 43:
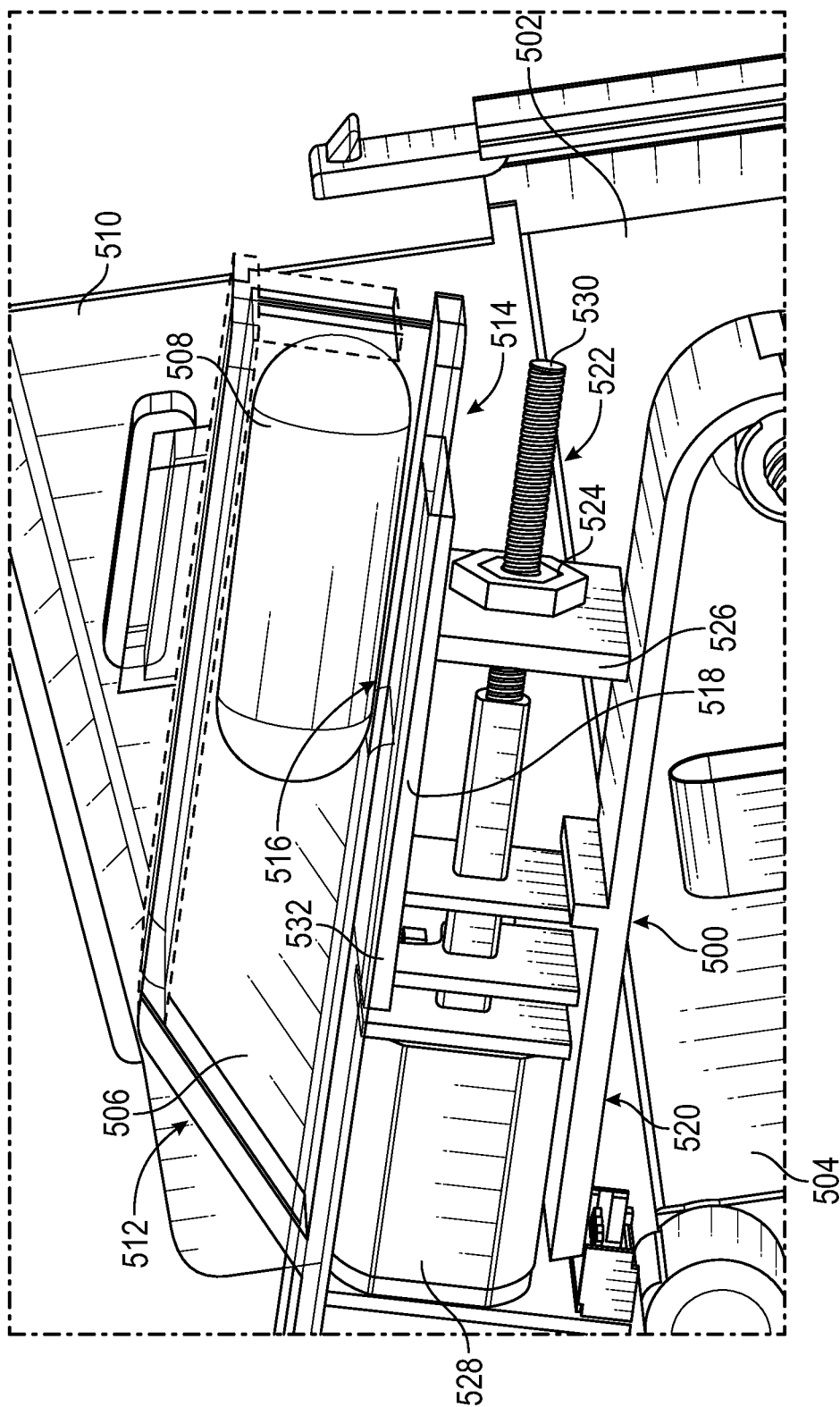
FIG. 43 depicts a trap door assembly of a portable pill dispenser in accordance with one or more embodiments of the disclosure.

FIG. 43 depicts a dispensing mechanism 500 for a portable pill dispenser. The dispensing mechanism 500 may be incorporated into any of the embodiments described herein. In particular, the dispensing mechanism 500 may replace or work in conjunction with the dispensing mechanism 134 in FIGS. 1-13. In some instances, the container and the housing 504 may be similar to those described in FIGS. 1-13. The dispensing mechanism 500 may be incorporated into any pill dispenser.

A ramp 506 is configured to guide the pills 508 from a container to the dispensing mechanism 500. The dispensing mechanism 500 may dispense the pills 508 to a dispensing chute 502 and a dispensing opening in the housing 504. In some instances, the ramp 506 guides one pill at a time to the dispensing mechanism 500. That is, the ramp 506 is sized and shaped to align one pill into the dispensing mechanism 500 at a time. In other instances, the ramp 506 may enable two or more pills 508 into the dispensing mechanism 500 at once. The ramp 506 may be attached to the support wall 510, which may be attached to or integrally formed with the housing 504. In other instances, the ramp 506 may be directly attached to the housing 504. The ramp 506 includes an inlet 512 facing the container and an outlet 514 at an opposite end thereof. The size and shape of the inlet 512 and the outlet 514 may vary depending on the pills being dispensed. The ramp 506 may include one or more angled portions so as to use gravity to cause the pills to slide into the dispensing mechanism 500. For example, the ramp 506 may function as a funnel directing one or more pills to the dispensing mechanism 500. The ramp 506 may be any suitable size, shape, or configuration.

The dispensing mechanism 500 is configured to dispense the pills 508 from the container. In some instance, the dispensing mechanism 500 comprises a trap door assembly 516 configured to dispense the at least one pill 508 from the container to the dispensing opening. The trap door assembly 516 comprises a sliding door 518 disposed about the outlet 514 of the ramp 506. The sliding door 518 may be configured to slide along a linear path. For example, the sliding door 518 may slide from an open position to a closed position and vice versa. In the closed position, the sliding door 518 may block the outlet 514 of the ramp 506. In this manner, pills 508 may be unable to pass from the ramp 506 to the dispensing opening. In the open position, the sliding door 518 may not block the opening of the outlet 514 of the ramp 506, which may allow the pills 508 to pass from the ramp 506 to the dispensing opening.

The sliding door 518 may be actuated via a linear actuator 520. In this manner, the sliding door 518 is in mechanical communication with the linear actuator 520, which is configured to move the sliding door 518 between the open position and the closed position. In one example embodiment, the linear actuator 520 is a traveling nut linear actuator. For example, the sliding door 518 may include a threaded member 522 attached thereto. In one example, the threaded member 522 comprises a threaded nut 524 attached to (or formed within) a protrusion 526 extending from the sliding door 518. In such instances, the linear actuator 520 comprises a motor 528 attached to a lead screw 530 extending therefrom. The lead screw 530 is movable attached to the threaded member 522. Thus, in operation, the motor 528 turns the lead screw 530, which in turn moves the threaded member 522, which in turn moves the sliding door 518 between the open and closed position.

In certain embodiments, in order to prevent more than one pill 508 from passing through the outlet 514 of the ramp 506 when the sliding door 518 is moved to the open position, the side 532 of the sliding door 518 furthest away from the outlet 514 of the ramp 506 may raise upward into the ramp 506 as the sliding door 518 is moved from the closed position to the open position. The raising of the sliding door 518 may block the ramp 506 and prevent the moment of pills 508 along the ramp 506. Conversely, as the sliding door 518 is moved from the open position to the closed position, the side 532 of the sliding door 518 furthest away from the outlet 514 of the ramp 506 may lower to unblock and ramp 506 and enable the pills 508 to slide back down the ramp 506 to stage the next pill 508 in line for dispensing.

Figure 44:
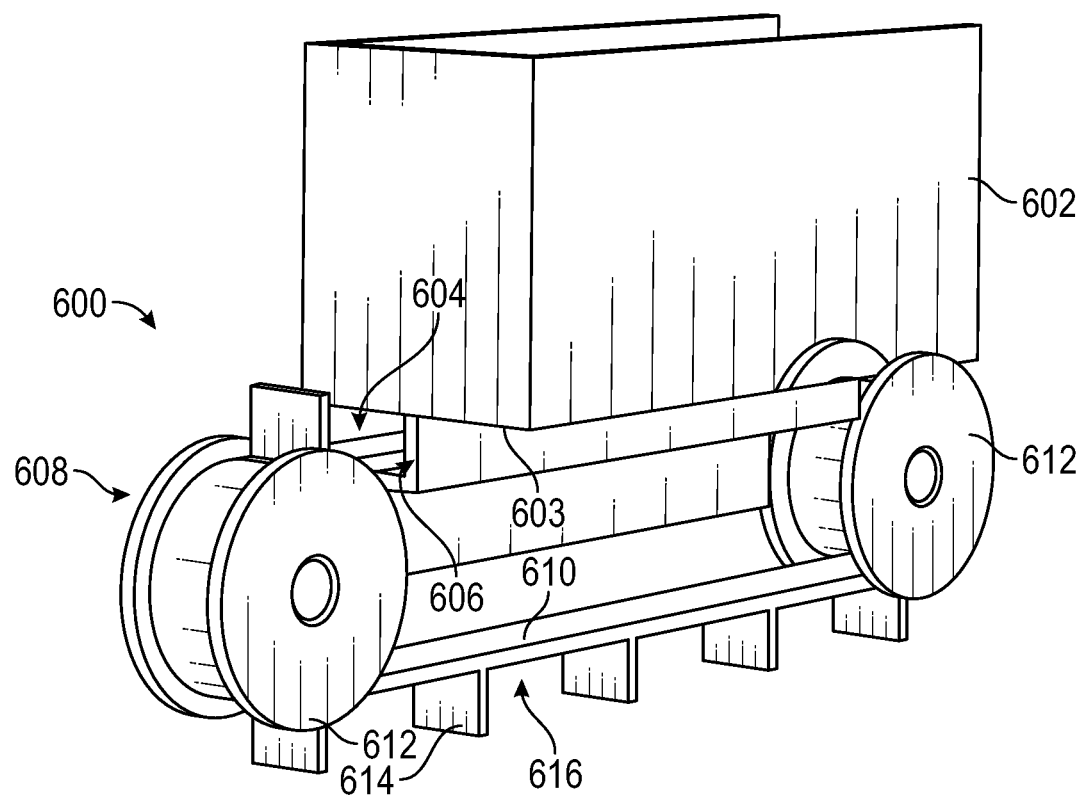
FIG. 44 depicts a dispensing mechanism comprising a belt-and-pulley dispensing system of a portable pill dispenser in accordance with one or more embodiments of the disclosure.
Figure 45:
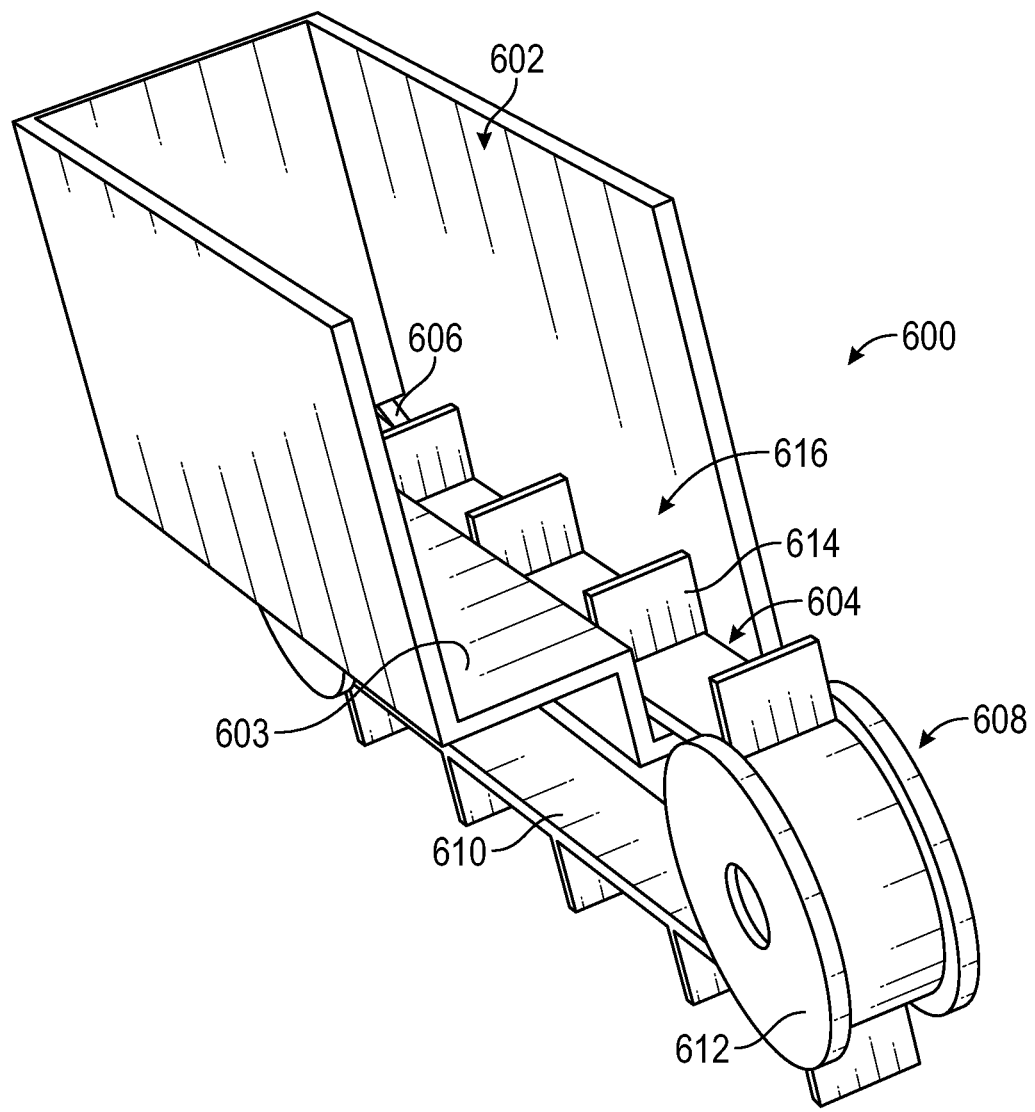
FIG. 45 depicts a dispensing mechanism comprising a belt-and-pulley dispensing system of a portable pill dispenser in accordance with one or more embodiments of the disclosure.
Figure 46:
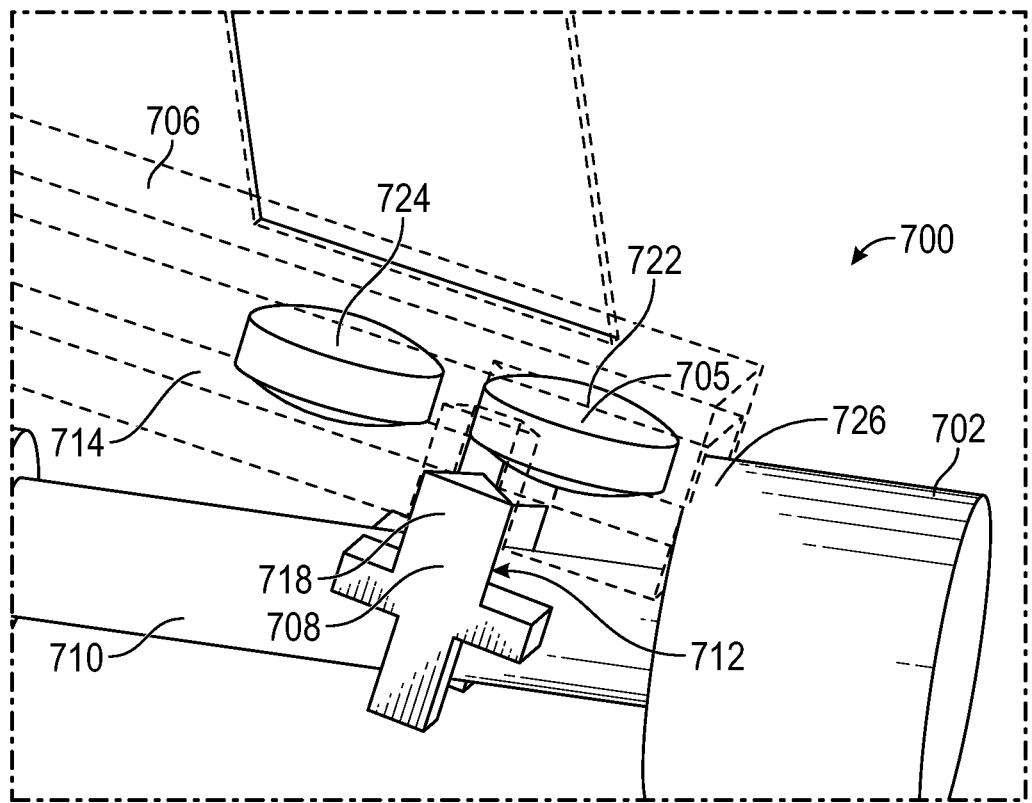
FIG. 46 depicts a dispensing mechanism comprising one or more movable stoppers of a portable pill dispenser in accordance with one or more embodiments of the disclosure.
Figure 47:
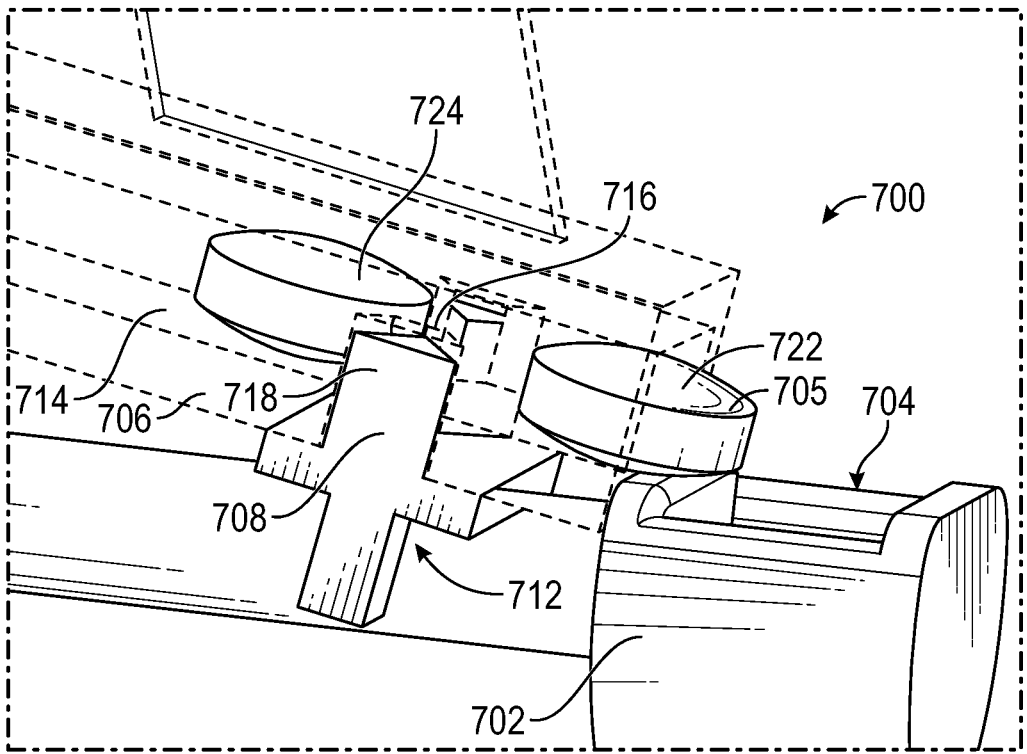
FIG. 47 depicts a dispensing mechanism comprising one or more movable stoppers of a portable pill dispenser in accordance with one or more embodiments of the disclosure.
Figure 48:
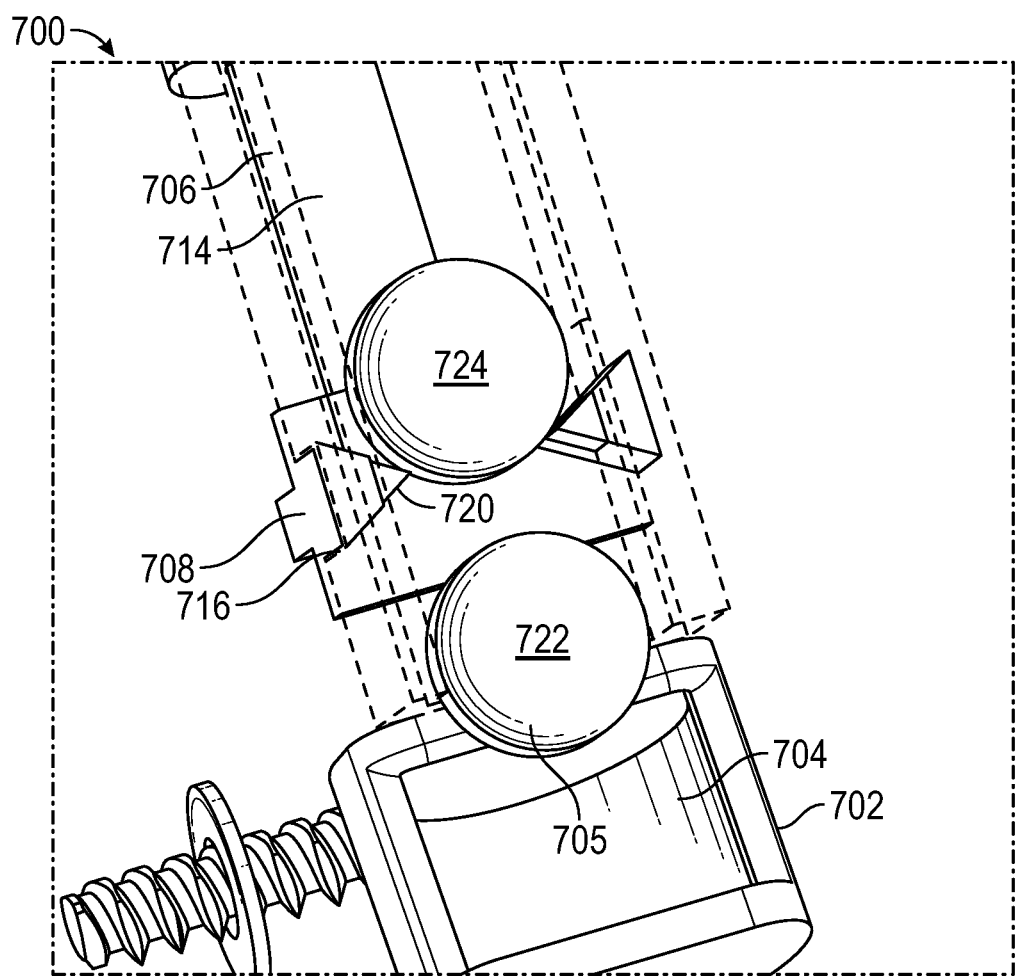
FIG. 48 depicts a dispensing mechanism comprising one or more movable stoppers of a portable pill dispenser in accordance with one or more embodiments of the disclosure.
Figure 49:
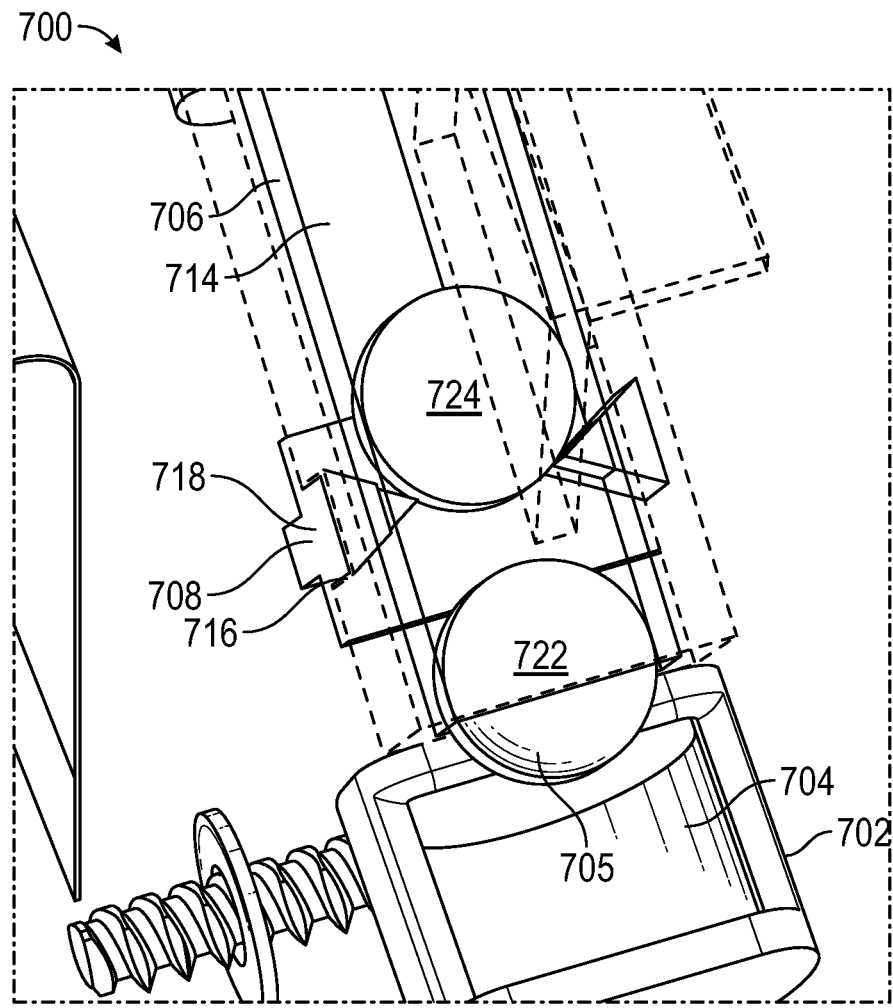
FIG. 49 depicts a dispensing mechanism comprising one or more movable stoppers of a portable pill dispenser in accordance with one or more embodiments of the disclosure.
Figure 50:
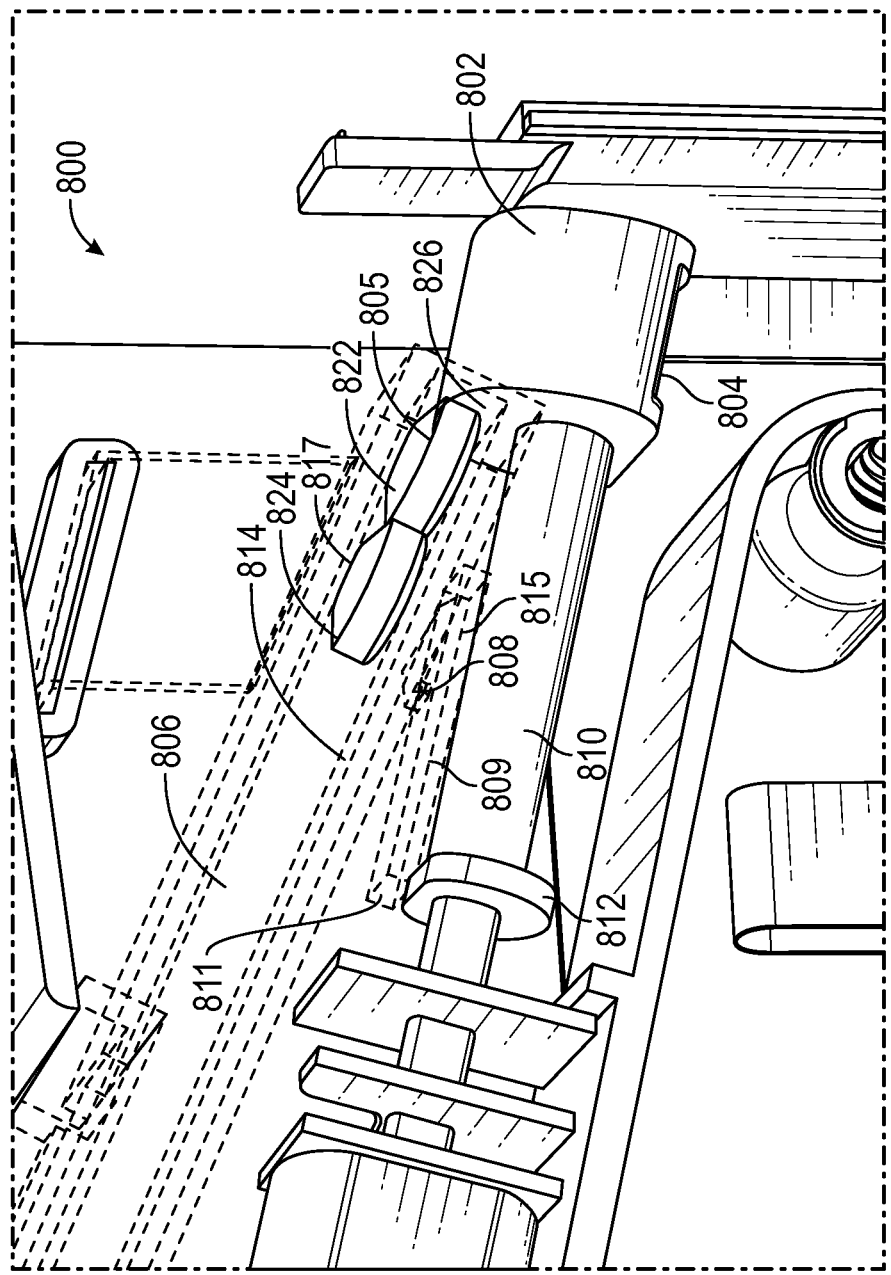
FIG. 50 depicts a dispensing mechanism comprising a movable floor of a portable pill dispenser in accordance with one or more embodiments of the disclosure.
Figure 51:
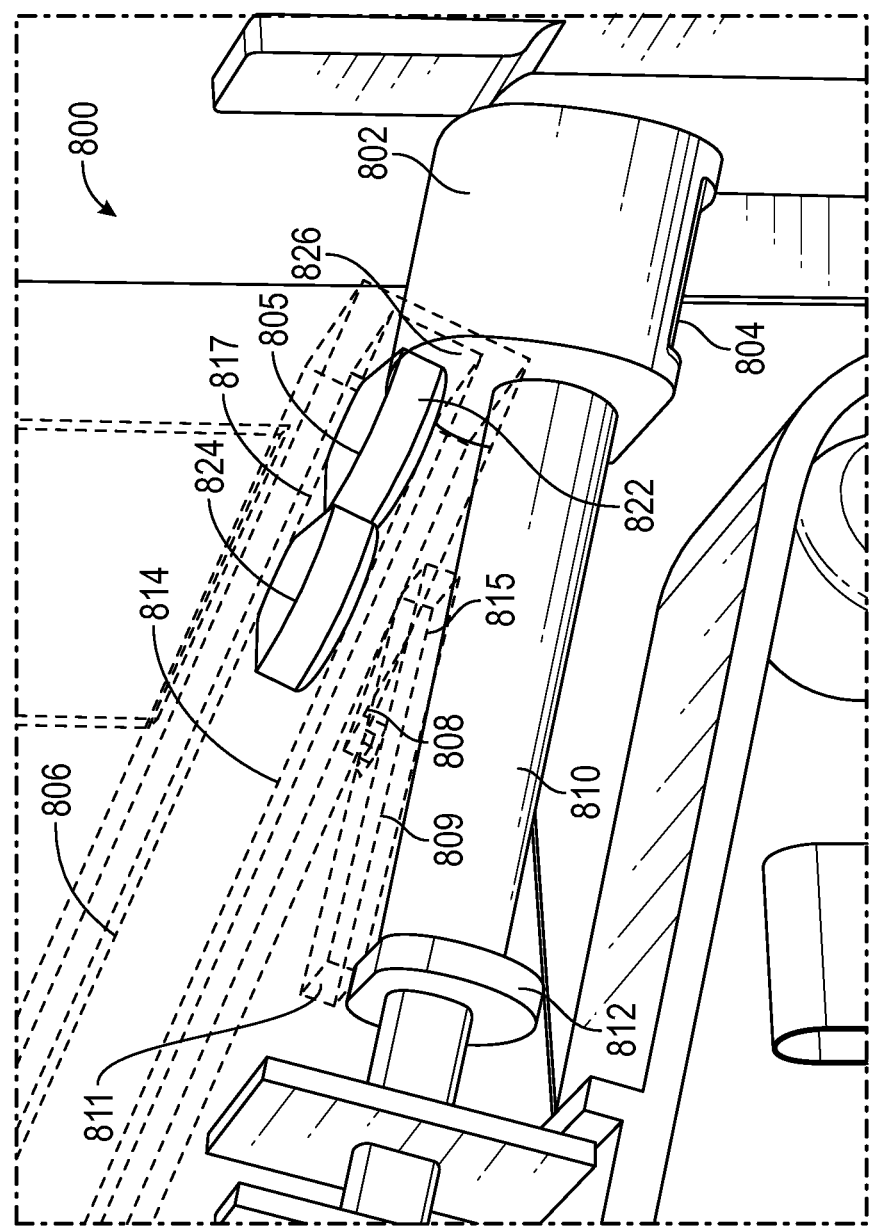
FIG. 51 depicts a dispensing mechanism comprising a movable floor of a portable pill dispenser in accordance with one or more embodiments of the disclosure.
Figure 52:
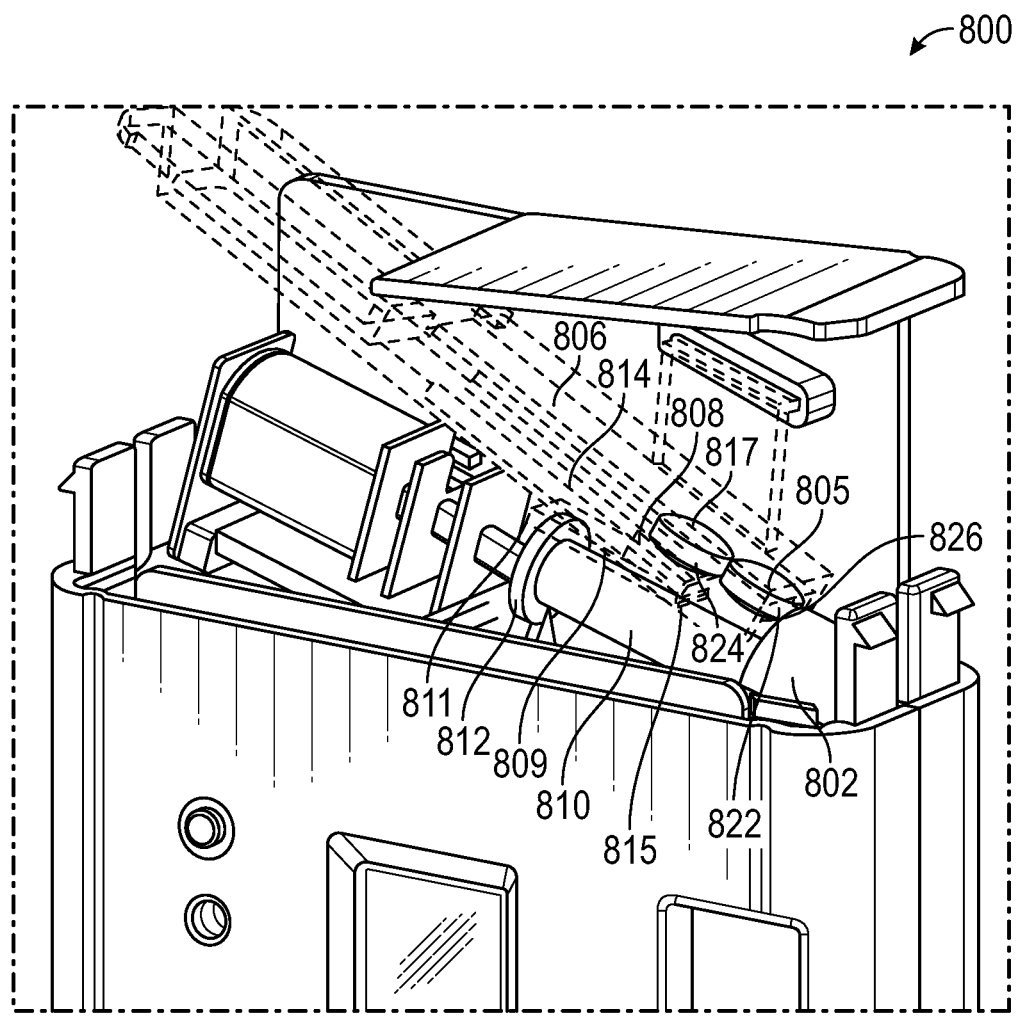
FIG. 52 depicts a dispensing mechanism comprising a movable floor of a portable pill dispenser in accordance with one or more embodiments of the disclosure.
Figure 53:
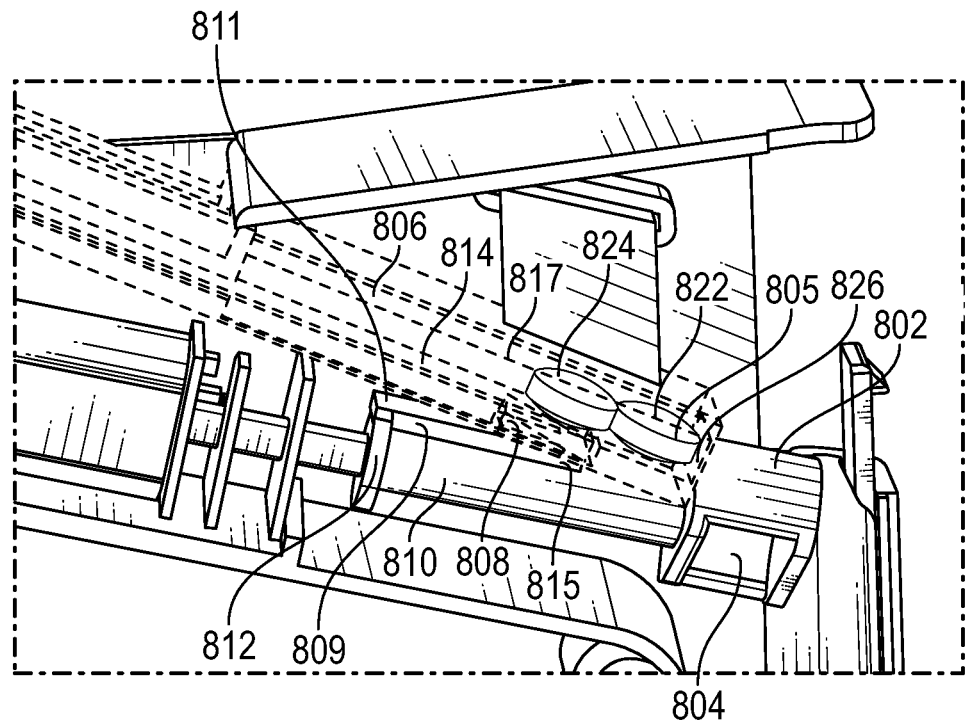
FIG. 53 depicts a dispensing mechanism comprising a movable floor of a portable pill dispenser in accordance with one or more embodiments of the disclosure.
Figure 54:
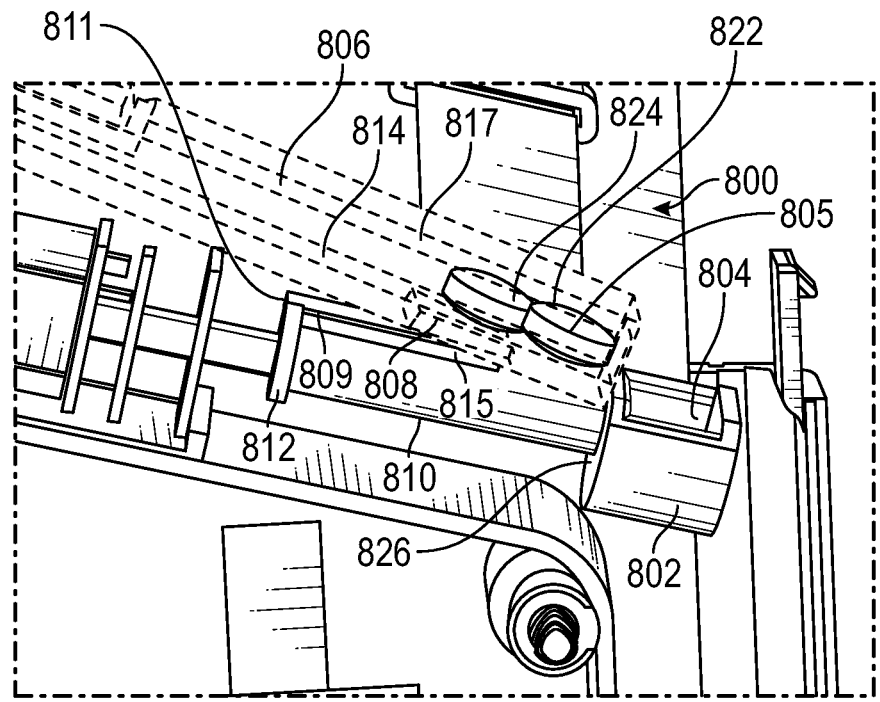
FIG. 54 depicts a dispensing mechanism comprising a movable floor of a portable pill dispenser in accordance with one or more embodiments of the disclosure.
Figure 55:
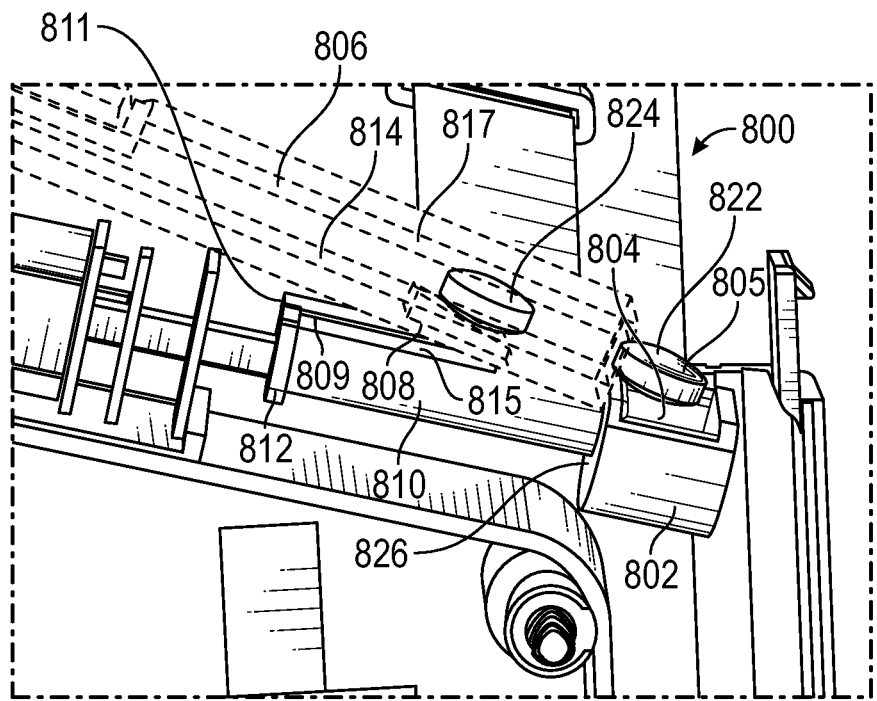
FIG. 55 depicts a dispensing mechanism comprising a movable floor of a portable pill dispenser in accordance with one or more embodiments of the disclosure.
Figure 56:
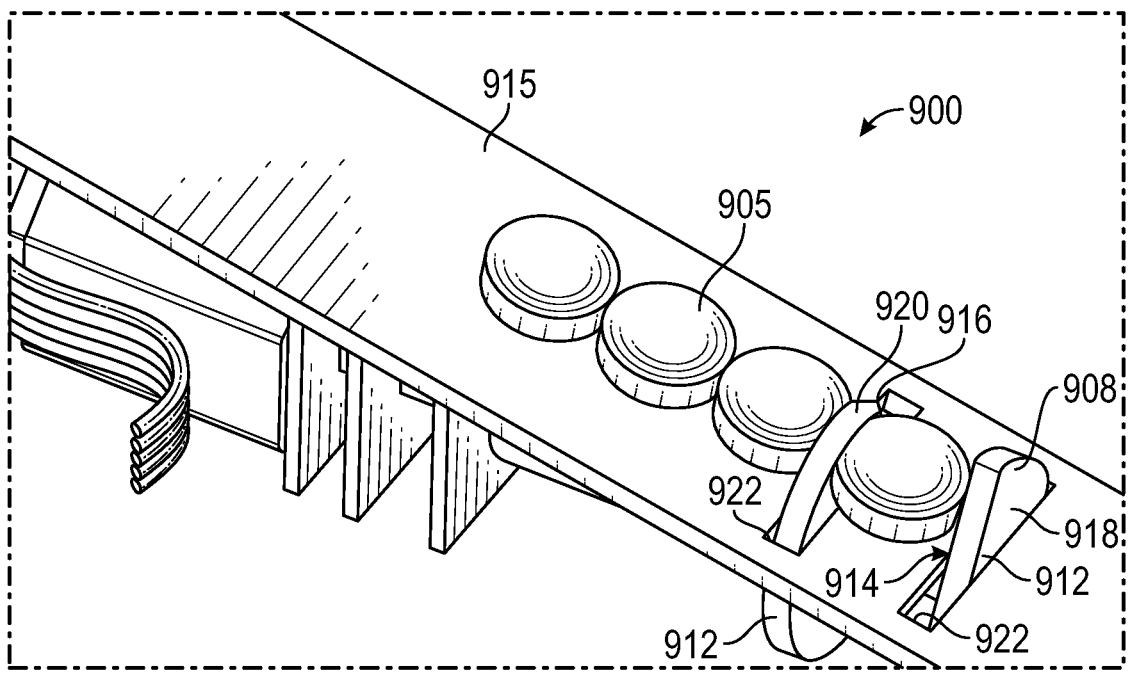
FIG. 56 depicts a dispensing mechanism comprising one or more rotating gates of a portable pill dispenser in accordance with one or more embodiments of the disclosure.
Figure 57:
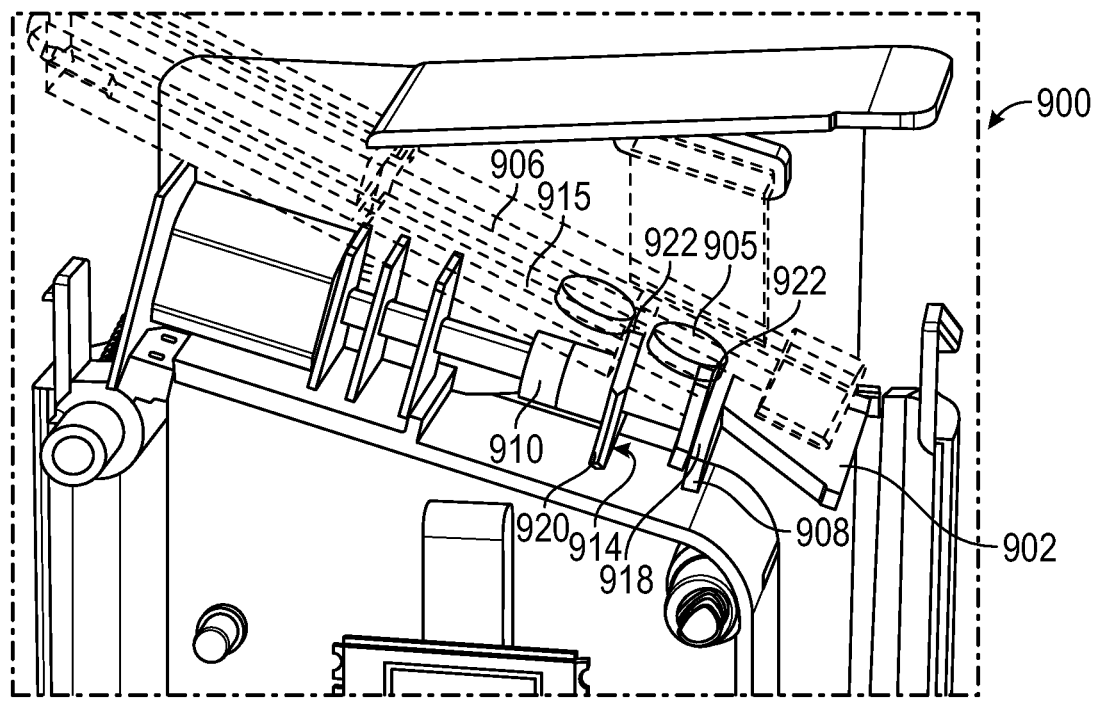
FIG. 57 depicts a dispensing mechanism comprising one or more rotating gates of a portable pill dispenser in accordance with one or more embodiments of the disclosure.
Figure 58:
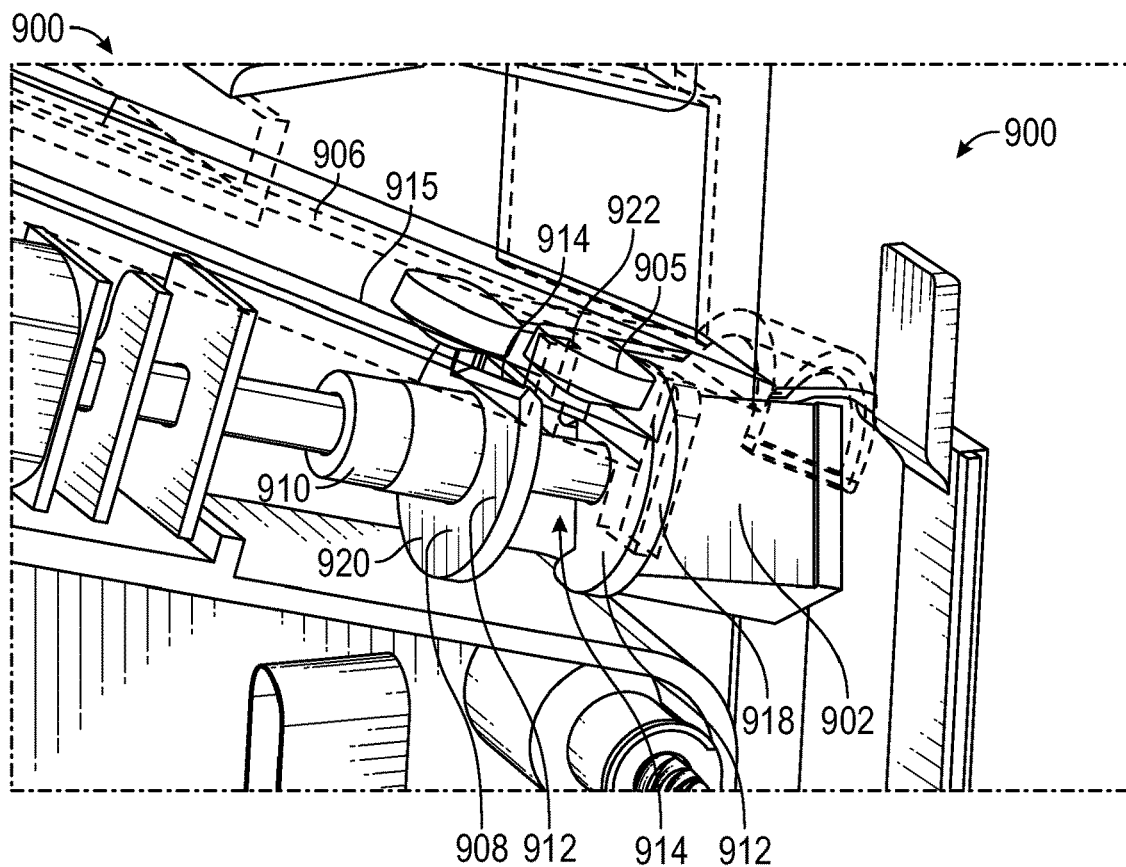
FIG. 58 depicts a dispensing mechanism comprising one or more rotating gates of a portable pill dispenser in accordance with one or more embodiments of the disclosure.
Figure 59:
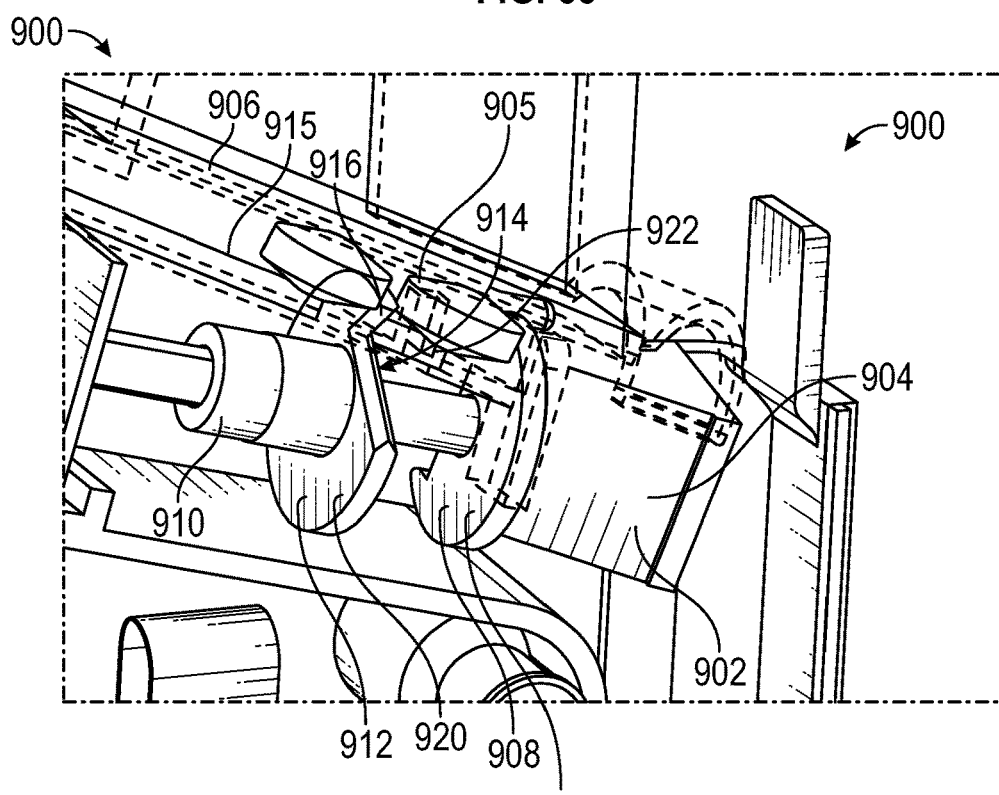
FIG. 59 depicts a dispensing mechanism comprising one or more rotating gates of a portable pill dispenser in accordance with one or more embodiments of the disclosure.
Figure 60:
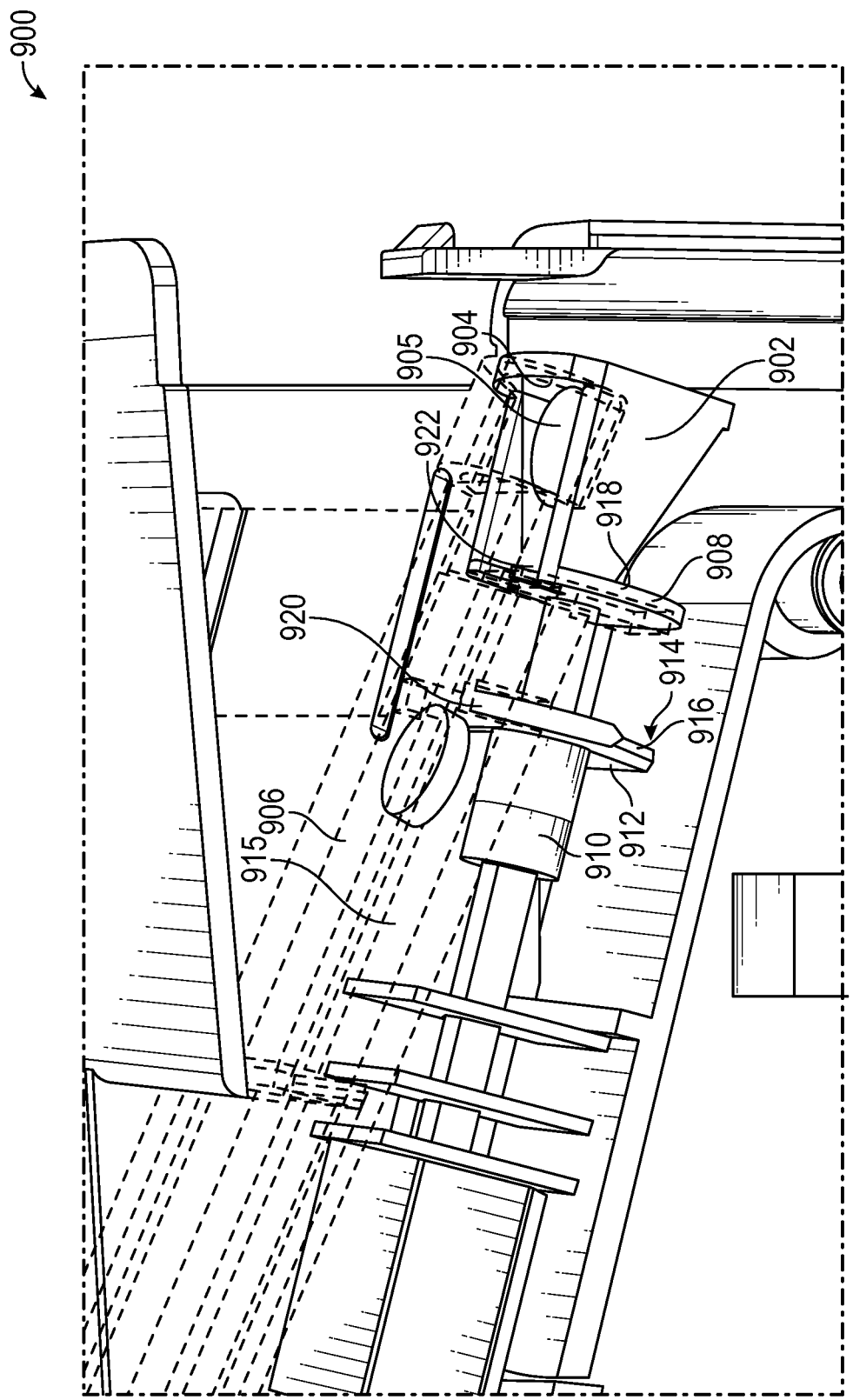
FIG. 60 depicts a dispensing mechanism comprising one or more rotating gates of a portable pill dispenser in accordance with one or more embodiments of the disclosure.
Figure 61:
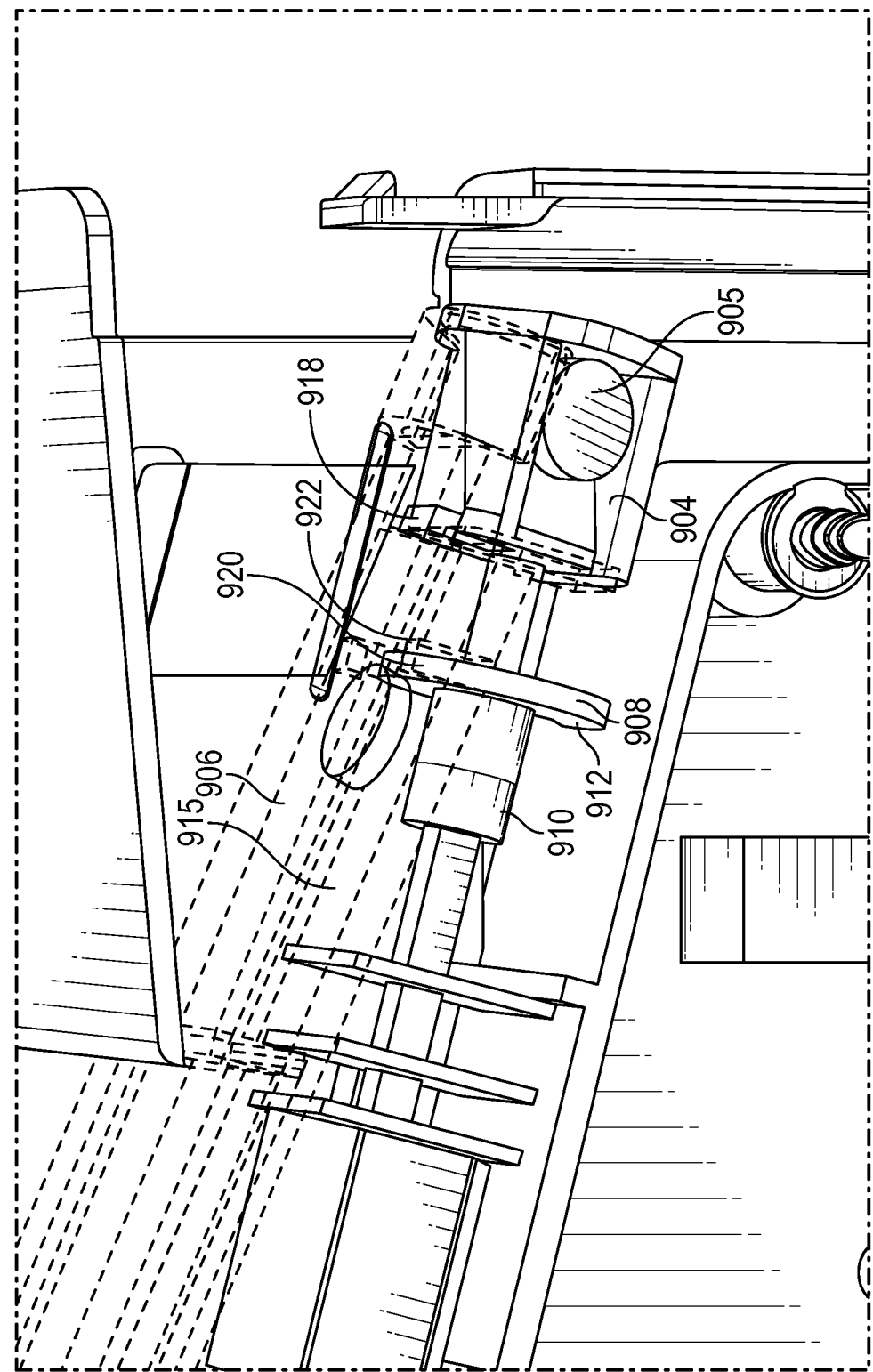
FIG. 61 depicts a dispensing mechanism comprising one or more rotating gates of a portable pill dispenser in accordance with one or more embodiments of the disclosure.

FIGS. 44 and 45 depict a dispensing mechanism 600. The dispensing mechanism 600 may be incorporated into any of the embodiments described herein. The dispensing mechanism 600 includes a container 602, in which a number of pills are disposed. A channel 604 is located at a bottom of the container 602. For example, the container 602 may include a ledge 603 that at least partially forms the channel 604. In some instances, the ledge 603 is configured to direct pills to the channel 604. The channel 604 includes an outlet 606. The outlet 606 may be sized and shaped for one pill at a time to pass therethrough.

The dispensing mechanism 600 includes a belt-and-pulley dispensing system 608. In some embodiments, the belt-and-pulley dispensing system 608 comprises a continuous track. For example, the belt-and-pulley dispensing system 608 includes a belt 610 disposed about two wheels 612. At least one of the wheels 612 is attached to an actuator, such as a motor, to rotate the wheel 612. As the wheels 612 rotate, the belt 610 also rotates.

At least a portion of the belt 610 is disposed within the channel 604 of the container 602. In this manner, the belt 610 is configured to move linearly along the channel 604 and out of the outlet 606 in the container 602. The belt 610 includes a plurality of spaced apart protrusions 614 extending therefrom. The protrusions 614 may be sized and shaped to pass through the outlet 606. In some instances, the size of the protrusions 614 corresponds to the size of the outlet 606 such that the protrusions 614 can block the outlet 606. The protrusions 614 form a number of slots 616. That is, a slot 616 is formed between two protrusions 614. The slots 616 may be sized and shaped to receive a pill therein. In this manner, as the belt 610 rotates, a single pill may fill each of the slots 616 and pass through the outlet 606 of the container 602 one at a time. The pills may then be directed to a dispensing opening in the pill dispenser.

FIGS. 46-49 depict a dispensing mechanism 700 for a portable pill dispenser. The dispensing mechanism 700 may be incorporated into any of the embodiments described herein. In particular, the dispensing mechanism 700 may replace or work in conjunction with the dispensing mechanism 134 in FIGS. 1-13. The dispensing mechanism 700 may be incorporated into any pill dispenser.

The dispensing mechanism 700 comprises a rotating barrel 702. The rotating barrel 702 includes at least one cavity 704 therein. The cavity 704 is configured to receive at least one pill 705 therein. Rotation of the rotating barrel 702 dispenses the pill 705 from the cavity 704 to a dispensing opening in the pill dispenser. The operation of the rotating barrel 702 is similar to the one described in the dispensing mechanism 134 described in FIGS. 1-13.

The dispensing mechanism 700 also includes a ramp 706. The ramp 706 is configured to align and direct the pills 705 to the rotating barrel 702. The ramp 706 may form a channel or passage to the rotating barrel 702. The cross-section of the channel or passage may be circular or square, for example. The ramp 706 may be any suitable size, shape, or configuration. In order to regulate the number of pills 705 passing to the rotating barrel 702, one or more movable stoppers 708 are disposed about the ramp 706 to control the movement of the pill 705 to the rotating barrel 702. In some instances, the movable stoppers 708 are disposed at or near an end of the ramp 706. The movable stoppers 708 may be located at any location along the ramp 706.

In some instances, the movable stoppers 708 are configured to move up and down within the ramp 706 between an open position and a closed position in order to block the pills 705 from sliding into the rotating barrel 702. For example, the rotating barrel 702 comprises a neck portion 710 having a cam surface 712. The cam surface 712 is in mechanical communication with the movable stoppers 708. That is, a surface of the movable stoppers 708 may be in contact with the cam surface 712 of the neck portion 710 of the rotating barrel 702. The interface between the movable stoppers 708 and the cam surface 712 on the neck portion 710 of the rotating barrel 702 is configured to move the movable stoppers 708 between the open position and the closed position as the neck portion 710 rotates.

In the open position, the movable stoppers 708 may be flush with a floor 714 of the ramp 706 to enable the pills 705 to slide down the ramp 706 and into the rotating barrel 702. Conversely, in the closed position, the movable stoppers 708 may be disposed at least partially within the ramp 706 to block and prevent the movement of the pills 705 along the ramp 706 and into the rotating barrel 702.

To enable the movable stoppers 708 to move in and out of the ramp 706 between the open position and the closed position, the ramp 706 includes one or more corresponding apertures 716 therethrough in which the movable stoppers 708 can pass in and out. In this manner, the movable stoppers 708 may oscillate in and out of the apertures 716 between the open position and the closed position.

In certain embodiments, the movable stoppers 708 comprise two spaced apart pins 718 that move up and down along the cam surface 712 as the neck portion 710 rotates. The two pins 718 may be disposed on opposite sides of the ramp 706. In such instances, the corresponding apertures 716 are also disposed on opposite sides of the ramp 706. In some instances, the two pins 718 are triangular shaped. In such instances, the points (or tips) 720 of the triangular pins may face each other.

The movable stoppers 708 may be configured to enable one pill 705 to pass to the rotating barrel 702 at a time. For example, a first pill 722 may be provided to or disposed within the cavity 704 and a second pill 724 may be blocked within the ramp 706 by the movable stoppers 708 in the closed position. When the rotating barrel 702 rotates, the first pill 722 is dispensed to the dispensing opening and the movable stoppers 708 are moved from the closed position to the open position via the cam surface 712, causing the second pill 724 to slid down the ramp 706 towards the rotating barrel 702. In some instances, a backside 726 of the rotating barrel 702 prevents the second pill 724 from exiting the ramp 706 until the rotating barrel 702 makes a full rotation such that the second pill 724 can exit the ramp 706 into the cavity 704. When the rotating barrel 702 fully rotates such that the second pill 724 can exit the ramp 706 into the cavity 704, the movable stoppers 708 are moved back into the closed position to prevent other pills from being provided to or entering the cavity 704.

The dispensing mechanism 700 is particularly useful for smaller circular tablets. In particular, the movable stoppers 708 prevent blockage and jams between the ramp 706 and the rotating barrel 702. The dispensing mechanism 700 may be used with any sized or shaped pill.

FIGS. 50-55 depict a dispensing mechanism 800 for a portable pill dispenser. The dispensing mechanism 800 may be incorporated into any of the embodiments described herein. In particular, the dispensing mechanism 800 may replace or work in conjunction with the dispensing mechanism 134 in FIGS. 1-13. The dispensing mechanism 800 may be incorporated into any pill dispenser.

The dispensing mechanism 800 comprises a rotating barrel 802. The rotating barrel 802 includes at least one cavity 804 therein. The cavity 804 is configured to receive at least one pill 805 therein. Rotation of the rotating barrel 802 dispenses the pill 805 from the cavity 804 to a dispensing opening in the pill dispenser. The operation of the rotating barrel 802 is similar to the one described in the dispensing mechanism 134 described in FIGS. 1-13.

The dispensing mechanism 800 also includes a ramp 806. The ramp 806 is configured to align and direct the pills 805 to the rotating barrel 802. The ramp 806 may form a channel or passage to the rotating barrel 802. The channel or passage may be circular or square. The ramp 806 may be any suitable size, shape, or configuration. In order to regulate the number of pills 805 passing to the rotating barrel 802, a movable floor 808 is disposed within the ramp 806 to control the movement of the pills 805 to the rotating barrel 802. In some instances, the movable floor 808 is disposed at or near an end of the ramp 806. The movable floor 808 may be located at any location within or along the ramp 806.

In some instances, the movable floor 808 is configured to move up and down within the ramp 806 between an open position and a closed position in order to block (or pinch) the pills 805 from sliding into the rotating barrel 802. For example, the rotating barrel 802 comprises a neck portion 810 having a cam surface 812. The cam surface 812 is in mechanical communication with the movable floor 808. In some embodiments, a tongue 809 acts as an intermediate between the cam surface 812 of the neck portion 810 and the movable floor 808. That is, a first end 811 of the tongue 809 contacts the cam surface 812 of the neck portion 810 of the rotating barrel 802, and a second end 815 of the tongue 809 contacts the movable floor 808. As a result, as the cam surface 812 on the neck portion 810 of the rotating barrel 802 rotates, the first end 811 moves up and down, which may cause the second end 815 of the tongue 809 to push against the movable floor 808 to move the movable floor 808 between the open position and the closed position.

In the open position, the movable floor 808 may be flush with a floor 814 of the ramp 806 to enable the pills 805 to slide down the ramp 806 and into the rotating barrel 802. Conversely, in the closed position, the movable floor 808 may be deflected at least partially within the ramp 806 to block and prevent the movement of the pills 805 along the ramp 806 and into the rotating barrel 802. In particular, the movable floor 808 may be deflected at least partially within the ramp 806 to pinch (or press) the pill thereon against a top surface 817 of the ramp 806 to prevent the movement of the pills 805 along the ramp 806 and into the rotating barrel 802.

To enable the movable floor 808 to move in and out of the ramp 806 between the open position and the closed position, the movable floor 808 may be cantilevered along the floor 814 of the ramp 806. That is, only one end of the movable floor 808 may be attached to the floor 814. As a result, the movable floor 808 may be capable of deflecting in and out of the ramp 806. In this manner, the movable floor 808 may move (or oscillate) up and down between the open position and the closed position.

The movable floor 808 may be configured to enable one pill 805 to pass to the rotating barrel 802 at a time. For example, a first pill 822 may be provided to or disposed within the cavity 804, and a second pill 824 may be pinched within the ramp 806 by the movable floor 808 in the closed position. When the rotating barrel 802 rotates, the first pill 822 is dispensed to the dispensing opening and the movable floor 808 is moved from the closed position to the open position via the cam surface 812 and the tongue 809, causing the second pill 824 to slid down the ramp 806 towards the rotating barrel 802. In some instances, a backside 826 of the rotating barrel 802 prevents the second pill 824 from exiting the ramp 806 until the rotating barrel 802 makes a full rotation such that the second pill 824 can exit the ramp 806 into the cavity 804. When the rotating barrel 802 fully rotates such that the second pill 824 can exit the ramp 806 into the cavity 804, the movable floor 808 is moved back into the closed position to prevent other pills from being provided to or entering the cavity 804.

The dispensing mechanism 800 is particularly useful for smaller circular tablets. In particular, the movable floor 808 prevents blockage and jams between the ramp 806 and the rotating barrel 802. For example, smaller pills have a tendency to ride up on top of one another, which causes jams and clogs. The movable floor 808 prevents this by pinching the "on deck" pill in place within the ramp 806. The dispensing mechanism 800 may be used with any sized or shaped pill.

FIGS. 56-61 depict a dispensing mechanism 900 for a portable pill dispenser. The dispensing mechanism 900 may be incorporated into any of the embodiments described herein. In particular, the dispensing mechanism 900 may replace or work in conjunction with the dispensing mechanism 134 in FIGS. 1-13. The dispensing mechanism 900 may be incorporated into any pill dispenser.

The dispensing mechanism 900 comprises a rotating barrel 902. The rotating barrel 902 includes at least one cavity 904 therein. The cavity 904 is configured to receive at least one pill 905 therein. Rotation of the rotating barrel 902 dispenses the pill 905 from the cavity 904 to a dispensing opening in the pill dispenser. The operation of the rotating barrel 902 is similar to the one described in the dispensing mechanism 134 described in FIGS. 1-13.

The dispensing mechanism 900 also includes a ramp 906. The ramp 906 is configured to align and direct the pills 905 to the rotating barrel 902. The ramp 706 may form a channel or passage to the rotating barrel 902. The channel or passage may be circular or square. The ramp 906 may be any suitable size, shape, or configuration. In order to regulate the number of pills 905 passing to the rotating barrel 902, one or more rotating gates 908 are disposed about the ramp 906 to control the movement of the pills 905 to the rotating barrel 902. In some instances, the rotating gates 908 are disposed at or near an end of the ramp 906. The rotating gates 908 may be located at any location along the ramp 906.

In some instances, the rotating gates 908 are configured to rotate within the ramp 906 in order to block the pills 905 from sliding into the rotating barrel 902. For example, the rotating barrel 902 may comprise a neck portion 910 to which the rotating gates 908 are attached. In this manner, as the neck portion 910 rotates, so too do the rotating gates 908.

The rotating gates include a wall 912 with a cutout 914. The wall 912 may be sized and shaped to block (obstruct) the ramp 906 to prevent the passage of pills 905 therethrough, while the cutout 914 may be sized and shaped to enable the pills 905 to pass therethrough. For example, in some instances, the cutout 914 may align flush with a floor 915 and/or side wall of the ramp 906 to enable the pills 905 to slide down the ramp 906 and into the rotating barrel 902. Conversely, when the wall 912 is rotated into the ramp 906, it may block and prevent the movement of the pills 905 along the ramp 906 and into the rotating barrel 902.

In some instances, the cutout 914 includes a hook portion 916. The hook portion 916 may include a chamfered edge or the like. The hook portion 916 is used to separate two pills 905. That is, as the rotating gates 908 rotate, the hook portion 916 may engage the area between two adjacent pills and urge the separation of the two adjacent pills to each side of the wall 912 of the rotating cutout 914.

In some embodiments, the rotating gates 908 include a first rotating gate 918 and a second rotating gate 920. The first rotating gate 918 may be located downhill of the second rotating gate 920 relative to the angle of the ramp 906. In such instances, the cutout 914 in the first rotating gate 918 is offset from the cutout 914 in the second rotating gate 920. That is, when the cutout 914 of the first rotating gate 918 is flush with the floor 915 of the ramp 906 to enable a pill 905 disposed between the first rotating gate 918 and the second rotating gate 920 to slide to the rotating barrel 902, the wall 912 of the second rotating gate 920 may be disposed within the ramp 906 to prevent the movement of pills 905 uphill of the second rotating gate 920. Conversely, when the cutout 914 of the second rotating gate 920 is flush with the floor 915 of the ramp 906 to enable a pill 905 to slide down the ramp 906 to a location between the first rotating gate 918 and the second rotating gate 920, the wall 912 of the first rotating gate 918 may be disposed within the ramp 906 to prevent the movement of pills 905 located between the first rotating gate 918 and the second rotating gate 920 from sliding to the rotating barrel 902.

To enable the rotating gates 908 to rotate about the ramp 906, the ramp 906 includes one or more corresponding apertures 922 therethrough in which the rotating gates 908 can rotate within. In this manner, the rotating gates 908 may rotate within the apertures 922 between an open position, in which the cutout 914 is aligned with the ramp 906, and a closed position, in which the wall 12 is disposed within the ramp 906.

The rotating gates 908 may be configured to enable one pill 905 to pass to the rotating barrel 902 at a time. The dispensing mechanism 900 is particularly useful for smaller circular tablets. In particular, the rotating gates 908 prevent blockage and jams between the ramp 906 and the rotating barrel 902. In an alternative embodiment, the spacing between the gates can be set to permit two or more adjacent pills to pass at a time, e.g., per one revolution of the gates. The dispensing mechanism 900 may be used with any sized or shaped pill.

Figure 63:
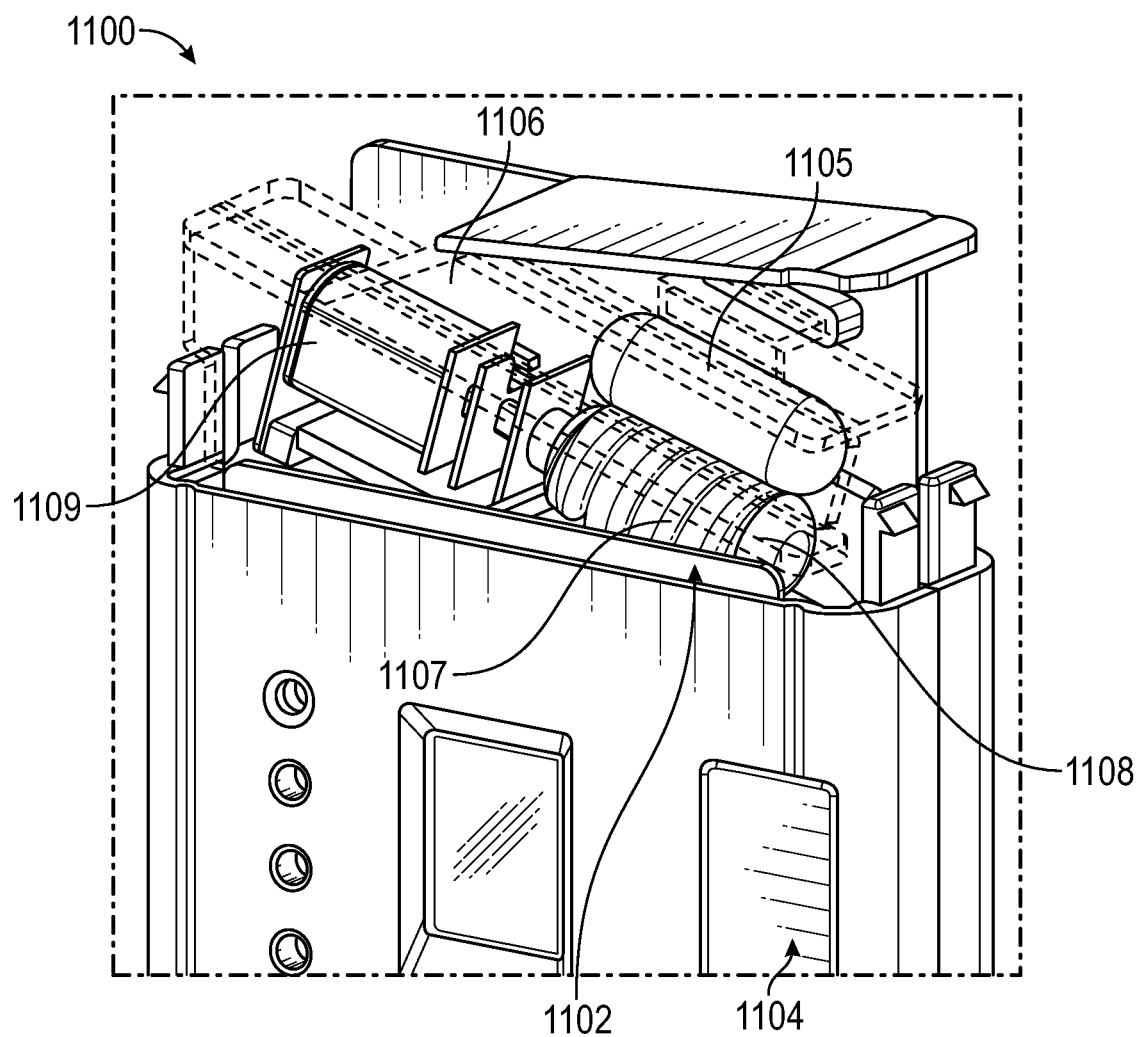
FIG. 63 depicts a dispensing mechanism comprising a rotating screw of a portable pill dispenser in accordance with one or more embodiments of the disclosure.
Figure 64:
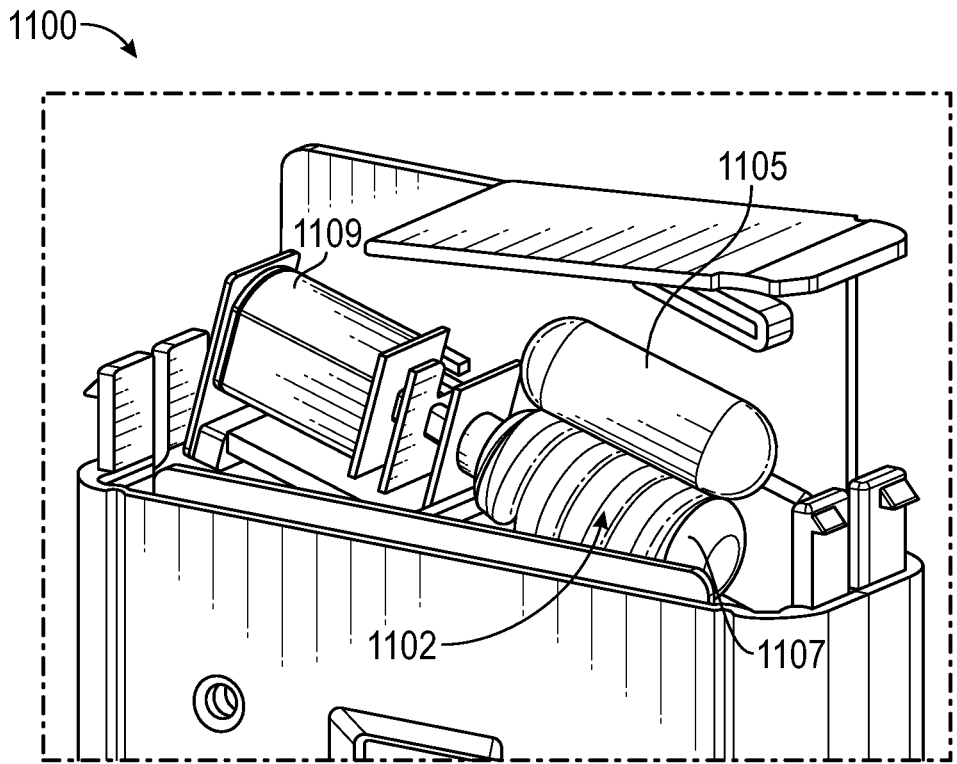
FIG. 64 depicts a dispensing mechanism comprising a rotating screw of a portable pill dispenser in accordance with one or more embodiments of the disclosure.
Figure 65:
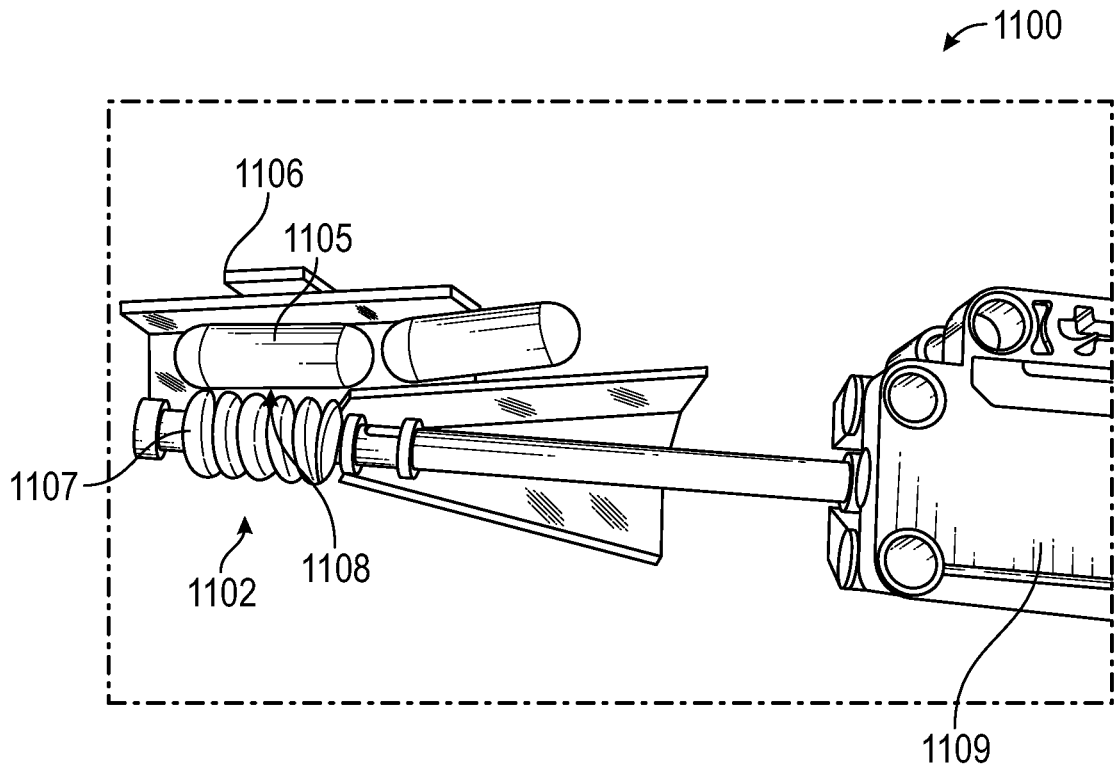
FIG. 65 depicts a dispensing mechanism comprising a rotating screw of a portable pill dispenser in accordance with one or more embodiments of the disclosure.

FIGS. 63-65 depict a dispensing mechanism 1100 for a portable pill dispenser. The dispensing mechanism 1100 may be incorporated into any of the embodiments described herein. In particular, the dispensing mechanism 1100 may replace or work in conjunction with the dispensing mechanism 134 in FIGS. 1-13. The dispensing mechanism 1100 may be incorporated into any pill dispenser.

The dispensing mechanism 1100 comprises a rotating screw 1102. Rotation of the rotating screw 1102 dispenses the pill 1105 to a dispensing opening 1104 in the pill dispenser. In some instances, the rotating screw 1102 may include a helix screw head 1107 or the like. The helix screw head 1107 may be a single unitary structure or a number of bristles forming a helix. In this manner, the rotating screw 1106 may function similar to a screw conveyor for moving the pills 1105 from the container to the dispensing opening 1104. For example, the helix screw head 1107 may be directly or indirectly (e.g., via gears) attached to an actuator 1109, such as a motor, for rotating the helix screw head 1107.

The dispensing mechanism 1100 also includes a ramp 1106. The ramp 1106 is configured to align and direct the pills 1105 to the rotating screw 1102. The ramp 1106 may form a channel or passage to the rotating screw 1102. The channel or passage may be circular or square. The ramp 1106 may be any suitable size, shape, or configuration. In some instances, the rotating screw 1106 may be at least partially disposed within the ramp 1106. More so, the rotating screw 1102 may be disposed at or near an end of the ramp 1106. The rotating screw 1106 may be located at any location along the ramp 1106.

In some instances, the rotating screw 1102 is configured to rotate at least partially within the ramp 1106 in order to move the pills 1105 along the ramp 1106. For example, the rotating screw 1102 may contact and move one or more of the pills 1105 along the ramp 1106 as the rotating screw 1102 rotates. When the rotating screw 1102 is not rotating, the pills 1105 may be blocked by the rotating screw 1102 from sliding along the ramp 1106.

To enable the rotating screw 1102 to rotate about the ramp 1106, the ramp 1106 includes a corresponding aperture 1108 therethrough in which at least a portion of the helix screw head 1107 of the rotating screw 1102 is disposed. The helix screw head 1107 can rotate within the ramp via the aperture 1108. That is, the helix screw head 1107 may rotate within the aperture 1108. The rotating screw 1102 may be at least partially disposed within the ramp 1106 through the aperture 1108 so as to block the passage of pills 1105 therethrough unless the rotating screw 1102 is rotating.

Figure 62:
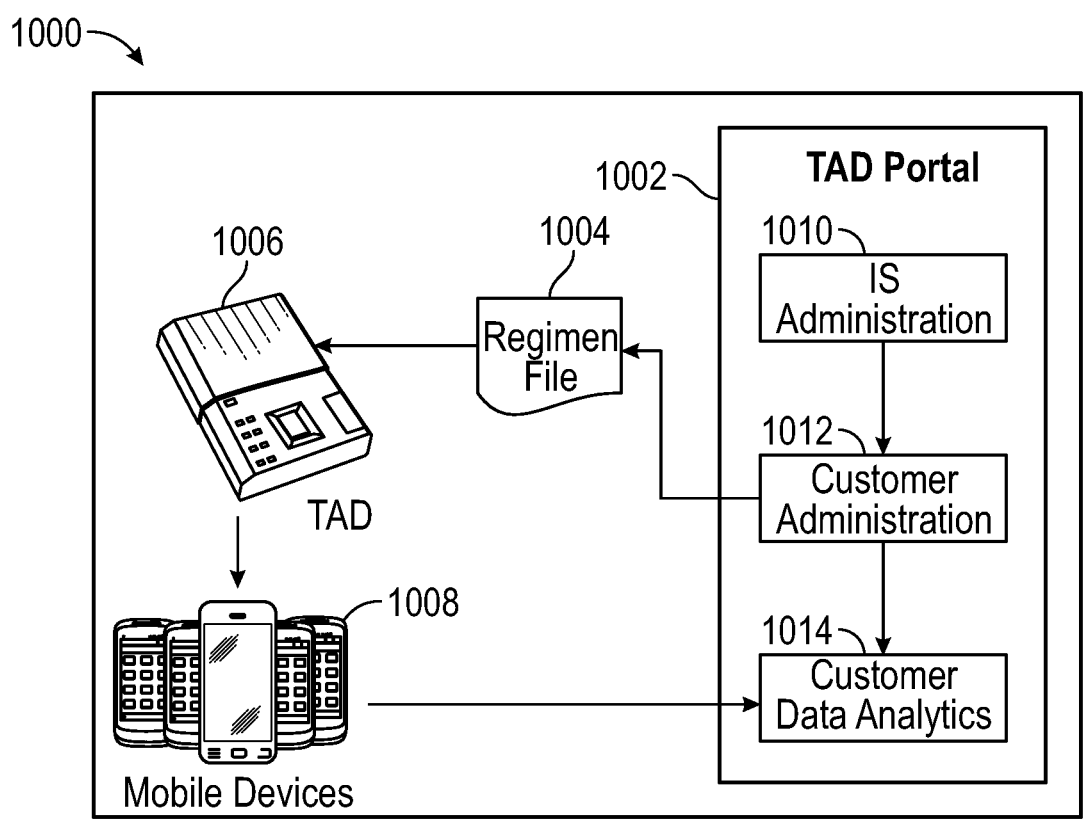
FIG. 62 depicts a communication network in accordance with one or more embodiments of the disclosure.

As depicted in FIG. 62, the various pill dispensers and pill dispensing mechanism disclosed herein, collectively known as smart dispensers, may be incorporated into a pill dispensing and monitoring system 1000. The system 1000 may include a portal 1002, a regimen file 1004, a smart pill dispensing device 1006, and one or more personal computing devices 1008, which may communicate with one another over one or more network connections, which may be hard connections or wireless connections.

In some instances, the system 1000 comprises a combination of a web-based portal, a smart pill dispensing device, and a mobile computing device (e.g., mobile phone) application. The system 1000 is designed to allow customers of the platform, such as clinical research organizations and pain management clinics, to prescribe medication to individuals for the purpose of tracking and managing adherence.

The portal 1002 is used by platform customers to define prescriptions that are then translated into instructions for use with the smart pill dispensing device 1006. The smart pill dispensing device 1006 is then filled with medication and provided to an individual for taking their medication. The smart pill dispensing device 1006 can enroll a fingerprint and/or use a registered PIN to enable dispensation. As an individual dispenses medication using his or her fingerprint or PIN, the smart pill dispensing device 1006 records the dispensation events. That data is subsequently transferred to the portal 1002 for reporting and analysis.

A platform administrator user is a platform employee or contractor who has been granted administrative rights to login to the platform administrative module 1010. A customer administrative user is a user with access rights to a specific platform customer's customer administrative module 1012 that also has authority to perform administrative tasks such as adding new customer users. A customer user is a user with access rights to a specific platform customer's customer administrative module 1012. A participant is an individual that being assigned a smart pill dispensing device 1006 by a customer for the purpose of receiving medication and tracking adherence. A participant profile is a record created within the system 1000 database that relates to a single participant within a customer's participant population. Each participant profile is assigned a unique identifier to be used by the system for linking to related data. Event data is data collected on a smart pill dispensing device 1006 in the form of a series of log entries that include an event type, a date and time of the event, and any related information such as a temperature reading associated with a temperature read event. Each event data record is stored in the system 1000 database with a set of unique keys that tie the event data record to a specific participant and a corresponding regimen file 1004.

The administrative module 1010 is used for on-boarding new clients (add/edit/deactivate customers, setup up master tables), creating customer administrative users and providing customer support. The customer administrative module 1012 allows customer administrative users to set up other customer users, create participant profiles and create regimen files for association with participant smart pill dispensing devices 1006.

A customer data analytics module 1014 allows customer users to review data collected from the smart pill dispensing device 1006 for individual participants and groups of participants. In addition, customer users can review aggregate reports and download raw smart pill dispensing device 1006 data related to their participant population. A regimen file 1004 is a proprietary file containing a set of operating instructions for a smart pill dispensing device 1006. The instructions in the regimen file control smart pill dispensing device 1006 behavior such as time to dispense medication or time to wait between dispensations. These instructions are typically based on an individual participant's prescription requirements. Regimen files are created by customer users within the customer administrative module 1012.

The smart pill dispensing device 1006 is a smart pill dispenser with fingerprint and/or PIN controlled access that dispenses medication, tracks dispensation events and other environmental data such as temperature, humidity, battery level, etc. Event data is stored on the device and transferred to the system database via the mobile application 1008 on the personal computing device or by a customer user manually copying and importing the event data into the system.

The mobile application 1008 is a platform mobile application that is used to gather event data from the smart pill dispensing device 1006 and transfer the data to the system database. The mobile application 1008 connects to a smart pill dispensing device 1006 over bluetooth and can also provide a participant with information about the smart pill dispensing device 1006, such as last dispensation date/time and instructions for using the smart pill dispensing device 1006. In addition, the mobile application 1008 allows a user to establish and maintain a personal identification number (PIN) and store the PIN in the customer administrative module 1012. Subsequently, the mobile application can enable dispensation mode if a valid PIN is provided.

In use, for example, a platform administrator can create a customer administration user account for a new customer. The customer administrative user on boards other users such as pharmacists and other customer users. A customer user creates participant profiles for participants who will be taking medication using a smart pill dispensing device 1006. A pharmacist creates a prescription for medication for a participant and associates the prescription with a smart pill dispensing device 1006. A customer user defines a prescription for a participant and creates a regimen file based on that prescription. The customer user downloads the regimen file and copies it to a participant's smart pill dispensing device 1006 to enable tracking and dispensing of the medication according to the prescribed regimen. The participant registers a fingerprint on the device and/or establishes a PIN to control dispensation. During the course of the prescribed regimen, the participant enters their PIN into the mobile application or places his or her finger on the smart pill dispensing device 1006 fingerprint reader to authorize dispensation each time medication is dispensed. The smart pill dispensing device 1006 collects event data as long as it has power (i.e. battery is sufficiently charged).

The participant connects to the smart pill dispensing device 1006 from time to time over a bluetooth connection using the mobile application. The mobile application transfers event data to the system. Optionally, when the smart pill dispensing device 1006 is turned back in when a refill is required or at the end of the prescription, the event data can be extracted over a USB connection and uploaded to the system database. Event data is associated with the participant to whom the data pertains using a combination of the smart pill dispensing device 1006 MAC address and the regimen file ID. Customer users analyze the event data for participants or groups of participants as individuals or in aggregate.

Any combination of the dispensing mechanisms disclosed herein may be used. That is, all or portions of one dispensing mechanism may be incorporated or combined into another dispensing mechanism.

Although specific embodiments of the disclosure have been described, numerous other modifications and alternative embodiments are within the scope of the disclosure. For example, any of the functionality described with respect to a particular device or component may be performed by another device or component. Further, while specific device characteristics have been described, embodiments of the disclosure may relate to numerous other device characteristics. Further, although embodiments have been described in language specific to structural features and/or methodological acts, it is to be understood that the disclosure is not necessarily limited to the specific features or acts described. Rather, the specific features and acts are disclosed as illustrative forms of implementing the embodiments. Conditional language, such as, among others, "can," "could," "might," or "may," unless specifically stated otherwise, or otherwise understood within the context as used, is generally intended to convey that certain embodiments could include, while other embodiments may not include, certain features, elements, and/or steps. Thus, such conditional language is not generally intended to imply that features, elements, and/or steps are in any way required for one or more embodiments.

We claim:

1. A portable pill dispenser, comprising:
a container configured to house at least one pill therein;
a housing attachable to the container, wherein the housing comprises a dispensing opening;
a dispensing mechanism disposed within the housing, wherein the dispensing mechanism is configured to dispense the at least one pill from the container to the dispensing opening, wherein the dispensing mechanism comprises a rotating barrel comprising at least one cavity configured to receive the at least one pill therein, wherein rotation of the rotating barrel dispenses the at least one pill to the dispensing opening, wherein the rotating barrel comprises a neck portion having a cam surface;
a ramp disposed within the housing, wherein the ramp is configured to direct the at least one pill to the dispensing mechanism; and
one or more moveable stoppers disposed about the ramp to control the movement of the at least one pill to the dispensing mechanism,
wherein the cam surface is in mechanical communication with the one or more stoppers and is configured to move the one or more moveable stoppers between an open position and a closed position as the neck portion rotates.

2. The portable pill dispenser of claim 1, wherein the ramp comprises one or more apertures therethrough for the one or more movable stoppers to pass.

3. The portable pill dispenser of claim 1, wherein the one or more movable stoppers comprise two spaced apart pins that move up and down along the cam surface as the neck portion rotates.

4. The portable pill dispenser of claim 1, wherein the at least one pill comprises a first pill disposed within the at least one cavity and a second pill blocked within the ramp by the one or more moveable stoppers in the closed position.

5. The portable pill dispenser of claim 4, wherein when the rotating barrel rotates, the first pill is dispensed to the dispensing opening and the one or more moveable stoppers are moved from the closed position to the open position causing the second pill to slid down the ramp towards the rotating barrel.

6. The portable pill dispenser of claim 5, wherein a backside of the rotating barrel prevents the second pill from exiting the ramp until the rotating barrel makes a full rotation such that the second pill can exit the ramp into the cavity.

7. The portable pill dispenser of claim 6, wherein when the rotating barrel fully rotates such that the second pill can exit the ramp into the cavity, the one or more moveable stoppers are moved back into the closed position to prevent other pills from entering the cavity.

8. The portable pill dispenser of claim 1, further comprising a moveable floor disposed within the ramp to control the movement of the at least one pill to the dispensing mechanism.

9. The portable pill dispenser of claim 8, wherein the cam surface is in mechanical communication with the moveable floor and is configured to move the moveable floor between the open position and the closed position as the neck portion rotates.

10. The portable pill dispenser of claim 8, wherein the moveable floor is cantilevered within the ramp.

11. The portable pill dispenser of claim 8, further comprising a tongue in mechanical communication with the movable floor and the cam surface.

12. The portable pill dispenser of claim 8, wherein the at least one pill comprises a first pill disposed within the at least one cavity and a second pill blocked within the ramp by the moveable floor in the closed position.

13. The portable pill dispenser of claim 8, wherein when the rotating barrel rotates, the first pill is dispensed to the dispensing opening and the moveable floor is moved from the closed position to the open position causing the second pill to slide down the ramp towards the rotating barrel.

14. The portable pill dispenser of claim 8, wherein a backside of the rotating barrel prevents the second pill from exiting the ramp until the rotating barrel makes a full rotation such that the second pill can exit the ramp into the cavity.

15. The portable pill dispenser of claim 8, wherein when the rotating barrel fully rotates such that the second pill can exit the ramp into the cavity, the moveable floor is moved back into the closed position to prevent other pills from entering the cavity.

16. A portable pill dispenser, comprising:
a container configured to house at least one pill therein;
a housing attachable to the container, wherein the housing comprises a dispensing opening;
a dispensing mechanism disposed within the housing, wherein the dispensing mechanism is configured to dispense the at least one pill from the container to the dispensing opening, wherein the dispensing mechanism comprises a rotating barrel comprising at least one cavity configured to receive the at least one pill therein, wherein rotation of the rotating barrel dispenses the at least one pill to the dispensing opening;
a ramp disposed within the housing, wherein the ramp is configured to direct the at least one pill to the dispensing mechanism;
a moveable floor disposed within the ramp to control the movement of the at least one pill to the dispensing mechanism,
wherein when the rotating barrel fully rotates such that the second pill can exit the ramp into the cavity, the moveable floor is moved into a closed position to prevent other pills from entering the cavity.

* * * * *